US011058654B2

(12) United States Patent
Carroll et al.

(10) Patent No.: US 11,058,654 B2
(45) Date of Patent: Jul. 13, 2021

(54) COMPOSITIONS AND METHODS FOR THE TREATMENT OF HEMOGLOBINOPATHIES AND THALASSEMIAS

(71) Applicant: AXCELLA HEALTH INC., Cambridge, MA (US)

(72) Inventors: Sean Carroll, Cambridge, MA (US); Matthew Russell, West Newton, MA (US); Raffi Afeyan, Boston, MA (US)

(73) Assignee: AXCELLA HEALTH INC., Cambridge, MA (US)

( * ) Notice: Subject to any disclaimer, the term of this patent is extended or adjusted under 35 U.S.C. 154(b) by 0 days.

(21) Appl. No.: 16/446,374

(22) Filed: Jun. 19, 2019

(65) Prior Publication Data
US 2019/0388376 A1    Dec. 26, 2019

Related U.S. Application Data

(60) Provisional application No. 62/804,879, filed on Feb. 13, 2019, provisional application No. 62/687,721, filed on Jun. 20, 2018.

(51) Int. Cl.
| | |
|---|---|
| *A61K 31/198* | (2006.01) |
| *A23L 33/18* | (2016.01) |
| *A23L 33/175* | (2016.01) |
| *A61K 31/205* | (2006.01) |
| *A61K 31/4172* | (2006.01) |
| *A61K 38/05* | (2006.01) |
| *A61K 38/06* | (2006.01) |

(52) U.S. Cl.
CPC .......... *A61K 31/198* (2013.01); *A23L 33/175* (2016.08); *A23L 33/18* (2016.08); *A61K 31/205* (2013.01); *A61K 31/4172* (2013.01); *A61K 38/05* (2013.01); *A61K 38/06* (2013.01)

(58) Field of Classification Search
CPC .............. A61K 2300/00; A61K 31/198; A61K 31/205; A61K 31/4172; A61K 38/05; A61K 38/06; A61K 45/06; A23L 33/175; A23L 33/18
See application file for complete search history.

(56) References Cited

U.S. PATENT DOCUMENTS

| | | | |
|---|---|---|---|
| 5,693,671 A | 12/1997 | Niihara et al. | |
| 6,028,107 A | 2/2000 | Waugh | |
| 6,087,398 A | 7/2000 | Goodman | |
| 6,251,927 B1 | 6/2001 | Lai et al. | |
| 6,864,242 B2* | 3/2005 | Ernest | A23L 33/40 |
| | | | 514/27 |
| 7,196,065 B2 | 3/2007 | Ernest | |
| 8,309,320 B2 | 11/2012 | Morris et al. | |
| 8,840,950 B2 | 9/2014 | Hibbert et al. | |
| 8,980,823 B2 | 3/2015 | Mousa | |
| 9,040,082 B2 | 5/2015 | Kaiser | |
| 9,089,548 B2 | 7/2015 | Inufusa | |
| 9,375,451 B2 | 6/2016 | Hibbert et al. | |
| 9,616,041 B2 | 4/2017 | Niihara | |
| 9,822,190 B2 | 11/2017 | Mousa | |
| 9,878,004 B2 | 1/2018 | Williams et al. | |
| 10,201,513 B2 | 2/2019 | Hamill et al. | |
| 10,238,617 B2 | 3/2019 | Hamill et al. | |
| 10,471,034 B2* | 11/2019 | Hamill | A61K 38/06 |
| 10,596,136 B2 | 3/2020 | Chakravarthy et al. | |
| 10,660,870 B2 | 5/2020 | Comb et al. | |
| 10,682,325 B2 | 6/2020 | Comb et al. | |
| 2005/0158401 A1 | 7/2005 | Morris | |
| 2007/0286909 A1 | 12/2007 | Smith et al. | |
| 2009/0234011 A1 | 9/2009 | Goldstein | |
| 2009/0306209 A1 | 12/2009 | Daugherty et al. | |
| 2011/0294727 A1 | 12/2011 | Hibbert et al. | |
| 2012/0316121 A1 | 12/2012 | Allen | |
| 2014/0315788 A1 | 10/2014 | Wolfe et al. | |
| 2016/0058819 A1 | 3/2016 | Hibbert et al. | |
| 2016/0199337 A1 | 7/2016 | Morris | |
| 2016/0339078 A1 | 11/2016 | Hamill et al. | |
| 2017/0056381 A1 | 3/2017 | Isaacman et al. | |
| 2017/0087180 A1 | 3/2017 | Giordano et al. | |
| 2018/0125926 A1 | 5/2018 | Williams et al. | |
| 2018/0169044 A1 | 6/2018 | Hamill et al. | |
| 2018/0169045 A1 | 6/2018 | Hamill et al. | |
| 2018/0169046 A1 | 6/2018 | Hamill et al. | |
| 2018/0169047 A1 | 6/2018 | Hamill et al. | |
| 2018/0207118 A1 | 7/2018 | Hamill et al. | |
| 2018/0207119 A1 | 7/2018 | Hamill et al. | |
| 2018/0296516 A1 | 10/2018 | Hamill et al. | |
| 2019/0046486 A1 | 2/2019 | De Rienzo et al. | |
| 2019/0046487 A1 | 2/2019 | Comb et al. | |

(Continued)

FOREIGN PATENT DOCUMENTS

| | | |
|---|---|---|
| CN | 101049500 A | 10/2007 |
| IN | 201503117 I3 | 10/2016 |

(Continued)

OTHER PUBLICATIONS

Ortiz de Montellano et al., "A New Step in the Treatment of Sickle Cell Disease," Biochemistry (2018) vol. 57, No. 5, pp. 470-471, Abstract.

(Continued)

*Primary Examiner* — Marcela M Cordero Garcia
(74) *Attorney, Agent, or Firm* — Lando & Anastasi, LLP

(57) ABSTRACT

This disclosure provides compositions and methods for improving erythrocyte dysfunction or treating a hemoglobinopathy or a thalassemia (e.g., sickle cell disease or β-thalassemia).

14 Claims, 4 Drawing Sheets

(56) References Cited

U.S. PATENT DOCUMENTS

| | | |
|---|---|---|
| 2019/0105294 A1 | 4/2019 | Hamill et al. |
| 2019/0183961 A1 | 6/2019 | Westphal et al. |
| 2019/0247351 A1 | 8/2019 | Comb et al. |
| 2019/0388374 A1 | 12/2019 | Hanlon et al. |
| 2019/0388375 A1 | 12/2019 | Hanlon et al. |
| 2019/0388376 A1 | 12/2019 | Carroll et al. |
| 2019/0388377 A1 | 12/2019 | Hamill et al. |
| 2020/0016104 A1 | 1/2020 | Chakravarthy et al. |
| 2020/0163919 A1 | 5/2020 | Carroll et al. |
| 2020/0281882 A1 | 9/2020 | Chakravarthy et al. |
| 2020/0306214 A1 | 10/2020 | Comb et al. |
| 2020/0330417 A1 | 10/2020 | Hamill et al. |

FOREIGN PATENT DOCUMENTS

| | | |
|---|---|---|
| WO | 2005017094 A2 | 2/2005 |
| WO | 2006002096 A2 | 1/2006 |
| WO | 2009149196 A1 | 12/2009 |
| WO | 2011149713 A2 | 12/2011 |
| WO | 2015048333 A2 | 4/2015 |
| WO | 2015048340 A2 | 4/2015 |
| WO | 2015048342 A2 | 4/2015 |
| WO | 2015048345 A2 | 4/2015 |
| WO | 2015048346 A2 | 4/2015 |
| WO | 2015048348 A2 | 4/2015 |
| WO | 2015106240 A1 | 7/2015 |
| WO | 2016033187 A1 | 3/2016 |
| WO | 2018157137 A1 | 8/2018 |

OTHER PUBLICATIONS

Pace et al., "Effect of N-acetylcysteine on Dense Cell Formation in Sickle Cell Disease," American Journal of Hematology (2003) vol. 73, No. 1, pp. 26-32.

Waugh et al., "Evidence that L-Arginine is a Key Amino Acid in Sickle Cell Anemia—A Preliminary Report," Nutrition Research (1999) Vol. 19, No. 4, pp. 501-518.

[No Author Listed] "A Phase III Safety and Efficacy Study of L-Glutamine to Treat Sickle Cell Disease or Sicle Beta-thalassemia," Clinical Trials.gov identifier NCT01179217, last updated Aug. 10, 2017, 9 pages.

[No Author Listed] Asthéplex Dietary Supplement Product Details retrieved from Database GNBD Mintel, gnpd.com, Accession No. 2240930, 4 pages, 2013.

Baron et al., "Insulin-mediated Skeletal Muscle Vasodilation Contributes to Both Insulin Sensitivity and Responsiveness in Lean Humans," J Clin Invest (1995) vol. 96, pp. 786-792.

Brack et al., "The ins and outs of muscle stem cell aging," Skeletal Muscle (2016) vol. 6, No. 1, 9 pages.

Børsheim et al., "Effect of amino acid supplementation on muscle mass, strength and physical function in elderly," Clin Nutr (2008) vol. 27, pp. 189-195.

Børsheim et al., "Essential amino acids and muscle protein recovery from resistance exercise," Am J Physiol Endocrinol Metab (2002) vol. 283, pp. E648-E657.

Chantranupong et al., "The CASTOR Proteins Are Arginine Sensors for the mTORC1 Pathway," Cell (2016) vol. 165, pp. 153-164.

Churchward-Venne et al., "Supplementation of a suboptimal protein dose with leucine or essential amino acids: effects on myofibrillar protein syntheses at rest and following resistance exercise in men," J Physiol (2012) vol. 590, No. 11, pp. 2751-2765.

Gannon et al., "Amino Acid Ingestion and Glucose Metabolism—A Review," IUBMB Life (2010) vol. 62, No. 9, pp. 660-668.

Heyland et al., "A Randomized Trial of Glutamine and Antioxidants in Critically Ill Patients," N Engl J Med (2013) vol. 368, pp. 1489-1497.

International Search Report and Written Opinion issued in PCT/US2019/037925, dated Oct. 4, 2019.

Lomonosova et al., "L-arginine Supplementation Protects Exercise Performance and Structural Integrity of Muscle Fibers after a Single Bout of Eccentric Exercise in Rats," PLOS One (2014) vol. 9, No. 4. Article e94448, 10 pages.

Majumdar et al., "A phase 1 dose-finding study of intravenous L-citrulline in sickle cell disease: a potential novel therapy for sickle cell pain crisis," British Journal of Haematology (2019) vol. 184, pp. 634-636.

Martina et al., "Long-Term N-Acetylcysteine and L-Arginine Administration Reduces Endothelial Activation and Systolic Blood Pressure in Hyptertensive Patients With Type 2 Diabetes," Diabetes Care (2008) vol. 31, No. 5, pp. 940-944.

Mendelson, "Metabolic Syndrome and Psychiatric Illness," Chapter 10: Nutritional Supplements and Metabolic Syndrome, pp. 141-186, Elsevier, 2008.

Niihara et al., "A Phase 3 Trial of L-Glutamine in Sickle Cell Disease," N Engl J Med (2018) vol. 379, pp. 226-235.

Pace et al., "Effects of N-Acetylcysteine on Dense Cell Formation in Sickle Cell Disease," American Journal of Hematology (2003) vol. 73, pp. 26-32.

Paddon-Jones et al., "Essential Amino Acid and Carbohydrate Supplementation Ameliorates Muscle Protein Loss in Humans during 28 Days Bedrest," J Clin Endocrinol Metab (2004) vol. 89, pp. 4351-4358.

Rathmacher et al., "Supplementation with a combination of beta-hydroxy-beta-methylbutyrate (HMB), arginine, and glutamine is safe and could improve hematological parameters," J Parenter Enteral Nutr (2004) vol. 28, No. 2, pp. 65-75.

Reid et al., "N-Acetylcysteine Inhibits Muscle Fatigue in Humans," J Clin Invest (1994) vol. 94, pp. 2468-2474.

Rennie et al., "Interaction between Glutamine Availability and Metabolism of Glycogen Tricarboxylic Acid Cycle Intermediates and Glutathione," J Nutr (2001) vol. 131, pp. 2488S-2490S.

Rodgers et al., "mTORC1 controls the adaptive transition of quiescent stem cells from G0 to GAlert," Nature (2014) vol. 510, pp. 393-396.

Salehian et al., "The effect of glutamine on prevention of glucocorticoid-induced skeletal muscle atrophy is associated with myostatin suppression," Metabolism Clinical and Experimental (2006) vol. 55, pp. 1239-1247.

Saxton et al., "Mechanism of arginine sensing by CASTOR1 upstream of mTORC1," Nature (2016) vol. 536, pp. 229-239 and methods pages.

Saxton et al., "Structural basis for leucine sensing by the Sestrin2-mTORC1 pathway," Science (2016) vol. 351, Issue 6268, pp. 53-58.

Talbert et al., "Immobilization-induced activation of key proteolytic systems in skeletal muscles is prevented by a mitochondria-targeted antioxidant," J Appl Physiol (2013) vol. 115, pp. 529-538.

Telen et al., "Therapeutic strategies for sickle cell disease: towards a multi-agent approach," Nat Rev Drug Discov (2018) vol. 18, No. 2, pp. 139-158.

Tsuda et al., "Combined Effect of Arginine, Valine, and Serine on Excercise-Induced Fatigue in Healthy Volunteers: A Randomized, Double-Blind, Placebo-Controlled Crossover Study," Nutrients (2019) vol. 11, Article 862, 12 pages.

Wolfson et al., "Sestrin2 is a leucine sensor for the mTORC1 pathway," Science (2016) vol. 351, Issue 6268, pp. 43-48.

* cited by examiner

COMPOSITIONS AND METHODS FOR THE TREATMENT OF HEMOGLOBINOPATHIES AND THALASSEMIAS

RELATED APPLICATIONS

This application claims priority to U.S. Ser. No. 62/687,721 filed Jun. 20, 2018 and to U.S. Ser. No. 62/804,879 filed Feb. 13, 2019, the contents of which are incorporated herein by reference in their entirety.

BACKGROUND

Hemoglobinopathies, such as sickle cell disease, are highly prevalent genetic erythrocyte disorders that cause a significant health burden worldwide. Hemoglobinopathies encompass a number of anemias of genetic origin in which there is a decreased production and/or increased hemolysis of erythrocytes. In particular, sickle cell disease is a group of genetic disorders that manifest in the production of sickle-shaped erythrocytes and are characterized by hemolytic anemia and vaso-occlusion events in addition to intense periods of pain, organ failure, and early mortality. Sickle cell anemia is the most common and severe form of sickle cell disease (SCD), affecting approximately 100,000 people in the United States and 4.4 million worldwide. For many patients, SCD is defined by chronic organ failure punctuated by acute complications and early mortality. Current therapies for SCD are limited to supportive treatment of complications, erythrocyte transfusions, hydroxyurea, and stem cell transplantation.

Given the lack of available therapies, there is still a need for agents, e.g., dietary compositions and therapeutics for treating hemoglobinopathies, such as SCD, in a subject.

SUMMARY OF THE INVENTION

Provided herein is a composition (e.g., an Active Moiety) including amino acid entities that is useful for improving erythrocyte and/or hemoglobin function, turnover, and synthesis; vascular function; inflammation; and/or oxidative stress in a subject, e.g., a subject with a hemoglobinopathy (e.g., sickle cell disease) or a thalassemia (e.g. α-thalassemia or β-thalassemia). The composition can be used in a method of treating (e.g., reversing, reducing, ameliorating, or preventing) one or more symptoms of a hemoglobinopathy or a thalassemia in a subject in need thereof (e.g, a human). The method can further include monitoring the subject for an improvement in one or more symptoms of a hemoglobinopathy or a thalassemia after administration of the composition.

In one aspect, the invention features a method of improving one, two, three, four, five, six or more (e.g., all) of erythrocyte function, turnover, or synthesis; hemoglobin function, turnover, or synthesis; or vascular function, comprising administering to a subject in need thereof an effective amount of a composition (e.g., an Active Moiety) comprising:
  a) a leucine amino acid entity,
  b) a arginine amino acid entity,
  c) glutamine amino acid entity; and
  d) a N-acetylcysteine (NAC)-entity;
the composition does not comprise a peptide of more than 20 amino acid residues in length (e.g., whey protein), or if a peptide of more than 20 amino acid residues in length is present, the peptide is present at less than: 10 wt. % of the total wt. of the composition (e.g., in dry form);
thereby improving one, two, three, four, five, six or more (e.g., all) of erythrocyte function, turnover, or synthesis; hemoglobin function, turnover, or synthesis; or vascular function in the subject.

In another aspect, the invention features a method of improving erythrocyte function comprising administering to a subject in need thereof an effective amount of the composition described herein.

In another aspect, the invention features a method of improving erythrocyte turnover comprising administering to a subject in need thereof an effective amount of the composition described herein.

In another aspect, the invention features a method of improving erythrocyte synthesis comprising administering to a subject in need thereof an effective amount of the composition described herein.

In another aspect, the invention features a method of improving hemoglobin function comprising administering to a subject in need thereof an effective amount of the composition described herein.

In another aspect, the invention features a method of improving hemoglobin turnover comprising administering to a subject in need thereof an effective amount of the composition described herein.

In another aspect, the invention features a method of improving hemoglobin synthesis comprising administering to a subject in need thereof an effective amount of the composition described herein.

In another aspect, the invention features a method of improving vascular function comprising administering to a subject in need thereof an effective amount of the composition described herein. In another aspect, the invention features a method of treating a hemoglobinopathy or a thalassemia, comprising administering to a subject in need thereof an effective amount of a composition (e.g., an Active Moiety) comprising:
  a) a leucine amino acid entity,
  b) a arginine amino acid entity,
  c) glutamine amino acid entity; and
  d) a N-acetylcysteine (NAC)-entity;
the composition does not comprise a peptide of more than 20 amino acid residues in length (e.g., whey protein), or if a peptide of more than 20 amino acid residues in length is present, the peptide is present at less than: 10 wt. % of the total wt. of the composition (e.g., in dry form);
thereby treating the hemoglobinopathy or the thalassemia in the subject.

In another aspect, the invention features a method of decreasing oxidative stress (e.g., one or both of blood and systemic oxidative stress) or inflammation, comprising administering to a subject in need thereof an effective amount of a composition (e.g., an Active Moiety) of any of the aspects or embodiments described herein. In some embodiments, the subject is at risk of, or has been diagnosed with a hemoglobinopathy (e.g., a β-hemoglobinopathy) or a thalassemia. In certain embodiments, the hemoglobinopathy is a sickle cell disease. In another embodiment, the α-thalassemia is α-thalassemia or β-thalassemia.

In another aspect, the invention features a composition for use in a method of improving one, two, three, four, five, six or more (e.g., all) of erythrocyte function, turnover, or synthesis; hemoglobin function, turnover, or synthesis; or vascular function in a subject in need thereof, wherein the composition comprises an effective amount of:
  a) a leucine amino acid entity,
  b) a arginine amino acid entity,
  c) glutamine amino acid entity; and
  d) a N-acetylcysteine (NAC)-entity, wherein the composition does not comprise a peptide of more than 20 amino acid residues in length (e.g., whey protein), or if a peptide of more than 20 amino acid residues in length is present, the peptide is present at less than: 10 wt. % of the total wt. of the total components of the composition (e.g., in dry form).

In another aspect, the invention features a method of treating a hemoglobinopathy or a thalassemia in a subject in need thereof, wherein the composition comprises an effective amount of:
  a) a leucine amino acid entity,
  b) a arginine amino acid entity,
  c) glutamine amino acid entity; and
  d) a N-acetylcysteine (NAC)-entity
wherein the composition does not comprise a peptide of more than 20 amino acid residues in length (e.g., whey protein), or if a peptide of more than 20 amino acid residues in length is present, the peptide is present at less than: 10 wt. % of the total components of the composition (e.g., in dry form). In some embodiments, the sickle cell disease is chosen from: sickle cell anemia (HbSS), Hemoglobin SC disease (HbSC), sickle $\beta^+$-thalassemia (HbS/$\beta$+), sickle $\beta^0$-thalassemia (HbS/$\beta^0$), hemoglobin SE disease, hemoglobin SD disease, or hemoglobin SO disease.

In some embodiments, administration of the composition results in one, two, three, four, five, six, seven, eight or more (e.g., all) of: a decrease in reactive oxygen species production; a decrease in a level or activity of plasma arginase; an increase in glutathione synthesis; a decrease in erythrocyte adhesion to endothelial and other cells; an increase in erythrocyte resistance to sickling; an increase in erythrocyte calcium influx; an increase in anabolism; an increase in nitric oxide synthesis; or an increase in hemoglobin synthesis.

In some embodiments, administration of the composition results in an improvement in one, two, three, four, or more (e.g., all) of: anemia; hemolysis; vaso-occlusion; ichemia; or pain.

In some embodiments, the composition further comprises: (e) one or both of a glycine amino acid entity or a carnitine entity.

In another aspect, the invention features a composition comprising, consisting essentially of, or consisting of:
  a) a leucine amino acid entity,
  b) a arginine amino acid entity,
  c) glutamine amino acid entity;
  d) a N-acetylcysteine (NAC) entity; and
  e) one or both of a glycine amino acid entity or a carnitine entity.

In some embodiments, the wt. % of the carnitine entity is at least 1 wt. % of the amino acid entity components or total components in the composition (e.g., in dry form).

In some embodiments, the wt. % of the glycine amino acid entity is at least 3 wt. % of the amino acid entity components or total components in the composition (e.g., in dry form).

In some embodiments, isoleucine is absent from the composition, or if present, is present at less than: 10 wt. %, 1 wt. %, 0.5 wt. %, 0.1 wt. %, 0.05 wt. %, 0.01 wt. %, 0.001 wt. %, or less, e.g., of the total wt. of the composition (e.g., in dry form).

In some embodiments, the composition further comprises one, two, or more (e.g., all) of (f) a valine amino acid entity, (g) a histidine amino acid entity, or (h) a lysine amino acid entity.

In some embodiments, one, two, three, four, five, six, seven, or more (e.g., all) of (a)-(h) is selected from Table 1.

In some embodiments, the composition does not comprise a peptide of more than 20 amino acid residues in length (e.g., whey protein), or if a peptide of more than 20 amino acid residues in length is present, the peptide is present at less than: 10 wt. %, 1 wt. %, 0.5 wt. %, 0.1 wt. %, 0.05 wt. %, 0.01 wt. %, 0.001 wt. %, or less of the total wt. of the total components of the composition (e.g., in dry form).

In some embodiments, one, two, three, four, five, six, seven, or more (e.g., all) of (a)-(h) are in free amino acid form in the composition, e.g., at least: 42 wt. %, 75 wt. %, 90 wt. %, or more, of the total wt. of the composition (e.g., in dry form) is one, two, three, four, five, or more (e.g., all) of (a)-(f) in free amino acid form in the composition.

In some embodiments, the total wt. % of (a)-(d), (a)-(e), (a)-(f), or (a)-(h) is greater than the total wt. % of non-amino acid entity protein components (e.g., whey protein) or non-protein components (or both) in the composition (e.g., in dry form), e.g., (a)-(d), (a)-(e), (a)-(f), or (a)-(h) is at least: 50 wt. 75 wt. %, or 90 wt. % of the total wt. of the total components in the composition (e.g., in dry form).

In some embodiments, the composition comprises a combination of 18 or fewer, 15 or fewer, or 12 or fewer amino acid entities, e.g., the combination comprising at least: 42 wt. %, 75 wt. %, or 90 wt. % of the total wt. of amino acid entity components or total components in the composition (e.g., in dry form).

In some embodiments, tryptophan is absent from the composition, or if present, is present at less than: 10 wt. %, 1 wt. %, 0.5 wt. %, 0.1 wt. %, 0.05 wt. %, 0.01 wt. %, 0.001 wt. %, or less, e.g., of the total wt. of the composition (e.g., in dry form). In some embodiments, tryptophan, if present, is present in free form. In some embodiments, tryptophan, if present, is present in salt form.

In some embodiments, tryptophan, if present, may be present in an oligopeptide, polypeptide, or protein, with the proviso that the protein is not whey, casein, lactalbumin, or any other protein used as a nutritional supplement, medical food, or similar product, whether present as intact protein or protein hydrolysate.

In some embodiments, the wt. ratio of the leucine amino acid entity, the arginine amino acid entity, the glutamine amino acid entity, and the NAC entity is 3.6+/−20%:4.5+/−20%:11+/−20%:1.2+/−20%. In some embodiments, the wt. ratio of the leucine amino acid entity, the arginine amino acid entity, the glutamine amino acid entity, the NAC entity, the carnitine entity, and the glycine amino acid entity is 3.6+/−20%:4.5+/−20%:11+/−20%:1.2+/−20%:1+/−20%:2.7+/−20%.

In some embodiments, the composition (e.g., the Active Moiety) comprises, consists essentially of, or consists of:
  a) the leucine amino acid entity is chosen from:
    i) L-leucine or a salt thereof,
    ii) a dipeptide or salt thereof, or tripeptide or salt thereof, comprising L-leucine, or
    iii) β-hydroxy-β-methylbutyrate (HMB) or a salt thereof;
  b) the arginine amino acid entity is chosen from:
    i) L-arginine or a salt thereof,
    ii) a dipeptide or salt thereof, or tripeptide or salt thereof, comprising L-arginine,
    iii) creatine or a salt thereof, or
    v) a dipeptide or salt thereof, or tripeptide or salt thereof, comprising creatine;
  c) the glutamine amino acid entity is L-glutamine or a salt thereof or a dipeptide or salt thereof, or tripeptide or salt thereof, comprising L-glutamine;

d) the NAC entity is NAC or a salt thereof or a dipeptide or salt thereof, comprising NAC; and
e) one or both of:
  i) the glycine amino acid entity is L-glycine or a salt thereof or a dipeptide or salt thereof, or tripeptide or salt thereof, comprising L-glycine; or
  ii) the carnitine entity is L-carnitine or a salt thereof, or a dipeptide or salt thereof, comprising L-carnitine.

In some embodiments, the composition (e.g., an Active Moiety) further comprises one, two, or more (e.g., all) of:
(f) the valine amino acid entity is L-valine or a salt thereof or a dipeptide or salt thereof, or tripeptide or salt thereof, comprising L-valine;
(g) the histidine amino acid entity is L-histidine or a salt thereof or a dipeptide or salt thereof, or tripeptide or salt thereof, comprising L-histidine; or
(h) the lysine amino acid entity is L-lysine or a salt thereof or a dipeptide or salt thereof, or tripeptide or salt thereof, comprising L-lysine.

In some embodiments, the composition (e.g., an Active Moiety) comprises, consists essentially of, or consists of:
a) the leucine amino acid entity is L-leucine or a salt thereof;
b) the arginine amino acid entity is L-arginine or a salt thereof;
c) the glutamine amino acid entity is L-glutamine or a salt thereof;
d) the NAC entity is NAC or a salt thereof; and
e) one or both of the glycine amino acid entity is L-glycine or a salt thereof or the carnitine entity is L-carnitine or a salt thereof.

In some embodiments, the composition (e.g., an Active Moiety) comprises, consists essentially of, or consists of:
a) the leucine amino acid entity is L-leucine or a salt thereof;
b) the arginine amino acid entity is L-arginine or a salt thereof;
c) the glutamine amino acid entity is L-glutamine or a salt thereof;
d) the NAC entity is NAC or a salt thereof;
e) one or both of the glycine amino acid entity is L-glycine or a salt thereof or the carnitine entity is L-carnitine or a salt thereof;
f) the valine amino acid entity is L-valine or a salt thereof;
g) the histidine amino acid entity is L-histidine or a salt thereof; and
h) the lysine amino acid entity is L-lysine or a salt thereof.

In another aspect, the invention features a composition comprising, consisting essentially of, or consisting of:
a) a leucine amino acid entity,
b) an arginine amino acid entity,
c) a glutamine amino acid entity,
d) a N-acetylcysteine (NAC) entity,
e) a citrulline amino acid entity,
f) a carnitine entity,
g) a serine amino acid entity,
h) a valine amino acid entity,
i) a histidine amino acid entity, and
j) a lysine amino acid entity.

In some embodiments, isoleucine is absent from the composition, or if present, is present at less than: 10 wt. %, 9 wt. %, 8 wt. %, 7 wt. %, 6 wt. %, 5 wt. %, 4 wt. %, 3 wt. %, 2 wt. %, 1 wt. %, 0.5 wt. %, 0.1 wt. %, 0.05 wt. %, 0.01 wt. %, 0.001 wt. %, or less, e.g., of the total wt. of the composition (e.g., in dry form).

In some embodiments, one, two, three, four, five, six, seven, eight, nine, or more (e.g., all) of (a)-(j) is selected from Table 1.

In some embodiments, the composition does not comprise a peptide of more than 20 amino acid residues in length (e.g., whey protein), or if a peptide of more than 20 amino acid residues in length is present, the peptide is present at less than: 10 wt. %, 9 wt. %, 8 wt. %, 7 wt. %, 6 wt. %, 5 wt. %, 4 wt. %, 3 wt. %, 2 wt. %, 1 wt. %, 0.5 wt. %, 0.1 wt. %, 0.05 wt. %, 0.01 wt. %, 0.001 wt. %, or less of the total wt. of the total components of the composition (e.g., in dry form).

In some embodiments, one, two, three, four, five, six, seven, eight, nine, or more (e.g., all) of (a)-(j) are in free amino acid form in the composition, e.g., at least: 42 wt. %, 45 wt. %, 50 wt. %, 55 wt. %, 60 wt. %, 65 wt. %, 70 wt. %, 75 wt. %, 80 wt. %, 85 wt. %, 90 wt. %, 95 wt. %, 97 wt. %, 98 wt. %, or more, of the total wt. of the composition (e.g., in dry form) is one, two, three, four, five, six, seven, eight, nine, or more (e.g., all) of (a)-(j) in free amino acid form in the composition.

In some embodiments, the total wt. % of (a)-(j) is greater than the total wt. % of non-amino acid entity protein components (e.g., whey protein) or non-protein components (or both) in the composition (e.g., in dry form), e.g., (a)-(j) is at least: 50 wt. %, 55 wt. %, 60 wt. %, 65 wt. %, 70 wt. %, 75 wt. %, 80 wt. %, 85 wt. %, 90 wt. %, 95 wt. %, 97 wt. %, 98 wt. %, or more, of the total wt. of the total components in the composition (e.g., in dry form).

In some embodiments, the composition comprises a combination of 18 or fewer, 17 or fewer, 16 or fewer, 15 or fewer, 14 or fewer, 13 or fewer, 12 or fewer, or 11 or fewer amino acid entities.

In some embodiments, the composition (e.g., the Active Moiety) comprises, consists essentially of, or consists of:
a) the leucine amino acid entity is chosen from:
  i) L-leucine or a salt thereof,
  ii) a dipeptide or salt thereof, or tripeptide or salt thereof, comprising L-leucine, or
  iii) β-hydroxy-β-methylbutyrate (HMB) or a salt thereof;
b) the arginine amino acid entity is chosen from:
  i) L-arginine or a salt thereof,
  ii) a dipeptide or salt thereof, or tripeptide or salt thereof, comprising L-arginine,
  iii) creatine or a salt thereof, or
  v) a dipeptide or salt thereof, or tripeptide or salt thereof, comprising creatine;
c) the glutamine amino acid entity is L-glutamine or a salt thereof or a dipeptide or salt thereof, or tripeptide or salt thereof, comprising L-glutamine;
d) the NAC entity is NAC or a salt thereof or a dipeptide or salt thereof comprising NAC;
e) the citrulline amino acid entity is L-citrulline or a salt thereof or a dipeptide or salt thereof, or tripeptide or salt thereof, comprising L-citrulline;
f) the carnitine entity is L-carnitine or a salt thereof, or a dipeptide or salt thereof, comprising L-carnitine;
g) the serine amino acid entity is L-serine or a salt thereof or a dipeptide or salt thereof, or tripeptide or salt thereof, comprising L-serine;
h) the valine amino acid entity is L-valine or a salt thereof or a dipeptide or salt thereof, or tripeptide or salt thereof, comprising L-valine;
i) the histidine amino acid entity is L-histidine or a salt thereof or a dipeptide or salt thereof, or tripeptide or salt thereof, comprising L-histidine; and j) the lysine amino acid entity is L-lysine or a salt thereof or a dipeptide or salt thereof, or tripeptide or salt thereof, comprising L-lysine.

In some embodiments, the composition (e.g., an Active Moiety) comprises, consists essentially of, or consists of:
 a) L-leucine or a salt thereof,
 b) L-arginine or a salt thereof,
 c) L-glutamine or a salt thereof,
 d) NAC or a salt thereof,
 e) L-citrulline or a salt thereof,
 f) L-carnitine or a salt thereof,
 g) L-serine or a salt thereof,
 h) L-valine or a salt thereof,
 i) L-histidine or a salt thereof, and
 j) L-lysine or a salt thereof.

In another aspect, the invention features a method of improving one, two, three, four, five, six, seven, eight, or more (e.g., all) of erythrocyte function, turnover, or synthesis; hemoglobin function, turnover, or synthesis; vascular function; oxidative stress (e.g., one or both of blood or systemic oxidative stress); or inflammation, comprising administering to a subject in need thereof an effective amount of composition (e.g., an Active Moiety) of any of the aspects or embodiments described herein, thereby improving one, two, three, four, five, six, seven, eight, or more (e.g., all) of erythrocyte function, turnover, or synthesis; hemoglobin function, turnover, or synthesis; vascular function, oxidative stress (e.g., one or both of blood or systemic oxidative stress); or inflammation in the subject.

In another aspect, the invention features a method of treating a hemoglobinopathy or a thalassemia, comprising administering to a subject in need thereof an effective amount of a composition (e.g., an Active Moiety) of any of the aspects or embodiments described herein, thereby treating the hemoglobinopathy or the thalassemia in the subject.

In another aspect, the invention features a composition for use in a method of improving one, two, three, four, five, six, seven, eight, or more (e.g., all) of erythrocyte function, turnover, or synthesis; hemoglobin function, turnover, or synthesis; vascular function; oxidative stress (e.g., one or both of blood or systemic oxidative stress); or inflammation, comprising an effective amount of a composition (e.g., an Active Moiety) of any of the aspects or embodiments described herein.

In another aspect, the invention features a composition for use in a method of treating a hemoglobinopathy or a thalassemia, comprising an effective amount of a composition (e.g., an Active Moiety) of any of the aspects or embodiments described herein.

In some embodiments, the subject is at risk of, or has been diagnosed with a hemoglobinopathy (e.g., a β-hemoglobinopathy) or a thalassemia. In certain embodiments, the hemoglobinopathy is a sickle cell disease. In another embodiment, the α-thalassemia is α-thalassemia or β-thalassemia.

In some embodiments, the sickle cell disease is chosen from: sickle cell anemia (HbSS), Hemoglobin SC disease (HbSC), sickle β$^+$-thalassemia (HbS/β+), sickle β$^0$-thalassemia (HbS/β$^0$), hemoglobin SE disease, hemoglobin SD disease, or hemoglobin SO disease.

In some embodiments, administration of the composition results in one, two, three, four, five, six, seven, eight or more (e.g., all) of: a decrease in reactive oxygen species production, a decrease in a level or activity of plasma arginase, an increase in glutathione synthesis, a decrease in erythrocyte adhesion to endothelial and other cells, an increase in erythrocyte resistance to sickling, an increase in erythrocyte calcium influx, an increase in anabolism, an increase in nitric oxide synthesis, or an increase in hemoglobin synthesis.

In some embodiments, administration of the composition results in an improvement in one, two, three, four, or more (e.g., all) of: anemia, hemolysis, vaso-occlusion, ichemia, or pain.

In some embodiments, the composition (an Active Moiety) is formulated with a pharmaceutically acceptable carrier.

In some embodiments, the composition (e.g., the Active Moiety) is formulated as a dietary composition. In some embodiments, the dietary composition is chosen from a medical food, a functional food, or a supplement.

In some embodiments, the composition is a dry blended preparation, e.g., pharmaceutical grade dry blended preparation (PGDBP).

In another aspect, the invention features a method of manufacturing a dry blended preparation, e.g., PGDBP, comprising at least 4 pharmaceutical grade amino acid entities, said method comprising:
 forming a combination of at least 4 pharmaceutical grade amino acid entities and blending the combination for a time sufficient to achieve a dry blended preparation, e.g., PGDBP,
 wherein the dry blended preparation, e.g., PGDBP, comprises: a) a leucine amino acid entity, b) a arginine amino acid entity, c) glutamine amino acid entity; and d) a N-acetylcysteine (NAC)-entity.

In some embodiments, the dry blended preparation, e.g., PGDBP, further comprises one, two, three, four, five, or more (e.g., all) of: e) a citrulline amino acid entity, f) a carnitine entity, g) a serine amino acid entity, h) a valine amino acid entity, i) a histidine amino acid entity, and j) a lysine amino acid entity.

In some embodiments, one, two, or three of: (i) blending occurs at a temperature lower than 40° C.; (ii) blending comprises blending or mixing in a blender or mixer at a speed of less than 1000 rpm; or (iii) the method further comprises performing one, two, or three of direct blending, roller compaction, or wet granulation on the dry blended preparation, e.g., PGDBP.

In another aspect, the invention features a method of manufacturing a dry blended preparation, e.g., PGDBP, comprising at least 4 pharmaceutical grade amino acid entities, said method comprising:
 forming a combination of at least 4 pharmaceutical grade amino acid entities and blending the combination for a time sufficient to achieve a dry blended preparation, e.g., PGDBP,
 wherein the dry blended preparation, e.g., PGDBP, comprises:
 a) a arginine amino acid entity,
 b) a citrulline amino acid entity, and
 c) a N-acetylcysteine (NAC) entity.

In some embodiments, the dry blended preparation, e.g., PGDBP, further comprises one, two, three, four, five, six, or seven of: a) a leucine amino acid entity, b) a glutamine amino acid entity, c) a carnitine entity, d) a serine amino acid entity, e) a valine amino acid entity, f) a histidine amino acid entity, and g) a lysine amino acid entity.

In another aspect, the invention features a composition comprising:
 a) an arginine amino acid entity,
 b) a citrulline amino acid entity; and
 c) a N-acetylcysteine (NAC)-entity,
 wherein one, two, or three of:
 (i) the composition does not comprise a peptide of more than 20 amino acid residues in length (e.g., whey protein), or if a peptide of more than 20 amino acid residues in length is present, the peptide is present at less than: 10 wt. % of the total wt. of the composition (e.g., in dry form);

(ii) at least 50 wt. % of the total wt. of the composition (e.g., in dry form) is one or more amino acid entities in free form; or (iii) the wt. % of the citrulline amino acid entity is greater than the wt. % of the NAC-entity.

In some embodiments, the composition has one, two, or three of the following features:

(i) the wt. % of the citrulline amino acid entity in the composition (e.g., in dry form) is at least 50% greater than the wt. % of the NAC-entity, e.g., the wt. % of the citrulline amino acid entity is at least 60%, 65%, 70%, 75%, or 80% greater than the wt. % of the NAC-entity;

(ii) the wt. % of the leucine amino acid entity, the citrulline amino acid entity, and the NAC entity is at least: 20 wt. %, 25 wt. %, 30 wt. %, or 35 wt. % of the amino acid entity components or total components in the composition (e.g., in dry form), but not more than 80 wt. % of the amino acid entity componentsor total components in the composition (e.g., in dry form); or (iii) the wt. % of the citrulline amino acid entity is at least: 5 wt. %, 10 wt. %, 11 wt. %, 12 wt. %, 13 wt. %, or more of the amino acid entity components in the composition (e.g., in dry form), but not more than 60 wt. % of the amino acid entity components in the composition (e.g., in dry form).

In some embodiments, the composition further comprises one or both of: (d) a carnitine amino acid entity; or (e) a glutamine amino acid entity.

In some embodiments, the composition comprises:
a) the arginine amino acid entity is chosen from:
  i) L-arginine or a salt thereof,
  ii) a dipeptide or salt thereof, or tripeptide or salt thereof, comprising L-arginine,
  iii) creatine or a salt thereof, or
  v) a dipeptide or salt thereof, or tripeptide or salt thereof, comprising creatine;
b) the citrulline amino acid entity is L-citrulline or a salt thereof or a dipeptide or salt thereof, or tripeptide or salt thereof, comprising L-citrulline; and
c) the NAC entity is NAC or a salt thereof or a dipeptide or salt thereof comprising NAC.

In another aspect, the invention features a composition comprising:
a) an arginine amino acid entity,
b) a citrulline amino acid entity;
c) a N-acetylcysteine (NAC)-entity;
d) a carnitine amino acid entity; and
e) a glutamine amino acid entity,
wherein one, two, or three of:
(i) the composition does not comprise a peptide of more than 20 amino acid residues in length (e.g., whey protein), or if a peptide of more than 20 amino acid residues in length is present, the peptide is present at less than: 10 wt. % of the total wt. of the composition (e.g., in dry form);

(ii) at least 50 wt. % of the total wt. of the composition (e.g., in dry form) is one or more amino acid entities in free form; or (iii) the wt. % of the citrulline amino acid entity is greater than the wt. % of the NAC-entity.

In some embodiments, the composition has one, two, three, or four of the following features:

(i) the wt. % of the leucine amino acid entity, the citrulline amino acid entity, the NAC entity, the carnitine amino acid entity, and the glutamine amino acid entity is at least: 40 wt. %, 45 wt. %, 50 wt. %, 55 wt. %, or 60 wt. % of the amino acid entity components or total components in the composition (e.g., in dry form), but not more than 90 wt. % of the amino acid entity components or total components in the composition (e.g., in dry form);

(ii) the wt. % of the citrulline amino acid entity in the composition (e.g., in dry form) is greater than the wt. % of the carnitine amino acid entity, e.g., the wt. % of the citrulline amino acid entity in the composition (e.g., in dry form) is at least 50% greater than the wt. % of the carnitine amino acid entity, e.g., the wt. % of the citrulline amino acid entity is at least 60%, 65%, 70%, 75%, or 80% greater than the wt. % of the carnitine amino acid entity;

(iii) the wt. % of the glutamine amino acid entity in the composition (e.g., in dry form) is greater than the wt. % of the citrulline amino acid entity, e.g., the wt. % of the glutamine amino acid entity in the composition (e.g., in dry form) is at least 40% greater than the wt. % of the citrulline amino acid entity, e.g., the wt. % of the glutamine amino acid entity is at least 60%, 45%, 50%, 55%, 60%, or 65% greater than the wt. % of the citrulline amino acid entity; or (iv) the wt. % of the citrulline amino acid entity and the arginine amino acid entity in combination in the composition (e.g., in dry form) is greater than the wt. % of the glutamine amino acid entity, e.g., the wt. % of the citrulline amino acid entity in the composition (e.g., in dry form) is at least 20% greater than the wt. % of the carnitine amino acid entity, e.g., the wt. % of the citrulline amino acid entity is at least 30%, 35%, 40%, 45%, or 50% greater than the wt. % of the carnitine amino acid entity.

In some embodiments, the composition further comprises one, two, or three of: (f) a leucine amino acid entity, (g) a serine amino acid entity, (h) a valine amino acid entity, (i) a histidine amino acid entity, or (j) a lysine amino acid entity.

In some embodiments, the composition comprises:
a) the arginine amino acid entity is chosen from:
  i) L-arginine or a salt thereof,
  ii) a dipeptide or salt thereof, or tripeptide or salt thereof, comprising L-arginine,
  iii) creatine or a salt thereof, or
  v) a dipeptide or salt thereof, or tripeptide or salt thereof, comprising creatine;
b) the citrulline amino acid entity is L-citrulline or a salt thereof or a dipeptide or salt thereof, or tripeptide or salt thereof, comprising L-citrulline; and
c) the NAC entity is NAC or a salt thereof or a dipeptide or salt thereof comprising NAC;
d) the carnitine entity is L-carnitine or a salt thereof, or a dipeptide or salt thereof, comprising L-carnitine; and
e) the glutamine amino acid entity is L-glutamine or a salt thereof or a dipeptide or salt thereof, or tripeptide or salt thereof, comprising L-glutamine.

DETAILED DESCRIPTION

Figure 1:
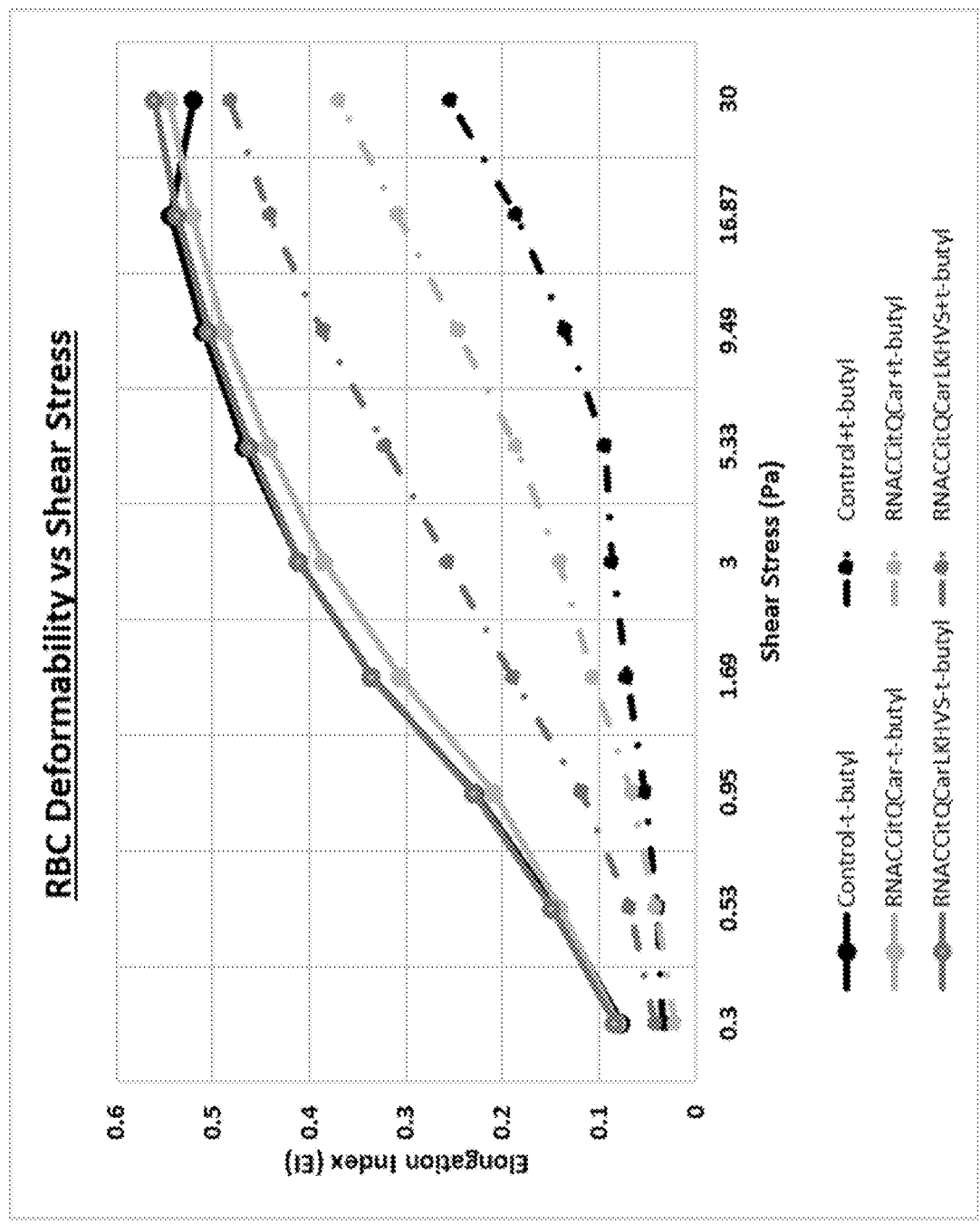
FIG. 1 shows a RBC deformability profile following ex vivo oxidation of whole blood (donor 1) with and without tert-butyl hydroperoxide and pre-treatment with vehicle or amino acids.

Physical and metabolic dysfunction of red blood cells (RBC) drive acute and chronic complications in nearly every organ system, such as in a hemoglobinopathy (e.g., sickle cell disease) or a thalassemia (e.g. α-thalassemia or β-thalassemia). RBC dysfunction and lysis drive myriad clinical sequelae such as vaso-occlusion, organ failure, and infections. RBC dysfunction can be characterized by cell sickling, oxidative stress, dehydration, and adhesion to endothelium, which may complicate the passage of RBC through microvessels. Chronic complications can stem from a lifetime of anemia and accrual of organ damage into adulthood, and can be punctuated by acute events such as vaso-occlusion and sudden organ failure.

Sickle cell disease (SCD) describes a group of serious blood disorders that affect some 85,000 adults and 15,000 children in the US, and 4.4 million individuals worldwide. The sickle-shaped red blood cells that are the hallmark of SCD reveal only a small fraction of the complex and multifactorial pathophysiology stemming from perturbations in the normal function of blood and the vascular system. Current care is limited both in scope and magnitude of effect, leaving an unmet need for agents that help to mitigate the multifaceted complications arising from blood and vascular dysfunction.

The compositions of the invention are designed to target multiple pathways (blood production and integrity, vascular function, and plasma and RBC amino acid imbalances) intersecting key systems (vascular, RBCs) to maintain blood health and function.

The amino acid entities and relative amounts of the amino acid entities in the compositions disclosed herein have been optimized, e.g., to [1] reduce vascular adhesion, [2] mitigate the presentation of vascular inflammation, [3] defend against insults to red blood cell (RBC) deformability and function, and reduce complications associated with SCD (e.g., hemolysis, vascular adhesion, vascular inflammation, reduced vascular function, acute and chronic organ failure) in a subject that requires the coordination of many biological, cellular and molecular processes. Without being bound by any theory, it is understood that a composition of the invention can reprogram the disordered multifactorial biology of [1] RBC rigidity and fragility, [2] hemolysis, [3] vascular adhesion, [4] vascular inflammation, and [5] vascular dysfunction.

The composition described herein provides a multimodal and combinatorial approach to improve red blood cell dysfunction, hemolysis (e.g., including anemia, chronic hypoxia, oxidative stress, depletion of nitric oxide, and/or vascular dysfunction), vaso-occlusion (e.g., including ischemic injury, inflammation, clotting, and/or acute organ damage), altered hematopoiesis, and/or sickle cell disease pathophysiology. In some embodiments, administration of the composition results in improved vascular tone, vascular dilation, and/or vaso-occlusion (e.g. improved NO availability, NO-dependent endothelial function, and/or blood pressure). In some embodiments, administration of the composition results in improved RBC deformability, reduced hemolysis, and/or reduced vascular inflammation (e.g., as determined by levels of glutathione (e.g., plasma or RBC glutathione), oxidative stress markers, hemolytic markers, cytokines, and/or adhesion markers). In some embodiments, administration of the composition results in increased protein synthesis and/or increased proteogenic substrates for hemoglobin to support heme synthesis. In some embodiments, administration of the composition results in improved hematopoiesis and/or an improved red blood cell population (e.g. improved reticulocytes, hemoglobin, fetal hemoglobin, and/or dense or irreversibly sickled cells). The composition described herein is optimized to target one, two, or three of: (i) restoration of plasma arginine and nitric oxide to improve vascular injury; (ii) improved antioxidant defense in red blood cells, plasma, and systems-wide; or (iii) anabolic and energetic support for increased hematopoietic demand, in a subject, e.g., a subject having a hemoglobinopathy (e.g., sickle cell disease) or a thalassemia (e.g. α-thalassemia or β-thalassemia).

In some embodiments, the composition (e.g., the Active Moiety) is capable of improving one, two, three, four, or more (e.g., all) of NO-mediated vascular function, protein synthesis, cellular energy, inflammation, or heme synthesis. In some embodiments, the composition is capable of restoring NO-dependent endothelial function, reducing risk of vaso-occlusion events, improving vascular health, decreasing hemolysis, and/or decreasing oxidative stress. In some embodiments, the composition is capable of providing increased arginine bioavailability for NO synthesis. In some embodiments, the composition is capable of increasing RBC turnover, protein synthesis (e.g., hemoglobin synthesis, e.g., in hematopoietic progenitors and/or reticulocytes), and/or heme synthesis. In some embodiments, the composition is capable of providing energetic support for highly proliferative cells (e.g., hematopoietic precursors and/or immune cells).

Described herein, in part, is a composition (an Active Moiety) comprising amino acid entities and methods of improving one, two, three, four, five, six, seven, eight or more (e.g., all) of erythrocyte function, turnover, or synthesis; hemoglobin function, turnover, or synthesis; vascular function; oxidative stress (e.g., one or both of blood and systemic oxidative stress); or inflammation by administering an effective amount of the composition. The composition may be administered to treat a hemoglobinopathy (e.g., sickle cell disease) or a thalassemia (e.g. α-thalassemia or β-thalassemia) in a subject in need thereof. The amino acid entities and relative amounts of the amino acid entities in the composition have been carefully selected, e.g., to improve erythrocyte and/or hemoglobin function, turnover, or synthesis in a subject (e.g., a subject having a hemoglobinopathy (e.g., SCD) or a thalassemia) that requires the coordination of many biological, cellular, and molecular processes. The composition allows for multi-pathway beneficial effects on the systems-level pathology of a hemoglobinopathy or a thalassemia. In particular, the composition has been specifically tailored to treat oxidative stress, vascular disease, inflammation, and the increased turnover, synthesis, and dysfunction of erythrocytes and hemoglobin.

Complex diseases, such as hemoglobinopathy (e.g., sickle cell disease) or thalassemia (e.g. α-thalassemia or β-thalassemia), impact multiple biological pathways. Loss of health can be the direct result of metabolic pathways and functions that are not being maintained or supported. Consequently, restoring homeostasis and maintaining health requires multifactorial approaches. The compositions described herein are interventional candidates to address the systems-wide impact of dysregulated metabolism to support and maintain homeostasis, which helps support normal structures and functions of the body.

The composition described herein have been optimized to directly and simultaneously target multiple metabolic pathways implicated both in complex diseases (e.g., a subject having a hemoglobinopathy (e.g., SCD) or a thalassemia) and overall health. The distinct ratios of each of the amino acid entities in the composition are designed to target and maximize the fundamental role of the composition in regulating multiple metabolic functions (e.g., one, two, three, four, five, six, seven, eight or more (e.g., all) of erythrocyte function, turnover, or synthesis; hemoglobin function, turnover, or synthesis; vascular function; oxidative stress (e.g., one or both of blood and systemic oxidative stress). In particular, the composition described herein can support and maintain blood health, which is critical to a multitude of metabolic functions throughout the body. The composition described herein has been designed to target multiple biological pathways with the goal of supporting normal structures and functions of the blood. In particular, administration of the composition described herein can improve and/or treat one, two, three, or more of reduced blood production, reduced blood integrity, plasma and/or RBC amino acid imbalance, decreased vascular health, or inflammation, e.g., in a subject with a hemoglobinopathy (e.g., sickle cell disease) or a thalassemia (e.g. α-thalassemia or β-thalassemia). In some embodiments, administration of the composition to a subject improves or maintains one, two, three, four, five, six, seven, eight, or more of the following: (a) proliferation and/or maturation of blood cells during hematopoietic demand; (b) RBC form and/or function against dehydration; (c) rigidity; (d) oxygen transport; (e) amino acid balance to support RBC metabolism (e.g., substrates for glutathione and nitric oxide synthesis); (f) generation of ROS; (g) delivery of amino acids to peripheral tissue; (h) defenses against vascular adhesion; (i) inflammation; or (j) stasis.

Definitions

Terms used in the claims and specification are defined as set forth below unless otherwise specified.

It must be noted that, as used in the specification and the appended claims, the singular forms "a," "an" and "the" include plural referents unless the context clearly dictates otherwise.

As used herein, the term "amino acid entity" refers to a levo (L)-amino acid in free form or salt form (or both), the L-amino acid residue in a peptide smaller than 20 amino acid residues (e.g., oligopeptide, e.g., a dipeptide or a tripeptide), a derivative of the amino acid, a precursor of the amino acid, or a metabolite of the amino acid (see, e.g., Table 1). An amino acid entity includes a derivative of the amino acid, a precursor of the amino acid, a metabolite of the amino acid, or a salt form of the amino acid that is capable of effecting biological functionality of the free L-amino acid. An amino acid entity does not include a naturally occurring polypeptide or protein of greater than 20 amino acid residues, either in whole or modified form, e.g., hydrolyzed form.

Salts of amino acids include any ingestible salt. For pharmaceutical compositions, the salt form of an amino acid present in the composition (e.g., the Active Moiety) should be a pharmaceutically acceptable salt. In a specific example, the salt form is the hydrochloride (HCl) salt form of the amino acid.

In some embodiments, the derivative of an amino acid entity comprises an amino acid ester (e.g., an alkyl ester, e.g., an ethyl ester or a methyl ester of an amino acid entity) or a keto-acid.

TABLE 1

Amino acid entities include amino acids, precursors, metabolites, and derivatives of the compositions described herein.

|  | Exemplary Amino Acid | Precursors | Metabolites | Derivatives |
|---|---|---|---|---|
| Leucine | L-Leucine | Oxo-leucine | HMB (beta-hydroxy-beta-methybutyrate); Oxo-leucine; Isovaleryl-CoA | N-Acetyl-Leucine |
| Arginine | L-Arginine | Argininosuccinate; Aspartate; Glutamate | Agmatine; Creatine | N-Acetyl-Arginine |
| Glutamine | L-Glutamine | Glutamate | Glutamate | N-Acetyl-Glutamine |
| NAC | N-Acetylcysteine | Serine; Acetylserine; Cystathionine | Glutathione; Cystathionine; Homocysteine; Methionine | Cystine; Cysteamine |
| Citrulline | L-Citrulline | - N-hydroxyl-arginine | Argininosuccinate, Nitric oxide |  |
| Carnitine | L-Carnitine | 6-N-trimethyllysine; N6-Trimethyl-3-OH-lysine |  | Acetyl-L-Carnitine (ALCAR); Proprionyl-L-Carnitine (PLCAR); L-Carnitine L-Tartrate |
| Serine | L-Serine | Phosphoserine, P-hydroxypyruvate, L-Glycine | Glycine, Tryptophan, Acetylserine, Cystathionine, Phosphatidylserine |  |

TABLE 1-continued

Amino acid entities include amino acids, precursors, metabolites, and derivatives of the compositions described herein.

| | Exemplary Amino Acid | Precursors | Metabolites | Derivatives |
|---|---|---|---|---|
| Valine | L-Valine | 2-Oxo-valerate | Isobutryl-CoA | N-Acetyl-Valine |
| Histidine | L-Histidine | Histidinol; Histidinal; Ribose-5-phosphate | Carnosine; Histamine; Urocanate | N-Acetyl-Histidine |
| Lysine | L-Lysine | Diaminopimelate; Aspartate | Trimethyllysine; Saccharopine | N-Acetyl-Lysine |
| Glycine | L-Glycine | Serine, Sarcosine, Betaine, Dimethyglycine, | Glutathione, Serine, Creatine | |

"About" and "approximately" shall generally mean an acceptable degree of error for the quantity measured given the nature or precision of the measurements. Exemplary degrees of error are within 15 percent (%), typically, within 10%, and more typically, within 5% of a given value or range of values.

An "amino acid" refers to an organic compound having an amino group (—$NH_2$), a carboxylic acid group (—C(=O)OH), and a side chain bonded through a central carbon atom, and includes essential and non-essential amino acids and natural, non-proteinogenic, and unnatural amino acids.

As used herein, the term "Active Moiety" means a combination of two or more amino acid entities that, in aggregate, have the ability to have a biological or therapeutic effect as described herein, e.g., an effect on erythrocyte function, turnover, or synthesis; hemoglobin function, turnover, or synthesis; or vascular function. For example, an Active Moiety can rebalance a metabolic dysfunction in a subject suffering from a disease or disorder. An Active Moiety of the invention can contain other biologically active ingredients. In some examples, the Active Moiety comprises a defined combination of four or more amino acid entities, as set out in detail below. In other embodiments, the Active Moiety consists of a defined combination of amino acid entities, as set out in detail below.

The individual amino acid entities are present in the composition, e.g., Active Moiety, in various amounts or ratios, which can be presented as amount by weight (e.g., in grams), ratio by weight of amino acid entities to each other, amount by mole, amount by weight percent of the composition, amount by mole percent of the composition, caloric content, percent caloric contribution to the composition, etc. Generally this disclosure will provide grams of amino acid entity in a dosage form, weight percent of an amino acid entity relative to the weight of the composition, i.e., the weight of all the amino acid entities and any other biologically active ingredient present in the composition, or in ratios. In some embodiments, the composition, e.g., Active Moiety, is provided as a pharmaceutically acceptable preparation (e.g., a pharmaceutical product).

The term "effective amount" as used herein means an amount of an active of the invention in a composition of the invention, particularly a pharmaceutical composition of the invention, which is sufficient to reduce a symptom and/or improve a condition to be treated (e.g., provide a desired clinical response). The effective amount of an active for use in a composition will vary with the particular condition being treated, the severity of the condition, the duration of treatment, the nature of concurrent therapy, the particular active being employed, the particular pharmaceutically-acceptable excipient(s) and/or carrier(s) utilized, and like factors with the knowledge and expertise of the attending physician.

A "pharmaceutical composition" described herein comprises at least one "Active Moiety" and a pharmaceutically acceptable carrier or excipient. In some embodiments, the pharmaceutical composition is used as a therapeutic. Other compositions, which need not meet pharmaceutical standards (GMP; pharmaceutical grade components) can be used as a nutraceutical, a medical food, or as a supplement, these are termed "consumer health compositions".

The term "pharmaceutically acceptable" as used herein, refers to amino acids, materials, excipients, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In a specific embodiment, "pharmaceutically acceptable" means free of detectable endotoxin or endotoxin levels are below levels acceptable in pharmaceutical products.

In a specific embodiment, "pharmaceutically acceptable" means a standard used by the pharmaceutical industry or by agencies or entities (e.g., government or trade agencies or entities) regulating the pharmaceutical industry to ensure one or more product quality parameters are within acceptable ranges for a medicine, pharmaceutical composition, treatment, or other therapeutic. A product quality parameter can be any parameter regulated by the pharmaceutical industry or by agencies or entities, e.g., government or trade agencies or entities, including but not limited to composition; composition uniformity; dosage; dosage uniformity; presence, absence, and/or level of contaminants or impurities; and level of sterility (e.g., the presence, absence and/or level of microbes). Exemplary government regulatory agencies include: Federal Drug Administration (FDA), European Medicines Agency (EMA), SwissMedic, China Food and Drug Administration (CFDA), or Japanese Pharmaceuticals and Medical Devices Agency (PMDA).

The term "pharmaceutically acceptable excipient" refers to an ingredient in a pharmaceutical formulation, other than an active, which is physiologically compatible. A pharmaceutically acceptable excipient can include, but is not limited to, a buffer, a sweetener, a dispersion enhancer, a flavoring agent, a bitterness masking agent, a natural coloring, an artificial coloring, a stabilizer, a solvent, or a preservative. In a specific embodiment, a pharmaceutically acceptable excipient includes one or both of citric acid or lecithin.

The term "non-amino acid entity protein component," as used herein, refers to a peptide (e.g., a polypeptide or an oligopeptide), a fragment thereof, or a degraded peptide. Exemplary non-amino acid entity protein components include, but are not limited to, one or more of whey protein, egg white protein, soy protein, casein, hemp protein, pea protein, brown rice protein, or a fragment or degraded peptide thereof.

The term "non-protein component," as used herein, refers to any component of a composition other than a protein component. Exemplary non-protein components can include, but are not limited to, a saccharide (e.g., a monosaccharide (e.g., dextrose, glucose, or fructose), a disaccharide, an oligosaccharide, or a polysaccharide); a lipid (e.g., a sulfur-containing lipid (e.g., alpha-lipoic acid), a long chain triglyceride, an omega 3 fatty acid (e.g., EPA, DHA, STA, DPA, or ALA), an omega 6 fatty acid (GLA, DGLA, or LA), a medium chain triglyceride, or a medium chain fatty acid); a vitamin (e.g., vitamin A, vitamin E, vitamin C, vitamin D, vitamin B6, vitamin B12, biotin, or pantothenic acid); a mineral (zinc, selenium, iron, copper, folate, phosphorous, potassium, manganese, chromium, calcium, or magnesium); or a sterol (e.g., cholesterol).

A composition, formulation or product is "therapeutic" if it provides a desired clinical effect. A desired clinical effect can be shown by lessening the progression of a disease and/or alleviating one or more symptoms of the disease.

A "unit dose" or "unit dosage" comprises the drug product or drug products in the form in which they are marketed for use, with a specific mixture of the active and inactive components (excipients), in a particular configuration (e.g, a capsule shell, for example), and apportioned into a particular dose (e.g., in multiple stick packs).

As used herein, the terms "treat," "treating," or "treatment" of a hemoglobinopathy (e.g., sickle cell disease) or a thalassemia refers to ameliorating a hemoglobinopathy or a thalassemia (e.g., slowing, arresting, or reducing the development of a hemoglobinopathy or a thalassemia or at least one of the clinical symptoms thereof); alleviating or ameliorating at least one physical parameter including those which may not be discernible by the patient; and/or preventing or delaying the onset or development or progression of a hemoglobinopathy (e.g., sickle cell disease) or a thalassemia.

A "time sufficient" or "sufficient time" as used herein in the context of blending means a time sufficient to achieve blend and composition uniformity without generating impurities or inducing heterogeneity.

A dry blended preparation, e.g., PGDBP, described herein may be formulated as a "pharmaceutical composition". A pharmaceutical composition as described herein comprises at least one amino acid entity, e.g., an Active Moiety, and a pharmaceutically acceptable carrier or excipient. In some embodiments, the pharmaceutical composition is used as a therapeutic or a medical food. In some embodiments, the pharmaceutical composition is used as a nutriceutical or as a supplement.

The term "pharmaceutical grade" as used herein, refers to amino acids, materials, excipients, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments, pharmaceutical grade means that the amino acids, materials, or excipients meet the specifications of a monograph, e.g., a monograph of the United States Pharmacopeia (USP), the National Formulary (NF), British Pharmacopeia (BP), European Pharmacopeia (EP), or Japanese Pharmacopeia (JP) detailing tests and acceptance criteria. In some embodiments, the meaning of pharmaceutical grade comprises that the amino acids, excipients, or materials are at least 99% pure.

A dry blended preparation, as used herein, means a combination of a plurality of amino acid entities that substantially lacks water. In some embodiments, a dry blended preparation is a powder. In some embodiments, a dry blended preparation comprises less than or equal to 10, 9, 8, 7, 6, 5, 4, 3, 2, or 1% water by weight. In some embodiments, a dry blended preparation comprises at least 4 amino acid entities, e.g., 4, 5, 6, 7, 8, 9, 10, 11, 12, 13, 14, 15, 16, 17, 18, 19, or 20 amino acid entities.

A pharmaceutical grade dry blended preparation (PGDBP), as used herein, is a dry blended preparation that meets a reference standard (e.g., one or more reference standards) and comprises a plurality of pharmaceutical grade amino acid entities. A PGDBP may be formulated as a pharmaceutical composition, e.g., the PGDBP may further comprise one or more excipients and/or oral administration components. In some embodiments, a reference standard met by a PGDBP is composition uniformity.

Composition uniformity, as used herein, is a standard for the homogeneity of a component of a combination, e.g., a dry blended preparation, e.g., a PGDBP, that comprises blend uniformity, portion uniformity, or both. In some embodiments, a combination meets a standard for composition uniformity, e.g., blend uniformity, if the amount of a component (e.g., a pharmaceutical grade amino acid entity, excipient, or oral administration component) at a sampling point in the combination differs from a reference value by less than a predetermined amount. In some embodiments, the reference value is the amount of the component at a second sampling point in the combination. In some embodiments, the reference value is the amount of the component (e.g., a pharmaceutical grade amino acid entity, excipient, or oral administration component) present in the combination (e.g., a dry blended preparation, e.g., a PGDBP).

In some embodiments, wherein a combination (e.g., a dry blended preparation, e.g., a PGDBP) is divided into portions, the portions of the combination meet a standard for composition uniformity, e.g., portion uniformity, if the amount of a component (e.g., a pharmaceutical grade amino acid entity, excipient, or oral administration component) in a portion differs from a reference value by less than a predetermined amount. In some embodiments, the reference value is the amount of the component in a second portion. In some embodiments, the reference value comprises the amount of the component in a N additional portions, wherein in is at least 2, 3, 4, 5, 6, 7, 8, 9, 10, 20, 30, 40, 50, 60, 70, 80, 90, or 100. In some embodiments, the reference value is the amount of the component (e.g., a pharmaceutical grade amino acid entity, excipient, or oral administration component) present in the combination (e.g., a dry blended preparation, e.g., a PGDBP). Amounts may be absolute (e.g., mass or weight) or relative (e.g., percent of total components). In some embodiments, the predetermined amount may be 20, 19, 18, 17, 16, 15, 14, 13, 12, 11, 10, 9, 8, 7, 6, 5, 4, 3, 2, or 1%, e.g., of the reference value. In some embodiments, the predetermined amount is 10% (e.g., the amount of the component differs from the reference value by less than 10%).

Portioning, as used herein, means dividing all or part of the dry blended preparation, e.g., PGDBP, into portions for administration to a patient or subject. The portions created by portioning may be provided in sachets, vials, or other containers, e.g., stick packs. In one embodiment, the portions created by portioning are unit dosage amounts, e.g., one unit dosage or a fraction of a unit dosage (e.g., a stick pack may comprise half a unit dose, such that two stick packs would be used together to provide a single unit dose). In some embodiments, only PGDBPs (e.g., that meet a reference standard) are separated into portions via portioning. In some embodiments, portions generated by portioning also meet a reference standard.

Compositions comprising Amino Acid Entities (e.g., Active Moieties)

The composition of the invention as described herein (an Active Moiety) comprises amino acid entities, e.g., the amino acid entities shown in Table 1. In some embodiments, the composition comprises: a) a leucine amino acid entity, b) a arginine amino acid entity, c) glutamine amino acid entity; d) a N-acetylcysteine (NAC) entity; and e) a glycine amino acid entity. In some embodiments, the composition comprises: a) a leucine amino acid entity, b) a arginine amino acid entity, c) glutamine amino acid entity; d) a NAC entity; and e) a carnitine entity. In some embodiments, the composition comprises: a) a leucine amino acid entity, b) a arginine amino acid entity, c) glutamine amino acid entity; d) a NAC entity; and e) a glycine amino acid entity and a carnitine entity. In some embodiments, the composition further comprises one, two, or more (e.g., all) of (f) a valine amino acid entity, (g) a histidine amino acid entity, or (h) a lysine amino acid entity.

In some embodiments, the composition comprises: (a) one or both of a citrulline amino acid entity or an arginine amino acid entity, and (b) a NAC entity. In some embodiments, the composition further comprises one or both of a carnitine entity or a glutamine amino acid entity. In some embodiments, the composition further comprises one, two, three, four, or more (e.g., all) of a leucine amino acid entity, a histidine amino acid entity, a lysine amino acid entity, a valine amino acid entity, or a serine amino acid entity.

In certain embodiments, the leucine amino acid entity is chosen from L-leucine, β-hydroxy-β-methylbutyrate (HMB), oxo-leucine (α-ketoisocaproate (KIC)), isovaleryl-CoA, n-acetyl-leucine, or a combination thereof.

In certain embodiments, the arginine amino acid entity is chosen from L-arginine, creatine, argininosuccinate, aspartate, glutamate, agmatine, N-acetyl-arginine, or a combination thereof.

In certain embodiments, the glutamine amino acid entity is chosen from L-glutamine, glutamate, carbamoyl-P, n-acetylglutamine, or a combination thereof.

In certain embodiments, the NAC-amino acid entity is chosen from NAC, serine, acetylserine, cystathionine, homocysteine, glutathione, or a combination thereof.

In certain embodiments, the citrulline amino acid entity is chosen from L-citrulline, ornithine, carbamoyl-P, carbamoyl-P and ornithine, N-hydroxyl-arginine, argininosuccinate, nitric oxide, or a combination thereof.

In certain embodiments, the carnitine entity is chosen from L-carnitine, 6-N-trimethyllysine, N6-trimethyl-3-OH-lysine, acetyl-L-carnitine, proprionyl-L-carnitine, L-carnitine L-tartrate, or a combination thereof.

In certain embodiments, the serine amino acid entity is chosen from L-serine, phosphoserine, p-hydroxypyruvate, L-glycine, acetylserine, cystathionine, phosphatidylserine, or a combination thereof.

In certain embodiments, the glycine amino acid entity is chosen from L-glycine, L-serine, sarcosine, betaine, dimethylglycine, glutathione, creatine, or a combination thereof.

In certain embodiments, the valine amino acid entity is chosen from L-valine, 2-oxo-valerate, isobutryl-CoA, N-acetyl-valine, or a combination thereof.

In certain embodiments, the histidine amino acid entity is chosen from L-histidine, histidinol, histidinal, ribose-5-phosphate, carnosine, histamine, urocanate, N-acetyl-histidine, or a combination thereof.

In certain embodiments, the lysine amino acid entity is chosen from L-lysine, diaminopimelate, aspartate, trimethyllysine, saccharopine, N-acetyl-lysine, or a combination thereof.

In some embodiments, one, two, three, four, five, six, seven, or more (e.g., all) of (a)-(h) are in free amino acid form in the composition, e.g., at least: 42 wt. %, 75 wt. %, or 90 wt. % of the total wt. of amino acid entity componentsor total components is one, two, three, four, five, six, seven, or more (e.g., all) of (a)-(h) in free amino acid form in the composition (e.g., in dry form).

In some embodiments, one, two, three, four, five, six, seven, or more (e.g., all) of (a)-(h) are in salt form in the composition, e.g., at least: 0.01 wt. %, 0.1 wt. %, 0.5 wt. %, 1 wt. %, 5 wt. %, or 10 wt. %, or more of the total wt. of amino acid entity componentsor total components is one, two, three, four, five, or more (e.g., all) of (a)-(f) in salt form in the composition.

In some embodiments, one, two, three, four, five, six, seven, or more (e.g., all) of (a)-(h) is provided as part of a dipeptide or tripeptide, e.g., in an amount of at least: 0.01 wt. %, 0.1 wt. %, 0.5 wt. %, 1 wt. %, 5 wt. %, or 10 wt. %, or more of amino acid entity components or total components of the composition.

In some embodiments, one, two, three, four, five, six, seven, eight, nine, or more (e.g., all) of (a)-(j) are in free amino acid form in the composition, e.g., at least: 42 wt. %, 45 wt. %, 50 wt. %, 55 wt. %, 60 wt. %, 65 wt. %, 70 wt. %, 75 wt. %, 80 wt. %, 85 wt. %, 90 wt. %, 95 wt. %, 97 wt. %, 98 wt. %, or more, of the total wt. of the composition (e.g., in dry form) is one, two, three, four, five, six, seven, eight, nine, or more (e.g., all) of (a)-(j) in free amino acid form in the composition.

In some embodiments, one, two, three, four, five, six, seven, eight, nine, or more (e.g., all) of (a)-(j) are in salt form in the composition, e.g., at least: 0.01 wt. %, 0.1 wt. %, 0.5 wt. %, 1 wt. %, 2 wt. %, 3 wt. %, 4 wt. %, 5 wt. %, 6 wt. %, 7 wt. %, 8 wt. %, 9 wt. %, or 10 wt. %, or more, of the total wt. of the composition (e.g., in dry form) is one, two, three, four, five, six, seven, eight, nine, or more (e.g., all) of (a)-(j) in salt form in the composition.

In some embodiments, one, two, three, four, five, six, seven, eight, nine, or more (e.g., all) of (a)-(j) is provided as part of a dipeptide or tripeptide, e.g., in an amount of at least: 0.01 wt. %, 0.1 wt. %, 0.5 wt. %, 1 wt. %, 2 wt. %, 3 wt. %, 4 wt. %, 5 wt. %, 6 wt. %, 7 wt. %, 8 wt. %, 9 wt. %, or 10 wt. %, or more, or more of amino acid entity components or total components of the composition.

In certain embodiments, the composition (e.g., the Active Moiety) is capable of decreasing, or decreases, inflammation by at least 60%, 75%, or 90%, as detected using an assay of IL-6, e.g., in macrophage cells, e.g., using an antibody-based detection assay, e.g., an ELISA, e.g., as described in Example 1, e.g., relative to a reference composition (e.g., a vehicle control; an amino acid composition comprising L-leucine, L-isoleucine, L-valine; an amino acid composition comprising L-leucine, L-isoleucine, L-valine, L-arginine, and L-glutamine; L-arginine alone; L-glutamine alone; L-leucine alone; or L-valine alone).

In certain embodiments, the composition (e.g., the Active Moiety) is capable of decreasing, or decreases, inflammation by at least 60%, 75%, or 90%, as detected using an assay of TNFα, e.g., in macrophage cells, e.g., using an antibody-based detection assay, e.g., an ELISA, e.g., as described in Example 1, e.g., relative to a reference composition (e.g., a vehicle control; an amino acid composition comprising L-leucine, L-isoleucine, L-valine; an amino acid composition comprising L-arginine, L-glutamine, and NAC; an amino acid composition comprising L-leucine, L-isoleucine, L-valine, L-arginine, and L-glutamine; valine; glutamine; arginine; isoleucine; leucine; or NAC).

i. Amounts

An exemplary composition (e.g., an Active Moiety) can include 1.2 g of an leucine amino acid entity; 1.5 g of an arginine amino acid entity; 3.67 g of a glutamine amino acid entity; 0.4 g of a NAC entity; 0.33 g of a carnitine entity; 0.9 g of a glycine amino acid entity; 0.6 g of a valine amino acid entity; 0.6 g of a histidine amino acid entity; and 0.6 g of a lysine amino acid entity (see, e.g., g/dose in Table 2). An exemplary composition can include 0.6 g of an leucine amino acid entity; 0.75 g of an arginine amino acid entity; 1.83 g of a glutamine amino acid entity; 0.2 g of a NAC entity; 0.17 g of a carnitine entity; 0.45 g of a glycine amino acid entity; 0.3 g of a valine amino acid entity; 0.3 g of a histidine amino acid entity; and 0.3 g of a lysine amino acid entity

TABLE 2

Exemplary composition comprising amino acids (e.g., an Active Moiety).

| Amino Acid | Dose (g) | Total Daily | Wt. Ratio | Wt. % |
|---|---|---|---|---|
| L-leucine | 3.6 | 7.2 | 3.6 | 12.24 |
| L-arginine | 4.5 | 9 | 4.5 | 15.31 |
| L-glutamine | 11 | 22 | 11 | 37.41 |
| NAC | 1.2 | 2.4 | 1.2 | 4.08 |
| L-carnitine | 1 | 2 | 1 | 3.40 |
| L-glycine | 2.7 | 5.4 | 2.7 | 9.18 |
| L-valine | 1.8 | 3.6 | 1.8 | 6.12 |
| L-histidine | 1.8 | 3.6 | 1.8 | 6.12 |
| L-lysine | 1.8 | 3.6 | 1.8 | 6.12 |
| Total amino acids | 29.4 | 58.8 | | |

In some embodiments, the composition includes 1.2 g+/−20% of an leucine amino acid entity; 1.5 g+/−20% of an arginine amino acid entity; 3.67 g+/−20% of a glutamine amino acid entity; 0.4 g of a NAC entity; 0.33 g+/−20% of a carnitine entity; 0.9 g+/−20% of a glycine amino acid entity; 0.6 g+/−20% of a valine amino acid entity; 0.6 g+/−20% of a histidine amino acid entity; and 0.6 g+/−20% of a lysine amino acid entity. In some embodiments, the composition includes 1.2 g+/−15% of an leucine amino acid entity; 1.5 g+/−15% of an arginine amino acid entity; 3.67 g+/−15% of a glutamine amino acid entity; 0.4 g of a NAC entity; 0.33 g+/−15% of a carnitine entity; 0.9 g+/−15% of a glycine amino acid entity; 0.6 g+/−15% of a valine amino acid entity; 0.6 g+/−15% of a histidine amino acid entity; and 0.6 g+/−15% of a lysine amino acid entity. In some embodiments, the composition includes 1.2 g+/−10% of an leucine amino acid entity; 1.5 g+/−10% of an arginine amino acid entity; 3.67 g+/−10% of a glutamine amino acid entity; 0.4 g of a NAC entity; 0.33 g+/−10% of a carnitine entity; 0.9 g+/−10% of a glycine amino acid entity; 0.6 g+/−10% of a valine amino acid entity; 0.6 g+/−10% of a histidine amino acid entity; and 0.6 g+/−10% of a lysine amino acid entity. In some embodiments, the composition includes 1.2 g+/−5% of an leucine amino acid entity; 1.5 g+/−5% of an arginine amino acid entity; 3.67 g+/−5% of a glutamine amino acid entity; 0.4 g of a NAC entity; 0.33 g+/−5% of a carnitine entity; 0.9 g+/−5% of a glycine amino acid entity; 0.6 g+/−5% of a valine amino acid entity; 0.6 g+/−5% of a histidine amino acid entity; and 0.6 g+/−5% of a lysine amino acid entity.

In some embodiments, the composition includes 0.6 g+/−20% of an leucine amino acid entity; 0.75 g+/−20% of an arginine amino acid entity; 1.83 g+/−20% of a glutamine amino acid entity; 0.2 g+/−20% of a NAC entity; 0.17 g+/−20% of a carnitine entity; 0.45 g+/−20% of a glycine amino acid entity; 0.3 g+/−20% of a valine amino acid entity; 0.3 g+/−20% of a histidine amino acid entity; and 0.3 g+/−20% of a lysine amino acid entity. In some embodiments, the composition includes 0.6 g+/−15% of an leucine amino acid entity; 0.75 g+/−15% of an arginine amino acid entity; 1.83 g+/−15% of a glutamine amino acid entity; 0.2 g+/−15% of a NAC entity; 0.17 g+/−15% of a carnitine entity; 0.45 g+/−15% of a glycine amino acid entity; 0.3 g+/−15% of a valine amino acid entity; 0.3 g+/−15% of a histidine amino acid entity; and 0.3 g+/−15% of a lysine amino acid entity. In some embodiments, the composition includes 0.6 g+/−10% of an leucine amino acid entity; 0.75 g+/−10% of an arginine amino acid entity; 1.83 g+/−10% of a glutamine amino acid entity; 0.2 g+/−10% of a NAC entity; 0.17 g+/−10% of a carnitine entity; 0.45 g+/−10% of a glycine amino acid entity; 0.3 g+/−10% of a valine amino acid entity; 0.3 g+/−10% of a histidine amino acid entity; and 0.3 g+/−10% of a lysine amino acid entity. In some embodiments, the composition includes 0.6 g+/−5% of an leucine amino acid entity; 0.75 g+/−5% of an arginine amino acid entity; 1.83 g+/−5% of a glutamine amino acid entity; 0.2 g+/−5% of a NAC entity; 0.17 g+/−5% of a carnitine entity; 0.45 g+/−5% of a glycine amino acid entity; 0.3 g+/−5% of a valine amino acid entity; 0.3 g+/−5% of a histidine amino acid entity; and 0.3 g+/−5% of a lysine amino acid entity ii. Ratios An exemplary composition can include a weight (wt.) ratio of the leucine amino acid entity, the arginine amino acid entity, the glutamine amino acid entity, and the NAC entity of 3.6:4.5:11:1.2. In some embodiments, the wt. ratio of the leucine amino acid entity, the arginine amino acid entity, the glutamine amino acid entity, and the NAC entity is 3.6+/−15%: 4.5+/−15%:11+/−15%:1.2+/−15%. In some embodiments, the wt. ratio of the leucine amino acid entity, the arginine amino acid entity, the glutamine amino acid entity, and the NAC entity is 3.6+/−10%:4.5+/−10%:11+/−10%:1.2+/−10%. In some embodiments, the wt. ratio of the leucine amino acid entity, the arginine amino acid entity, the glutamine amino acid entity, and the NAC entity is 3.6+/−5%:4.5+/−5%:11+/−5%:1.2+/−5%.

An exemplary composition can include a weight (wt.) ratio of the leucine amino acid entity, the arginine amino acid entity, the glutamine amino acid entity, the NAC entity, the carnitine entity, and the glycine amino acid entity is 3.6:4.5:11:1.2:1:2.7. In some embodiments, the wt. ratio of the leucine amino acid entity, the arginine amino acid entity, the glutamine amino acid entity, the NAC entity, the carnitine entity, and the glycine amino acid entity is 3.6+/−15%: 4.5+/−15%:11+/−15%:1.2+/−15%:1+/−15%:2.7+/−15%. In some embodiments, the wt. ratio of the leucine amino acid entity, the arginine amino acid entity, the glutamine amino acid entity, the NAC entity, the carnitine entity, and the glycine amino acid entity is 3.6+/−10%:4.5+/−10%:11+/−10%:1.2+/−10%:1+/−10%:2.7+/−10%. In some embodiments, the wt. ratio of the leucine amino acid entity, the arginine amino acid entity, the glutamine amino acid entity, the NAC entity, the carnitine entity, and the glycine amino acid entity is 3.6+/−5%:4.5+/−5%:11+/−5%:1.2+/−5%:1+/−5%:2.7+/−5%.

iii. Relationships of Amino Acid Entities

In some embodiments, the wt. % of the leucine amino acid entity, the arginine amino acid entity, the glutamine amino acid entity, and the NAC entity is at least: 40 wt. %, 50 wt. %, or 60 wt. % of the amino acid entity components or total components in the composition (e.g., in dry form), but not more than 80 wt. % of the amino acid entity components or total components in the composition (e.g., in dry form).

In some embodiments, the wt. % of the leucine amino acid entity, the arginine amino acid entity, the glutamine amino acid entity, the NAC entity, the carnitine entity, and the glycine entity is at least: 50 wt. %, 60 wt. %, or 70 wt. % of the amino acid entity components or total components in the composition (e.g., in dry form), but not more than 95 wt. % of the amino acid entity components or total components in the composition (e.g., in dry form).

In some embodiments, the wt. % of the NAC entity is at least: 2 wt. %, 3 wt. %, or 4 wt. % of the amino acid entity components or total components in the composition (e.g., in dry form), but not more than 10 wt. % of the amino acid entity components or total components in the composition (e.g., in dry form).

In some embodiments, the glutamine amino acid entity is present at a greater wt. % than one, two, or more (e.g., all) of any other amino acid entity, non-amino acid entity protein component, or non-protein component in the composition (e.g., in dry form). In some embodiments, the wt. % of the glutamine amino acid entity is at least: 20 wt. %, 30 wt. %, or 35 wt. % of the amino acid entity components or total components in the composition (e.g., in dry form), but not more than 70 wt. % of the amino acid entity components or total components in the composition (e.g., in dry form).

In some embodiments, the wt. % of the carnitine entity is at least: 1 wt. %, 2 wt. %, or 3 wt. % of the amino acid entity components or total components in the composition (e.g., in dry form), but not more than 10 wt. % of the amino acid entity components or total components in the composition (e.g., in dry form).

In some embodiments, the wt. % of the glycine amino acid entity is at least: 3 wt. %, 5 wt. %, or 7 wt. % of the amino acid entity components or total components in the composition (e.g., in dry form), but not more than 20 wt. % of the amino acid entity components or total components in the composition (e.g., in dry form).

In some embodiments, the wt. % of the glutamine amino acid entity in the composition (e.g., in dry form) is greater than the wt. % of the leucine amino acid entity, e.g., the wt. % of the glutamine amino acid entity in the composition (e.g., in dry form) is at least 30% greater than the wt. % of the leucine amino acid entity, e.g., the wt. % of the glutamine amino acid entity is at least 40%, 50%, or 60% greater than the wt. % of the leucine amino acid entity.

In some embodiments, the wt. % of the glutamine amino acid entity in the composition (e.g., in dry form) is greater than the wt. % of the arginine amino acid entity, e.g., the wt. % of the glutamine amino acid entity in the composition (e.g., in dry form) is at least 25% greater than the wt. % of the arginine amino acid entity, e.g., the wt. % of the glutamine amino acid entity is at least 35%, 45%, or 55% greater than the wt. % of the arginine amino acid entity.

In some embodiments, the wt. % of the glycine amino acid entity in the composition (e.g., in dry form) is greater than the wt. % of the carnitine entity, e.g., the wt. % of the glycine amino acid entity in the composition (e.g., in dry form) is at least 30% greater than the wt. % of the carnitine entity, e.g., the wt. % of the glycine amino acid entity is at least 40%, 50%, or 60% greater than the wt. % of the carnitine entity.

iv. Amino Acid Molecules to Exclude or Limit from the Composition

In some embodiments, the composition does not comprise a peptide of more than 20 amino acid residues in length (e.g., protein supplement) chosen from or derived from one, two, three, four, five, or more (e.g., all) of egg white protein, soy protein, casein, hemp protein, pea protein, or brown rice protein, or if the peptide is present, the peptide is present at less than: 10 weight (wt.) 5 wt. %, 1 wt. %, 0.1 wt. %, 0.05 wt. %, 0.01 wt. %, of the total wt. of non-amino acid entity protein components or total components in the composition (e.g., in dry form).

In some embodiments, the composition comprises a combination of 3 to 18, 3 to 16, or 3 to 14 different amino acid entities, e.g., the combination comprises at least: 42 wt. %, 75 wt. %, or 90 wt. % of the total wt. % of amino acid entity components or total components in the composition (e.g., in dry form).

In some embodiments, dipeptides or salts thereof or tripeptides or salts thereof are present at less than: 10 wt. %, 0.5 wt. %, 0.1 wt. %, 0.05 wt. %, 0.01 wt. %, 0.001 wt. %, or less of the total wt. of amino acid entity components or total components in the composition (e.g., in dry form).

In some embodiments, at least 50%, 60%, 70%, or more of the total grams of amino acid entity components in the composition (e.g., in dry form) are from one, two, three, four, five, six, seven, or more (e.g., all) of (a)-(h).

In some embodiments, at least: 50%, 60%, 70%, or more of the calories from amino acid entity components or total components in the composition (e.g., in dry form) are from one, two, three, four, five, six, seven, or more (e.g., all) of (a)-(h).

In some embodiments, tryptophan is absent from the composition, or if present, is present at less than: 10 wt. %, 9 wt. %, 8 wt. %, 7 wt. %, 6 wt. %, 5 wt. %, 4 wt. %, 3 wt. %, 2 wt. %, 1 wt. %, 0.5 wt. %, 0.1 wt. %, 0.05 wt. %, 0.01 wt. %, 0.001 wt. %, or less, e.g., of the total wt. of the composition (e.g., in dry form). In some embodiments, tryptophan, if present, is present in free form. In some embodiments, tryptophan, if present, is present in salt form. In some embodiments, tryptophan, if present, may be present in an oligopeptide, polypeptide, or protein, with the proviso that the protein is not whey, casein, lactalbumin, or any other protein used as a nutritional supplement, medical food, or similar product, whether present as intact protein or protein hydrolysate. In some embodiments, methionine is absent from the composition, or if present, is present at less than: 10 wt. %, 5 wt. %, 1 wt. %, 0.5 wt. %, 0.1 wt. %, 0.05 wt. %, 0.01 wt. %, 0.001 wt. %, or less, e.g., of the total wt. of the composition (in dry form). In some embodiments, proline is absent from the composition, or if present, is present at less than: 10 wt. %, 5 wt. %, 1 wt. %, 0.5 wt. %, 0.1 wt. %, 0.05 wt. %, 0.01 wt. %, 0.001 wt. %, or less, e.g., of the total wt. of the composition (in dry form). In some embodiments, one, two, or three of methionine, proline, or tryptophan is absent from the composition, or if present, is present at less than: 10 wt. %, 5 wt. %, 1 wt. %, 0.5 wt. %, 0.1 wt. %, 0.05 wt. %, 0.01 wt. %, 0.001 wt. %, or less, e.g., of the total wt. of the composition (in dry form).

In some embodiments, a carbohydrate (e.g., one, two, three, four, five, six, seven, eight, nine, 10, 11, 12, 13, 14, 15, 16, 17, or 18 of dextrose, maltodextrose, sucrose, dextrin, fructose, galactose, glucose, glycogen, high fructose corn syrup, honey, inositol, invert sugar, lactose, levulose, maltose, molasses, sugarcane, or xylose) is absent from the composition, or if present, is present at less than: 10 wt. %, 5 wt. %, 1 wt. %, 0.5 wt. %, 0.1 wt. %, 0.05 wt. %, 0.01 wt. %, 0.001 wt. %, or less, e.g., of the total wt. of the composition (in dry form).

In some embodiments, a vitamin (e.g., one, two, three, four, five, six, or seven of vitamin B1, vitamin B2, vitamin B3, vitamin B6, vitamin B12, vitamin C, or vitamin D) is absent from the composition, or if present, is present at less than: 10 wt. %, 5 wt. %, 1 wt. %, 0.5 wt. %, 0.1 wt. %, 0.05 wt. %, 0.01 wt. %, 0.001 wt. %, or less, e.g., of the total wt. of the composition (in dry form).

In some embodiments, one or both of nitrate or nitrite are absent from the composition, or if present, are present at less than: 10 wt. %, 5 wt. %, 1 wt. %, 0.5 wt. %, 0.1 wt. %, 0.05 wt. %, 0.01 wt. %, 0.001 wt. %, or less, e.g., of the total wt. of the composition (in dry form).

In some embodiments, 4-hydroxyisoleucine is absent from the composition, or if present, is present at less than: 10 wt. %, 5 wt. %, 1 wt. %, 0.5 wt. %, 0.1 wt. %, 0.05 wt. %, 0.01 wt. %, 0.001 wt. %, or less, e.g., of the total wt. of the composition (in dry form).

In some embodiments, a probiotic (e.g., a *Bacillus* probiotic) is absent from the composition, or if present, is present at less than: 10 wt. %, 5 wt. %, 1 wt. %, 0.5 wt. %, 0.1 wt. %, 0.05 wt. %, 0.01 wt. %, 0.001 wt. %, or less, e.g., of the total wt. of the composition (in dry form).

In some embodiments, phenylacetate is absent from the composition, or if present, is present at less than: 10 wt. %, 5 wt. %, 1 wt. %, 0.5 wt. %, 0.1 wt. %, 0.05 wt. %, 0.01 wt. %, 0.001 wt. %, or less, e.g., of the total wt. of the composition (in dry form).

In some embodiments, gelatin (e.g., a gelatin capsule) is absent from the composition, or if present, is present at less than: 10 wt. %, 5 wt. %, 1 wt. %, 0.5 wt. %, 0.1 wt. %, 0.05 wt. %, 0.01 wt. %, 0.001 wt. %, or less, e.g., of the total wt. of the composition (in dry form).

In some embodiments, one, two, or three of S-allyl cysteine, S-allylmercaptocysteine, or fructosyl-arginine is absent from the composition, or if present, is present at less than: 10 wt. %, 5 wt. %, 1 wt. %, 0.5 wt. %, 0.1 wt. %, 0.05 wt. %, 0.01 wt. %, 0.001 wt. %, or less, e.g., of the total wt. of the composition (in dry form).

v. Amounts and Ratios

An exemplary composition (e.g., an Active Moiety) can include 0.6 g+/−20% of a leucine amino acid entity, 1.4 g+/−20% of an arginine amino acid entity, 1.5 g+/−20% of a glutamine amino acid entity, 0.26+/−20% g of a NAC entity, 0.2 g+/−20% of a carnitine entity, 0.75 g+/−20% of a serine amino acid entity, 0.3 g+/−20% of a valine amino acid entity, 0.3 g+/−20% of a histidine amino acid entity, 0.3 g+/−20% of a lysine amino acid entity, and 0.9 g+/−20% of a citrulline amino acid entity (see, e.g., g/stickpack for 5 stick packs administered twice daily in Table 3).

TABLE 3

Exemplary composition comprising amino acids (e.g., an Active Moiety).

| Amino Acid | Stick pack (g) (5 stick packs BID) | Stick pack (g) (4 stick packs BID) | Stick pack (g) (3 stick packs BID) | Dose (g) | Total Daily | Wt. Ratio | Wt. % |
|---|---|---|---|---|---|---|---|
| L-leucine | 0.6 | 0.75 | 1 | 3 | 6 | 3 | 9.22% |
| L-arginine | 1.4 | 1.75 | 2.33 | 7 | 14 | 7 | 21.51% |
| L-glutamine | 1.5 | 1.875 | 2.5 | 7.5 | 15 | 7.5 | 23.04% |
| N-acetylcysteine | 0.26 | 0.325 | 0.43 | 1.3 | 2.6 | 1.3 | 3.99% |
| L-carnitine | 0.2 | 0.25 | 0.33 | 1 | 2 | 1 | 3.07% |
| L-serine | 0.75 | 0.9375 | 1.25 | 3.75 | 7.5 | 3.75 | 11.52% |
| L-valine | 0.3 | 0.375 | 0.5 | 1.5 | 3 | 1.5 | 4.61% |
| L-histidine | 0.3 | 0.375 | 0.5 | 1.5 | 3 | 1.5 | 4.61% |
| L-lysine | 0.3 | 0.375 | 0.5 | 1.5 | 3 | 1.5 | 4.61% |
| L-citrulline | 0.9 | 1.125 | 1.5 | 4.5 | 9 | 4.5 | 13.82% |
| Total amino acids | 6.51 | 8.1375 | 10.85 | 32.55 | 65.1 | | 100% |

An exemplary composition (e.g., an Active Moiety) can include 0.75 g+/−20% of a leucine amino acid entity, 1.75 g+/−20% of an arginine amino acid entity, 1.875 g+/−20% of a glutamine amino acid entity, 0.325+/−20% g of a NAC entity, 0.25 g+/−20% of a carnitine entity, 0.9375 g+/−20% of a serine amino acid entity, 0.375 g+/−20% of a valine amino acid entity, 0.375 g+/−20% of a histidine amino acid entity, 0.375 g+/−20% of a lysine amino acid entity, and 1.125 g+/−20% of a citrulline amino acid entity (see, e.g., g/stickpack for 4 stick packs administered twice daily in Table 3).

An exemplary composition (e.g., an Active Moiety) can include 1 g+/−20% of a leucine amino acid entity, 2.33 g+/−20% of an arginine amino acid entity, 2.5 g+/−20% of a glutamine amino acid entity, 0.43+/−20% g of a NAC entity, 0.33 g+/−20% of a carnitine entity, 1.25 g+/−20% of a serine amino acid entity, 0.5 g+/−20% of a valine amino acid entity, 0.5 g+/−20% of a histidine amino acid entity, 0.5 g+/−20% of a lysine amino acid entity, and 1.5 g+/−20% of a citrulline amino acid entity (see, e.g., g/stickpack for 3 stick packs administered twice daily in Table 3).

An exemplary composition (e.g., an Active Moiety) can include 3 g+/−20% of a leucine amino acid entity, 7 g+/−

20% of an arginine amino acid entity, 7.5 g+/−20% of a glutamine amino acid entity, 1.3+/−20% g of a NAC entity, 1 g+/−20% of a carnitine entity, 3.75 g+/−20% of a serine amino acid entity, 1.5 g+/−20% of a valine amino acid entity, 1.5 g+/−20% of a histidine amino acid entity, 1.5 g+/−20% of a lysine amino acid entity, and 4.5 g+/−20% of a citrulline amino acid entity (see, e.g., g/dose administered twice daily in Table 3).

An exemplary composition (e.g., an Active Moiety) can include 6 g+/−20% of a leucine amino acid entity, 14 g+/−20% of an arginine amino acid entity, 15 g+/−20% of a glutamine amino acid entity, 2.6+/−20% g of a NAC entity, 2 g+/−20% of a carnitine entity, 7.5 g+/−20% of a serine amino acid entity, 3 g+/−20% of a valine amino acid entity, 3 g+/−20% of a histidine amino acid entity, 3 g+/−20% of a lysine amino acid entity, and 9 g+/−20% of a citrulline amino acid entity (see, e.g., total daily in Table 3).

An exemplary composition can include a weight (wt.) ratio of a leucine amino acid entity, an arginine amino acid entity, a glutamine amino acid entity, a NAC entity, carnitine entity, a serine amino acid entity, a valine amino acid entity, a histidine amino acid entity, a lysine amino acid entity, and a citrulline amino acid entity of 3+/−15%:7+/−15%:7.5+/−15%: 1.3+/−15%:1+/−15%:3.75+/−15%:1.5+/−15%:1.5+/−15%:1.5+/−15%:4.5+/−15% (see, e.g., wt. ratio in Table 3).

An exemplary composition (e.g., an Active Moiety) can include 0.35 g+/−20% of a leucine amino acid entity, 0.8 g+/−20% of an arginine amino acid entity, 1 g+/−20% of a glutamine amino acid entity, 0.18+/−20% g of a NAC entity, 0.2 g+/−20% of a carnitine entity, 0.43 g+/−20% of a serine amino acid entity, 0.18 g+/−20% of a valine amino acid entity, 0.18 g+/−20% of a histidine amino acid entity, 0.18 g+/−20% of a lysine amino acid entity, and 0.52 g+/−20% of a citrulline amino acid entity (see, e.g., g/stickpack for 5 stick packs administered twice daily in Table 4A).

An exemplary composition (e.g., an Active Moiety) can include 0.44 g+/−20% of a leucine amino acid entity, 1 g+/−20% of an arginine amino acid entity, 1.25 g+/−20% of a glutamine amino acid entity, 0.23+/−20% g of a NAC entity, 0.25 g+/−20% of a carnitine entity, 0.54 g+/−20% of a serine amino acid entity, 0.23 g+/−20% of a valine amino acid entity, 0.23 g+/−20% of a histidine amino acid entity, 0.23 g+/−20% of a lysine amino acid entity, and 0.65 g+/−20% of a citrulline amino acid entity (see, e.g., g/stickpack for 4 stick packs administered twice daily in Table 4A).

An exemplary composition (e.g., an Active Moiety) can include 0.58 g+/−20% of a leucine amino acid entity, 1.33 g+/−20% of an arginine amino acid entity, 1.67 g+/−20% of a glutamine amino acid entity, 0.3+/−20% g of a NAC entity, 0.33 g+/−20% of a carnitine entity, 0.72 g+/−20% of a serine amino acid entity, 0.3 g+/−20% of a valine amino acid entity, 0.3 g+/−20% of a histidine amino acid entity, 0.3 g+/−20% of a lysine amino acid entity, and 0.87 g+/−20% of a citrulline amino acid entity (see, e.g., g/stickpack for 3 stick packs administered twice daily in Table 4A).

An exemplary composition (e.g., an Active Moiety) can include 1.75 g+/−20% of a leucine amino acid entity, 4 g+/−20% of an arginine amino acid entity, 5 g+/−20% of a glutamine amino acid entity, 0.9+/−20% g of a NAC entity, 1 g+/−20% of a carnitine entity, 2.15 g+/−20% of a serine amino acid entity, 0.9 g+/−20% of a valine amino acid entity, 0.9 g+/−20% of a histidine amino acid entity, 0.9 g+/−20% of a lysine amino acid entity, and 2.6 g+/−20% of a citrulline amino acid entity (see, e.g., g/dose in Table 4A).

An exemplary composition (e.g., an Active Moiety) can include 3.5 g+/−20% of a leucine amino acid entity, 8 g+/−20% of an arginine amino acid entity, 10 g+/−20% of a glutamine amino acid entity, 1.8+/−20% g of a NAC entity, 2 g+/−20% of a carnitine entity, 4.3 g+/−20% of a serine amino acid entity, 1.8 g+/−20% of a valine amino acid entity, 1.8 g+/−20% of a histidine amino acid entity, 1.8 g+/−20% of a lysine amino acid entity, and 5.2 g+/−20% of a citrulline amino acid entity (see, e.g., total daily in Table 4A).

An exemplary composition can include a weight (wt.) ratio of a leucine amino acid entity, an arginine amino acid entity, a glutamine amino acid entity, a NAC entity, a carnitine entity, a serine amino acid entity, a valine amino acid entity, a histidine amino acid entity, a lysine amino acid entity, and a citrulline amino acid entity of 1.94+/−15%: 4.44+/−15%: 5.56+/−15%:1+/−15%:1.11+/−15%:2.39+/−15%:1+/−15%:1+/−15%:1+/−15%:2.89+/−15%.

TABLE 4A

Exemplary composition comprising amino acids (e.g., an Active Moiety).

| Amino Acid | Stick pack (g) (5 stick packs BID) | Stick pack (g) (4 stick packs BID) | Stick pack (g) (3 stick packs BID) | Dose (g) | Total Daily | Wt. Ratio | Wt. % |
|---|---|---|---|---|---|---|---|
| L-leucine | 0.35 | 0.44 | 0.58 | 1.75 | 3.5 | 1.94 | 8.71% |
| L-arginine | 0.8 | 1 | 1.33 | 4 | 8 | 4.44 | 19.90% |
| L-glutamine | 1 | 1.25 | 1.67 | 5 | 10 | 5.56 | 24.88% |
| N-acetylcysteine | 0.18 | 0.23 | 0.3 | 0.9 | 1.8 | 1 | 4.48% |
| L-carnitine | 0.2 | 0.25 | 0.33 | 1 | 2 | 1.11 | 4.98% |
| L-serine | 0.43 | 0.54 | 0.72 | 2.15 | 4.3 | 2.39 | 10.70% |
| L-valine | 0.18 | 0.23 | 0.3 | 0.9 | 1.8 | 1 | 4.48% |
| L-histidine | 0.18 | 0.23 | 0.3 | 0.9 | 1.8 | 1 | 4.48% |
| L-lysine | 0.18 | 0.23 | 0.3 | 0.9 | 1.8 | 1 | 4.48% |
| L-citrulline | 0.52 | 0.65 | 0.87 | 2.6 | 5.2 | 2.89 | 12.94% |
| Total amino acids | 4.02 | 5.025 | 6.7 | 20.1 | 40.2 | | 100% |

TABLE 4B

Exemplary composition comprising amino acids (e.g., an Active Moiety).

| Amino Acid | Stick pack (g) (3 stick packs BID) | Dose (g) | Total Daily | Wt. Ratio | Wt. % |
|---|---|---|---|---|---|
| L-leucine | 1.0 | 3 | 6 | 3 | 11.41 |
| L-arginine | 2.0 | 6 | 12 | 6 | 22.81 |
| L-glutamine | 1.67 | 5 | 10 | 5 | 19.01 |
| N-acetylcysteine | 0.43 | 1.3 | 2.6 | 1.3 | 4.94 |
| L-carnitine | 0.333 | 1 | 2 | 1 | 3.80 |
| L-serine | 0.83 | 2.5 | 5 | 2.5 | 9.51 |
| L-valine | 0.333 | 1 | 2 | 1 | 3.80 |
| L-histidine | 0.333 | 1 | 2 | 1 | 3.80 |
| L-lysine | 0.5 | 1.5 | 3 | 1.5 | 5.70 |
| L-citrulline | 1.33 | 4 | 8 | 4 | 15.21 |
| Total amino acids | 8.76 | 26.3 | 52.6 | | 100% |

An exemplary composition (e.g., an Active Moiety) can include 3 g+/−20% of a leucine amino acid entity, 6 g+/−20% of an arginine amino acid entity, 5 g+/−20% of a glutamine amino acid entity, 1.3+/−20% g of a NAC entity, 1 g+/−20% of a carnitine entity, 2.5 g+/−20% of a serine amino acid entity, 1 g+/−20% of a valine amino acid entity, 1 g+/−20% of a histidine amino acid entity, 1.5 g+/−20% of a lysine amino acid entity, and 4 g+/−20% of a citrulline amino acid entity (see, e.g., g/dose in Table 4B). An exemplary composition (e.g., an Active Moiety) can include 6 g+/−20% of a leucine amino acid entity, 12 g+/−20% of an arginine amino acid entity, 10 g+/−20% of a glutamine amino acid entity, 2.6+/−20% g of a NAC entity, 2 g+/−20% of a carnitine entity, 5 g+/−20% of a serine amino acid entity, 2 g+/−20% of a valine amino acid entity, 2 g+/−20% of a histidine amino acid entity, 3 g+/−20% of a lysine amino acid entity, and 8 g+/−20% of a citrulline amino acid entity (see, e.g., total daily in Table 4B).

An exemplary composition can include a weight (wt.) ratio of a leucine amino acid entity, an arginine amino acid entity, a glutamine amino acid entity, a NAC entity, a carnitine entity, a serine amino acid entity, a valine amino acid entity, a histidine amino acid entity, a lysine amino acid entity, and a citrulline amino acid entity of 3+/−15%:6+/−15%:5+/−15%: 1.3+/−15%:1+/−15%:2.5+/−15%:1+/−15%: 1+/−15%:1.5+/−15%:4+/−15%.

v. Relationships of Amino Acid Entities

In some embodiments, the wt. % of the leucine amino acid entity, the arginine amino acid entity, the glutamine amino acid entity, the NAC entity, the carnitine entity, the serine amino acid entity, the valine amino acid entity, the histidine amino acid entity, the lysine amino acid entity, and the citrulline amino acid entity is at least: 70 wt. %, 75 wt. %, 80 wt. %, 85 wt. %, 90 wt. %, 95 wt. %, 97 wt. %, 98 wt. %, or more of the amino acid entity components or total components in the composition (e.g., in dry form).

In some embodiments, the wt. % of the leucine amino acid entity, the arginine amino acid entity, the glutamine amino acid entity, the serine amino acid entity, and the citrulline amino acid entity is at least: 50 wt. %, 55 wt. %, 60 wt. %, 65 wt. %, 70 wt. %, 75 wt. %, 76 wt. %, 77 wt. %, or more of the amino acid entity components or total components in the composition (e.g., in dry form).

In some embodiments, the wt. % of the leucine amino acid entity, the arginine amino acid entity, the glutamine amino acid entity, and the serine amino acid entity is at least: 40 wt. %, 45 wt. %, 50 wt. %, 55 wt. %, 60 wt. %, 61 wt. %, 62 wt. %, 63 wt. %, 65 wt. %, or more of the amino acid entity components or total components in the composition (e.g., in dry form).

In some embodiments, the wt. % of the leucine amino acid entity, the arginine amino acid entity, glutamine amino acid entity, the serine amino acid entity, the citrulline amino acid, and the carnitine entity is at least: 50 wt. %, 55 wt. %, 60 wt. %, 65 wt. %, 70 wt. %, 75 wt. %, 80 wt. %, 81 wt. %, 82 wt. %, or more of the amino acid entity components or total components in the composition (e.g., in dry form).

In some embodiments, the wt. % of the leucine amino acid entity, the arginine amino acid entity, the citrulline amino acid, and the glutamine amino acid entity is at least: 50 wt. %, 55 wt. %, 60 wt. %, 61 wt. %, 62 wt. %, 63 wt. %, 64 wt. %, 65 wt. %, 66 wt. %, or more of the amino acid entity components or total components in the composition (e.g., in dry form).

In some embodiments, the wt. % of the leucine amino acid entity, the arginine amino acid entity, and the glutamine amino acid entity is at least: 30 wt. %, 35 wt. %, 40 wt. %, 45 wt. %, 50 wt. %, 51 wt. %, 52 wt. %, 53 wt. %, or more of the amino acid entity components or total components in the composition (e.g., in dry form).

In some embodiments, the wt. % of the leucine amino acid entity is greater, e.g., at least: 50 wt. %, 55 wt %., 60 wt. %, 65 wt %., 70 wt. %, 71 wt. %, 72 wt. %, 73 wt. %, 74 wt. %, 75 wt. %, or more greater, than the wt. % of one, two, three, four, or five of the NAC entity, the carnitine entity, the valine amino acid entity, the histidine amino acid entity, or the lysine amino acid entity in the composition (e.g., in dry form).

In some embodiments, the wt. % of the arginine amino acid entity or the glutamine amino acid entity, singly or in combination, is greater, e.g., at least: 50 wt. %, 55 wt %., 60 wt. %, 65 wt %., 70 wt. %, 75 wt. %, 80 wt. %, 85 wt %., 90 wt. %, 95 wt %., or more greater, than the wt. % of one, two, three, four, five, or six of the leucine amino acid entity, the NAC entity, the carnitine entity, the valine amino acid entity, the histidine amino acid entity, or the lysine amino acid entity in the composition (e.g., in dry form).

In some embodiments, the wt. % of the NAC entity is greater, e.g., at least: 5 wt. %, 10 wt. %, 15 wt %., 20 wt. %, 25 wt %., 25 wt. %, 28 wt %., 29 wt. %, 30 wt %., or more greater, than the wt. % of the carnitine entity in the composition (e.g., in dry form).

In some embodiments, the wt. % of the carnitine entity is greater, e.g., at least: 2 wt. %, 3 wt. %, 4 wt. %, 5 wt. %, 6 wt. %, 7 wt. %, 8 wt. %, 9 wt. %, 10 wt. %, 11 wt. %, or more greater, than the wt. % of the NAC entity in the composition (e.g., in dry form).

In some embodiments, the wt. % of the citrulline amino acid or the serine amino acid, singly or in combination, is greater, e.g., at least: 5 wt. %, 10 wt. %, 15 wt %., 16 wt. %, 17 wt. %, 18 wt. %, 19 wt. %, 20 wt. %, 21 wt %., 22 wt. %, or more greater than the wt. % of one, two, three, four, five, or six of the leucine amino acid entity, the NAC entity, the carnitine entity, the valine amino acid entity, the histidine amino acid entity, or the lysine amino acid entity in the composition (e.g., in dry form).

In some embodiments, the wt. % of the valine amino acid entity, the histidine amino acid entity, and the lysine amino acid entity in combination is greater, e.g., at least: 20 wt. %, 25 wt. %, 30 wt. %, 35 wt. %, 40 wt. %, 45 wt. %, 47 wt.

%, 48 wt. %, 50 wt. %, or more greater than the wt. % of one, two, or three of the leucine amino acid entity, the NAC entity, or the carnitine entity in the composition (e.g., in dry form).

In some embodiments, the wt. % of the leucine amino acid entity, the arginine amino acid entity, and the glutamine amino acid entity in combination is greater, e.g., at least: 30 wt. %, 35 wt. %, 40 wt. %, 45 wt. %, 50 wt. %, 55 wt. %, 60 wt. %, 65 wt. %, or more greater than the wt. % of one, two, three, four, five, six, or seven of the NAC entity, the carnitine entity, the serine amino acid entity, the valine amino acid entity, the histidine amino acid entity, the lysine amino acid entity, or the citrulline amino acid entity.

In some embodiments, the wt. % of the arginine amino acid entity and the citrulline amino acid entity in combination is greater, e.g., at least: 5 wt. %, 10 wt. %, 15 wt %., 20 wt. %, 25 wt %., 25 wt. %, 28 wt %., 29 wt. %, 30 wt %., or more greater than the wt. % of one, two, three, four, five, six, seven, or eight of the leucine amino acid entity, the glutamine amino acid entity, the NAC entity, the carnitine entity, the serine amino acid entity, the valine amino acid entity, the histidine amino acid entity, or the lysine amino acid entity.

In some embodiments, the wt. % of the leucine amino acid entity is at least: 3 wt. %, 4 wt. %, 5 wt. %, 6 wt. %, 7 wt. %, 8 wt. %, or more of the amino acid entity components or total components in the composition (e.g., in dry form), but not more than 40 wt. % of the amino acid entity components or total components in the composition (e.g., in dry form). In certain embodiments, the wt. % of the leucine amino acid entity is at least 9 wt. % of the amino acid entity componentsor total components in the composition (e.g., in dry form).

In some embodiments, the wt. % of the arginine amino acid entity is at least: 5 wt. %, 10 wt. %, 11 wt. %, 12 wt. %, 13 wt. %, 14 wt. %, 15 wt. %, 16 wt. %, 17 wt. %, 18 wt. %, 19 wt. %, or more of the amino acid entity componentsor total components in the composition (e.g., in dry form), but not more than 60 wt. % of the amino acid entity componentsor total components in the composition (e.g., in dry form). In some embodiments, the wt. % of the arginine amino acid entity is at least 20 wt. % of the amino acid entity componentsor total components in the composition (e.g., in dry form).

In some embodiments, the wt. % of the glutamine amino acid entity is at least: 5 wt. %, 10 wt. %, 15 wt. %, 20 wt. %, 21 wt. %, 22 wt. %, 23 wt. %, 24 wt. %, or more of the amino acid entity componentsor total components in the composition (e.g., in dry form), but not more than 60 wt. % of the amino acid entity componentsor total components in the composition (e.g., in dry form).

In some embodiments, the wt. % of the NAC entity is at least: 1 wt. %, 2 wt. %, 3 wt. %, 4 wt. % or more of the amino acid entity componentsor total components in the composition (e.g., in dry form), but not more than 30 wt. % of the amino acid entity componentsor total components in the composition (e.g., in dry form).

In some embodiments, the wt. % of the carnitine entity is at least: 1 wt. %, 2 wt. %, 3 wt. %, 4 wt. %, or more of the amino acid entity componentsor total components in the composition (e.g., in dry form), but not more than 30 wt. % of the amino acid entity componentsor total components in the composition (e.g., in dry form).

In some embodiments, the wt. % of the serine amino acid entity is at least: 5 wt. %, 6 wt. %, 7 wt. %, 8 wt. %, 9 wt. %, 10 wt. %, or more of the amino acid entity componentsor total components in the composition (e.g., in dry form), but not more than 50 wt. % of the amino acid entity componentsor total components in the composition (e.g., in dry form). In some embodiments, the wt. % of the serine amino acid entity is at least 11 wt. %, or more of the amino acid entity componentsor total components in the composition (e.g., in dry form).

In some embodiments, the wt. % of the valine amino acid entity is at least: 1 wt. %, 2 wt. %, 3 wt. %, 4 wt. %, or more of the amino acid entity componentsor total components in the composition (e.g., in dry form), but not more than 35 wt. % of the amino acid entity componentsor total components in the composition (e.g., in dry form).

In some embodiments, the wt. % of the histidine amino acid entity is at least: 1 wt. %, 2 wt. %, 3 wt. %, 4 wt. %, or more of the amino acid entity componentsor total components in the composition (e.g., in dry form), but not more than 35 wt. % of the amino acid entity componentsor total components in the composition (e.g., in dry form).

In some embodiments, the wt. % of the lysine amino acid entity is at least: 1 wt. %, 2 wt. %, 3 wt. %, 4 wt. %, or more of the amino acid entity componentsor total components in the composition (e.g., in dry form), but not more than 35 wt. % of the amino acid entity componentsor total components in the composition (e.g., in dry form).

In some embodiments, the wt. % of the citrulline amino acid entity is at least: 5 wt. %, 10 wt. %, 11 wt. %, 12 wt. %, 13 wt. %, or more of the amino acid entity componentsor total components in the composition (e.g., in dry form), but not more than 60 wt. % of the amino acid entity componentsor total components in the composition (e.g., in dry form).

In some embodiments, the wt. % of the leucine amino acid entity is at least: 5 wt. %, 6 wt. %, 7 wt. %, 8 wt. %, 9 wt. %, 10 wt. %, or more of the amino acid entity componentsor total components in the composition (e.g., in dry form), but not more than 40 wt. % of the amino acid entity componentsor total components in the composition (e.g., in dry form).

In some embodiments, the wt. % of the arginine amino acid entity is at least: 10 wt. %, 11 wt. %, 12 wt. %, 13 wt. %, 14 wt. %, 15 wt. %, 16 wt. %, 17 wt. %, 18 wt. %, 19 wt. %, 20 wt. %, 21 wt. %, or more of the amino acid entity componentsor total components in the composition (e.g., in dry form), but not more than 60 wt. % of the amino acid entity componentsor total components in the composition (e.g., in dry form).

In some embodiments, the wt. % of the glutamine amino acid entity is at least: 5 wt. %, 10 wt. %, 15 wt. %, 16 wt. %, 17 wt. %, 18 wt. %, 19 wt. %, or more of the amino acid entity componentsor total components in the composition (e.g., in dry form), but not more than 50 wt. % of the amino acid entity componentsor total components in the composition (e.g., in dry form).

In some embodiments, the wt. % of the lysine amino acid entity is at least: 1 wt. %, 2 wt. %, 3 wt. %, 4 wt. %, 5 wt. %, or more of the amino acid entity componentsor total components in the composition (e.g., in dry form), but not more than 35 wt. % of the amino acid entity componentsor total components in the composition (e.g., in dry form).

In some embodiments, the wt. % of the citrulline amino acid entity is at least: 5 wt. %, 10 wt. %, 11 wt. %, 12 wt. %, 13 wt. %, 14 wt. %, 15 wt. %, or more of the amino acid entity componentsor total components in the composition (e.g., in dry form), but not more than 60 wt. % of the amino acid entity componentsor total components in the composition (e.g., in dry form).

Uses, e.g., Methods of Treatment

The disclosure provides a method for improving one, two, three, four, five, six, seven, eight or more (e.g., all) of erythrocyte function, turnover, or synthesis; hemoglobin function, turnover, or synthesis; vascular function; oxidative stress (e.g., one or both of blood and systemic oxidative stress); or inflammation, comprising administering to a subject in need thereof an effective amount of a composition disclosed herein (an Active Moiety). The composition can be administered according to a dosage regimen described herein to improve one, two, three, four, five, six, seven, eight or more (e.g., all) of erythrocyte function, turnover, or synthesis; hemoglobin function, turnover, or synthesis; vascular function; oxidative stress (e.g., one or both of blood and systemic oxidative stress); or inflammation in a subject (e.g., a human).

The disclosure provides a method for one or both of treating a hemoglobinopathy or a thalassemia, or preventing one or more symptoms of a hemoglobinopathy or a thalassemia in a subject, comprising administering to a subject in need thereof an effective amount of a composition disclosed herein (e.g., an Active Moiety). The composition can be administered according to a dosage regimen described herein to treat a hemoglobinopathy or a thalassemia and/or prevent one or more symptoms of a hemoglobinopathy or a thalassemia in a subject (e.g. a human).

In some embodiments, the subject has been diagnosed with a hemoglobinopathy or a thalassemia. In some embodiments, the subject has not been diagnosed with a hemoglobinopathy or a thalassemia. In some embodiments, the subject is a human (e.g., a pediatric subject or an adult subject).

In some embodiments, the subject is an infant, child, adolescent, or adult. In certain embodiments, the subject is an adolescent, e.g., the subject is 12+/−20% years to 16+/−20% years of age. In certain embodiments, the subject has a body weight of 40 kg+/−20% to 60 kg+/−20%. In certain embodiments, the subject has a body weight of greater than 60 kg+/−20%.

In some embodiments, the subject has not received prior treatment with the composition described herein (e.g., a naïve subject).

In some embodiments, the composition described herein (an Active Moiety) is for use as a medicament in improving one, two, three, four, five, six or more (e.g., all) of erythrocyte function, turnover, or synthesis; hemoglobin function, turnover, or synthesis; or vascular function in a subject (e.g., a subject with a hemoglobinopathy or a thalassemia). In some embodiments, the composition is for use as a medicament in treating (e.g., reversing, reducing, or ameliorating) a hemoglobinopathy or a thalassemia in a subject. In some embodiments, the composition is for use as a medicament in preventing one or more symptoms of a hemoglobinopathy or a thalassemia in a subject.

In some embodiments, the composition described herein (an Active Moiety) is for use in the manufacture of a medicament, supplement, medical food, or functional food for improving one, two, three, four, five, six or more (e.g., all) of erythrocyte function, turnover, or synthesis; hemoglobin function, turnover, or synthesis; or vascular function in a subject (e.g., a subject with a hemoglobinopathy or a thalassemia). In some embodiments, the composition (e.g., the Active Moiety) is for use in the manufacture of a medicament, supplement, medical food, or functional food for treating (e.g., reversing, reducing, or ameliorating) a hemoglobinopathy or a thalassemia in a subject. In some embodiments, the composition (e.g., the Active Moiety) is for use in the manufacture of a medicament for preventing one or more symptoms of a hemoglobinopathy or a thalassemia in a subject.

In some embodiments, the subject is at risk of a hemoglobinopathy (e.g., a sickle cell disease) or a thalassemia. In certain embodiments, the subject has a mutation in the HBB gene.

In one embodiment, the hemoglobinopathy is a β-hemoglobinopathy. In another embodiment, the hemoglobinopathy is an α-hemoglobinopathy.

In some embodiments, the subjects exhibits one or more symptom associated with a hemoglobinopathy chosen from: anemia, tissue hypoxia, organ dysfunction, vaso-occlusive crises, abnormal hematocrit values, ineffective erythropoiesis, abnormal reticulocyte count, abnormal iron load, the presence of ring sideroblasts, splenomegaly, hepatomegaly, impaired peripheral blood flow, dyspnea, increased hemolysis, jaundice, anemic pain crises, acute chest syndrome, splenic sequestration, priapism, stroke, hand-foot syndrome, pain (e.g., angina pectoris), or a combination thereof. Administration of the composition described herein can be effective to treat one or more of the symptoms associated with a hemoglobinopathy or a thalassemia.

In some embodiments, the hemoglobinopathy is a sickle cell disease, e.g., a sickle cell disease chosen from sickle cell anemia (HbSS), Hemoglobin SC disease (HbSC), sickle $\beta^+$-thalassemia (HbS/β+), sickle $\beta^0$-thalassemia (HbS/$\beta^0$), hemoglobin SE disease, hemoglobin SD disease, or hemoglobin SO disease. In certain embodiments, the subject has pediatric sickle cell anemia. In some embodiments, the subject has one or more diseases or disorders associated with a hemoglobinopathy (e.g., a sickle cell disease) selected from neurocognitive dysfunction, meningitis, stroke, indirect hyperbilirubinemia, sickle hepatopathy, gallstones, albuminuria, isosthenuria, substantial kidney injury, papillary necrosis, delayed puberty erectile dysfunction, priapism, avascular necrosis, bone marrow infarction, osteomyelitis, retinopathy, post-hyphema glaucoma, retinal infarction, pulmonary hypertension, acute chest pain syndrome, acute pain event, cardiomegaly, diastolic heart failure, anaemia, leukocytosis, septicaemia, functional asplenia, splenic infarction, splenic sequestration, complications of pregnancy, skin ulcers, or chronic pain. Administration of the composition described herein can be effective to treat one or more of the diseases or disorders associated with a hemoglobinopathy (e.g., a sickle cell disease).

In some embodiments, the subjects exhibits one or more symptom associated with a sickle cell disease chosen from: hemolysis, jaundice, cholelithiasis, aplastic crisis, hemolytic crisis, vaso-occlusive disease, which causes dactylitis, autosplenectomy, acute chest shyndrome, stroke priapism, renal papillary necrosis, infarctive crisis, sequestration crisis, leg ulcers, or a combination thereof. Administration of the composition described herein can be effective to treat one or more of the symptoms associated with a sickle cell disease.

In some embodiments, the thalassemia is α-thalassemia, β-thalassemia, a hemoglobin CC disease, or hemoglobin EE disease. In certain embodiments, the β-thalassemia is chosen from: minor/trait β-thalassemia ($\beta/\beta^0$ or β/β+), intermedia β-thalassemia ($\beta^0$/β+), and major β-thalassemia ($\beta^0/\beta^0$ or $\beta^+/\beta^+$).

In some embodiments, the subjects exhibits one or more symptom associated with β-thalassemia chosen from: hemolysis, anemia, splenomegaly, ineffective erythropoiesis, hepato-splenomegaly, high uric acid in blood or serum, leg ulcers, infection, or a combination thereof. Administration of the composition described herein can be effective to treat one or more of the symptoms associated with β-thalassemia.

Dosage Regimens

The composition (e.g., the Active Moiety) can be administered according to a dosage regimen described herein to improve erythrocyte and/or hemoglobin function, turnover, and/or synthesis; vascular function; inflammation; and/or oxidative stress in a subject, e.g., to reduce or treat a hemoglobinopathy (e.g., sickle cell disease) or a thalassemia. For example, the composition may be administered to the subject for a treatment period of, e.g., two weeks, three weeks, four weeks, five weeks, six weeks, seven weeks, eight weeks, nine weeks, 10 weeks, 11 weeks, 12 weeks, 13 weeks, 14 weeks, 15 weeks, 16 weeks, or longer, at a dose of 2 g+/−20% g daily to 90 g+/−20% g daily. In certain embodiments, the composition is administered at a dose of 40 g+/−20% to 80 g+/−20% total amino acid entities three times daily, e.g., 59 g+/−20% total amino acid entities daily.

In certain embodiments, the composition is administered at a dose of 30 g+/−20% to 80 g+/−20% total amino acid entities daily, e.g., 65.1 g+/−20% total amino acid entities daily to a subject (e.g., to an adult subject). In certain embodiments, the composition is administered at a dose of 15 g+/−20% to 60 g+/−20% total amino acid entities twice times daily, e.g., 32.55 g+/−20% total amino acid entities twice daily to a subject (e.g., to an adult subject).

In certain embodiments, the composition is administered at a dose of 20 g+/−20% to 60 g+/−20% total amino acid entities daily, e.g., 40.2 g+/−20% total amino acid entities daily to a subject (e.g., to a pediatric subject). In certain embodiments, the composition is administered at a dose of 10 g+/−20% to 30 g+/−20% total amino acid entities twice times daily, e.g., 20.1 g+/−20% total amino acid entities twice daily to a subject (e.g., to a pediatric subject).

In some embodiments, the composition can be provided to a subject with a hemoglobinopathy (e.g., sickle cell disease) in either a single or multiple dosage regimen. In some embodiments, a dose is administered twice daily, three times daily, four times daily, five times daily, six times daily, seven times daily, or more. In certain embodiments, the composition is administered one, two, or three times daily. In some embodiments, the composition is administered for at least 2 days, 3 days, 4 days, 5 days, 6 days, 7 days, or 2 weeks. In some embodiments, the composition is administered chronically (e.g., more than 30 days, e.g., 31 days, 40 days, 50 days, 60 days, 3 months, 6 months, 9 months, one year, two years, or three years).

In some embodiments, the composition is administered prior to a meal (e.g., breakfast, lunch or dinner). In other embodiments, the composition is administered concurrent with a meal (e.g., breakfast, lunch or dinner). In other embodiments, the composition is administered following a meal (e.g., breakfast, lunch or dinner). In certain embodiments, the composition is administered with breakfast and dinner.

The composition can be administered every 2 hours, every 3 hours, every 4 hours, every 5 hours, every 6 hours, every 7 hours, every 8 hours, every 9 hours, every 10 hours, every 11 hours, or every 12 hours to improve erythrocyte function in a subject (e.g., a subject having a hemoglobinopathy, e.g., a sickle cell disease).

In some embodiments, the composition comprises three stick packs, e.g., each stick pack comprising 33.3%+/−15% of the quantity of each amino acid entity included in the composition described herein. In certain embodiments, three stick packs are administered two times daily. In some embodiments, the composition comprises five stick packs, e.g., each stick pack comprising 20%+/−15% of the quantity of each amino acid entity included in the composition described herein. In certain embodiments, five stick packs are administered two times daily.

In some embodiments, the composition comprises four stick packs, e.g., each stick pack comprising 25%+/−15% of the quantity of each amino acid entity included in the composition described herein. In certain embodiments, four stick packs are administered two times daily.

In some embodiments, the composition is administered at a dose of about 2 g+/−20% to 80 g+/−20% total amino acid entities, e.g., once daily, twice daily, three times daily, four times daily, five times daily, or six times daily (e.g., twice daily). In some embodiments, the composition is administered at a dose of 2 g+/−20% to 10 g+/−20%, 20 g+/−20% to 50 g+/−20%, or 50 g+/−20% to 80 g+/−20% total amino acid entities, e.g., once daily, twice daily, or three times daily (e.g., twice per day). In certain embodiments, the composition is administered at a dose of 20 g+/−20% to 50 g+/−20% total amino acid entities twice daily, e.g., 29 g+/−20% total amino acid entities twice daily. In some embodiments, the composition is administered at a dose of about 2 g+/−20% to 80 g+/−20% total amino acid entities, e.g., once daily, twice daily, three times daily, four times daily, five times daily, or six times daily (e.g., twice daily). In some embodiments, the composition is administered at a dose of 10 g+/−20% to 30 g+/−20%, 20 g+/−20% to 60 g+/−20%, or 40 g+/−20% to 80 g+/−20% total amino acid entities, e.g., once daily, twice daily, or three times daily (e.g., twice per day). In certain embodiments, the composition is administered at a dose of 20 g+/−20% to 60 g+/−20% total amino acid entities twice daily, e.g., 32.55 g+/−20% total amino acid entities twice daily to a subject (e.g., to an adult subject). In certain embodiments, the composition is administered at a dose of 10 g+/−20% to 30 g+/−20% total amino acid entities twice daily, e.g., 20.1 g+/−20% total amino acid entities twice daily to a subject (e.g., to a pediatric subject).

In some embodiments, the composition is present in a unit dosage form comprising 2 g+/−20% to 15 g+/−20% of amino acid entities (e.g., 2 g+/−20%, 3 g+/−20%, 4 g+/−20%, 5 g+/−20%, 6 g+/−20%, 7 g+/−20%, 8 g+/−20%, 9 g+/−20%, 10 g+/−20%, 11 g+/−20%, 12 g+/−20%, 13 g+/−20%, 14 g+/−20%, or 15 g+/−20% of amino acid entities). In certain embodiments, the composition is present in a unit dosage form comprising 6.51 g+/−20% of amino acid entities. In certain embodiments, the composition is present in a unit dosage form comprising 8.14 g+/−20% of amino acid entities. In certain embodiments, the composition is present in a unit dosage form comprising 10.85 g+/−20% of amino acid entities. In certain embodiments, the composition is present in a unit dosage form comprising 4.02 g+/−20% of amino acid entities. In certain embodiments, the composition is present in a unit dosage form comprising 5.03 g+/−20% of amino acid entities. In certain embodiments, the composition is present in a unit dosage form comprising 6.7 g+/−20% of amino acid entities.

Production of Active Moiety and Pharmaceutical Compositions

The present disclosure features a method of manufacturing or making a composition (e.g., an Active Moiety) of the foregoing invention. Amino acid entities used to make the compositions may be agglomerated, and/or instantized to aid in dispersal and/or solubilization.

The compositions may be made using amino acid entities from the following sources, or other sources may used: e.g., FUSI-BCAA™ Instantized Blend (L-Leucine, L-Isoleucine and L-Valine in 2:1:1 weight ratio), instantized L-Leucine, and other acids may be obtained from Ajinomoto Co., Inc. Pharma. grade amino acid entity raw materials may be used in the manufacture of pharmaceutical amino acid entity products. Food (or supplement) grade amino acid entity raw materials may be used in the manufacture of dietary amino acid entity products.

To produce the compositions of the instant disclosure, the following general steps may be used: the starting materials (individual amino acid entities and excipients) may be blended in a blending unit, followed by verification of blend uniformity and amino acid entity content, and filling of the blended powder into stick packs or other unit dosage form. The content of stick packs or other unit dosage forms may be dispersed in water at time of use for oral administration.

Food supplement and medical nutrition compositions of the invention will be in a form suitable for oral administration.

When combining raw materials, e.g., pharmaceutical grade amino acid entities and/or excipients, into a composition, contaminants may be present in the composition. A composition meets a standard for level of contamination when the composition does not substantially comprise (e.g., comprises less than 10, 9, 8, 7, 6, 5, 4, 3, 2, 1, 0.15, 0.1, 0.05, 0.01, or 0.001% (w/w)) a contaminant. In some embodiments, a composition described in a method herein does not comprise a contaminant. Contaminants include any substance that is not deliberately present in the composition (for example, pharmaceutical grade amino acid entities and excipients, e.g., oral administration components, may be deliberately present) or any substance that has a negative effect on a product quality parameter of the composition (e.g., side effects in a subject, decreased potency, decreased stability/shelf life, discoloration, odor, bad taste, bad texture/mouthfeel, or increased segregation of components of the composition). In some embodiments, contaminants include microbes, endotoxins, metals, or a combination thereof. In some embodiments, the level of contamination, e.g., by metals, lecithin, choline, endotoxin, microbes, or other contaminants (e.g., contaminants from raw materials) of each portion of a composition is below the level permitted in food.

Excipients

The amino acid compositions of the present disclosure may be compounded or formulated with one or more excipients. Non-limiting examples of suitable excipients include a tastant, a flavorant, a buffering agent, a preservative, a stabilizer, a binder, a compaction agent, a lubricant, a dispersion enhancer, a disintegration agent, a flavoring agent, a sweetener, and a coloring agent.

In some embodiments, the excipient comprises a buffering agent. Non-limiting examples of suitable buffering agents include citric acid, sodium citrate, magnesium carbonate, magnesium bicarbonate, calcium carbonate, and calcium bicarbonate.

In some embodiments, the excipient comprises a preservative. Non-limiting examples of suitable preservatives include antioxidants, such as alpha-tocopherol and ascorbate, and antimicrobials, such as parabens, chlorobutanol, and phenol.

In some embodiments, the composition comprises a binder as an excipient. Non-limiting examples of suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, and combinations thereof.

In some embodiments, the composition comprises a lubricant as an excipient. Non-limiting examples of suitable lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

In some embodiments, the composition comprises a dispersion enhancer as an excipient. Non-limiting examples of suitable dispersants include starch, alginic acid, polyvinylpyrrolidones, guar gum, kaolin, xanthan gum, bentonite, purified wood cellulose, sodium starch glycolate, isoamorphous silicate, and microcrystalline cellulose as high HLB emulsifier surfactants.

In some embodiments, the composition comprises a disintegrant as an excipient. In some embodiments, the disintegrant is a non-effervescent disintegrant. Non-limiting examples of suitable non-effervescent disintegrants include starches such as corn starch, potato starch, pregelatinized and modified starches thereof, sweeteners, clays, such as bentonite, microcrystalline cellulose, alginates, sodium starch glycolate, gums such as agar, guar, locust bean, karaya, pecitin, and tragacanth. In some embodiments, the disintegrant is an effervescent disintegrant. Non-limiting examples of suitable effervescent disintegrants include sodium bicarbonate in combination with citric acid, and sodium bicarbonate in combination with tartaric acid.

In some embodiments, the excipient comprises a flavoring agent. Flavoring agents can be chosen from synthetic flavor oils and flavoring aromatics; natural oils; extracts from plants, leaves, flowers, and fruits; and combinations thereof. In some embodiments, the flavoring agent is selected from cinnamon oils; oil of wintergreen; peppermint oils; clover oil; hay oil; anise oil; eucalyptus; vanilla; citrus oil such as lemon oil, orange oil, grape and grapefruit oil; and fruit essences including apple, peach, pear, strawberry, raspberry, cherry, plum, pineapple, and apricot.

In some embodiments, the excipient comprises a sweetener. Non-limiting examples of suitable sweeteners include glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; Stevia Rebaudiana (Stevioside); chloro derivatives of sucrose such as sucralose; and sugar alcohols such as sorbitol, mannitol, xylitol, and the like. Also contemplated are hydrogenated starch hydrolysates and the synthetic sweetener 3,6-dihydro-6-methyl-1,2,3-oxathiazin-4-one-2,2-dioxide, particularly the potassium salt (acesulfame-K), and sodium and calcium salts thereof.

In some embodiments, the composition comprises a coloring agent. Non-limiting examples of suitable color agents include food, drug and cosmetic colors (FD&C), drug and cosmetic colors (D&C), and external drug and cosmetic colors (Ext. D&C). The coloring agents can be used as dyes or their corresponding lakes.

Particular excipients may include one or more of: citric acid, lecithin, (e.g. Alcolec F100), sweeteners (e.g. sucralose, sucralose micronized NF, acesulfame potassium (e.g. Ace-K)), a dispersion enhancer (e.g. xanthan gum (e.g. Ticaxan Rapid-3)), flavorings (e.g. vanilla custard #4306, Nat Orange WONF #1326, lime 865.0032U, and lemon 862.2169U), a bitterness masking agent (e.g. 936.2160U), and natural or artificial colorings (e.g. FD&C Yellow 6). Exemplary ingredient contents for each stick pack are shown in Table 5.

TABLE 5

Ingredient contents in each stick pack.

| INGREDIENT | GRADE | FUNCTION | SOURCE; COMMENT |
|---|---|---|---|
| Amino Acids | USP | Active Pharmaceutical Ingredient (API) | Various sources; Non-instantized form (MFG scale) |
| Citric Acid | USP | pH, Flavor | Spectrum Chems; f(volume) ≤ 1.0% w/v |
| Acesulfame K | NF | Sweetness (rapid onset) | Spectrum Chems; Target 1 Sweetener |
| Sucralose | NF | Sweetness (slow onset) | Spectrum Chems; WHO ADI ≤ 15 mg/kg |
| Lecithin (Alecolec F100) | FCC | Wetting Agent | American Lecithin Company |
| Xanthan Gum | FCC | Stabilizer/Thickener | TIC Gums; f (volume) ≤ 0.5% w/v |
| Vanilla Custard (Art) | GRAS | Taste/Aroma | David Michael; Mask sulfur |
| Orange (Natural and WONF) | GRAS | 1° flavor | David Michael; Citrus profile matches low pH |
| Lime (Natural and WONF) | GRAS | 2° flavor | FONA; Single flavor supplier |
| Lemon (Natural and artificial) | GRAS | 2° flavor | FONA; Single flavor supplier |
| Taste Modifier | GRAS | Bitterness masking | FONA; Useful at low volume |
| FD&C Yellow No. 6 | USP | Color | Sensient; Match flavor profile |

In another embodiment, excipients are limited to citric acid, a sweetener (e.g., sucralose), xanthan gum, an aroma agent (e.g., vanilla custard #4036), a flavoring agent (e.g., Nat orange WONF #1362), and a coloring agent (e.g., FD&C Yellow 6), e.g., the excipient specifically excludes lecithin (Table 6).

TABLE 6

Exemplary contents in each stick pack.

| INGREDIENT | GRADE | FUNCTION |
|---|---|---|
| Amino Acids | USP | Active Pharmaceutical Ingredient (API) |
| Citric Acid | USP | pH, Flavor |
| Sucralose | NF | Sweetness (slow onset) |
| Xanthan Gum | FCC | Stabilizer/Thickener |
| *Vanilla* Custard (Art) | GRAS | Aroma |
| Orange (Nat + WONF) | GRAS | 1° flavor |
| FD&C Yellow No. 6 | USP | Color |

Production of Dry Blended Preparations

To produce the dry blended preparations of the instant disclosure, the following general steps may be used: individual pharmaceutical grade amino acid entities (and, optionally, one or more excipients and/or oral administration components), may be combined into a combination and subjected to one or more blending conditions (e.g., blending and mixing). In some embodiments, the blending conditions are continued until the combination meets one or more reference standards. In some embodiments, the resulting PGDBP is divided into a plurality of portions. In some embodiments, at least a percentage of the portions of the plurality of portions also meet one or more reference standards, e.g., the reference standards that the PGDBP met. In some embodiments, at least a percentage of the portions of the plurality of portions meet one or more reference standards.

In some embodiments, the dry blended preparation, e.g., PGDBP, is also a large-scale preparation. Large-scale, as used herein, describes a preparation that is larger (e.g., by weight, mass, or volume) than a reference value. In some embodiments, the reference value is the size of a typical experimental (e.g., non-manufacturing) preparation. In some embodiments, the reference value is 10, 11, 12, 13, 14, or 15 kg. In some embodiments, large-scale preparations comprise at least 25, 30, 40, 50, 60, 70, 80, 90, 100, 120, 140, 160, 180, 200, 300, 400, 500, 600, 700, 800, 900, 1000, 2000, 3000, 4000, 5000, 6000, 7000, 8000, 9000, or 10000 kg. In some embodiments, large-scale preparations comprise no more than 10000, 5000, 1000, 900, 800, 700, 600, 500, 400, or 300 kg. In some embodiments, a large-scale preparation comprises 100-500 kg, 100-400 kg, 100-300, 100-200 kg, 200-300 kg, 200-400 kg, 200-500 kg, 300-400 kg, 300-500 kg, 400-500, or 500-1000 kg.

Blending Techniques

The methods disclosed herein comprise blending steps which blend and mix combinations of pharmaceutical grade amino acid entities to create PGDBPs that meet a reference standard. Blending conditions used by the methods described herein may utilize any known blending mechanism or combination of blending mechanisms. Blending mechanisms include convection, diffusion, and shear. Convective blending utilizes gross motion of particles, e.g., by gentle rotation within a blender/mixer. Diffusion is the slow, passive blending of particles. Shear blending pushes part of a combination of particles in one direction and another part of the combination of particles in another direction along the same parallel plane. Blending conditions used by the methods described herein may further comprise the use of granulators or other equipment to modify the size and/or shape of particles of combination components (e.g., pharmaceutical grade amino acid entities).

In some embodiments, the blending or blending condition employed by a method disclosed herein comprises convective blending. In some embodiments, the blending or blending condition employed by a method disclosed herein comprises diffusion blending. In some embodiments, the blending or blending condition employed by a method disclosed herein comprises shear blending. In some embodiments, the blending or blending condition employed by a method disclosed herein comprises convective and diffusion blending. In some embodiments, the blending or blending condition employed by a method disclosed herein comprises convective and shear blending. In some embodiments, the blending or blending condition employed by a method disclosed herein comprises diffusion and shear blending. In some embodiments, the blending or blending condition employed by a method disclosed herein comprises convective, diffusion, and shear blending.

Blending conditions used by the methods described herein may utilize any known blending or mixing equipment; blending or mixing equipment may operate based on one or more blending mechanisms. There are four main types of blending or mixing equipment: convective, hoppers (i.e., gravimetric), tumblers, and fluidization. In some embodiments, a blending condition or blending step of a method described herein may utilize one or more (e.g., 1, 2, 3, or 4) types of blending or mixing equipment. In some embodiments, dry blended preparations (e.g., PGDBPs) are prepared in batches. In some embodiments, dry blended preparations (e.g., PGDBPs) are prepared in a continuous fashion, e.g., harvesting blended/mixed preparation without interrupting blending or mixing.

The blending or mixing steps of methods disclosed herein are of duration sufficient to produce a dry blended preparation, e.g., PGDBP, which meets a reference standard. In some embodiments, the duration of the blending condition is at least 10, 15, 20, 25, 30, 35, 40, 45, 50, 55, 60, 75, 90, 105, or 120 minutes. In some embodiments, the duration of the blending condition is no more than 180, 165, 150, 135, 120, 105, 90, 75, 60, 55, 50, 45, 40, 35, 30, 25, or 20 minutes. In some embodiments, the duration of the blending condition is 20-90, 20-60, 20-50, 20-40, 20-30, 30-90, 30-60, 30-50, 30-40, 40-90, 40-60, 40-50, 50-90, 50-60, or 60-90 minutes. In some embodiments, the duration of the blending condition is 20-40 minutes, e.g., 20 minutes, 30 minutes, or 40 minutes. In some embodiments, the duration of the blending condition is sufficient that blending and mixing does not introduce heterogeneity into the combination or dry blended preparation, e.g., by over-mixing. In some embodiments, the duration of the blending condition is determined by evaluation of whether a reference standard has been met. For example, the blending condition may continue until an evaluation shows that the reference standard has been met. In some embodiments wherein the reference standard is composition uniformity, e.g., blend uniformity, evaluating whether a reference standard has been met comprises using near infrared spectroscopy (NIR). In an embodiment, the blending condition is maintained until the NIR spectrum observed shows that a standard for composition uniformity, e.g., blend uniformity, has been met.

In some embodiments, the methods disclosed herein comprise blending steps which blend and mix combinations of pharmaceutical grade amino acid entities to create PGDBPs, wherein the blending steps occur at room temperature, e.g., between 15 and 35° C., e.g., between 20 and 30° C., e.g., at about 25° C. In some embodiments, the blending steps occur at a temperature lower than 20, 21, 22, 23, 24, 25, 26, 27, 28, 29, 30, 31, 32, 33, 34, 35, 36, 37, 38, 39, or 40° C. (and optionally, at a temperature of at least 5, 6, 7, 8, 9, 10, 11, 12, 13, 14, 15, 16, 17, 18, 19, 20, 21, 22, 23, 24, or 25° C.). In some embodiments, the blending steps occur at a temperature of about 20, 21, 22, 23, 24, 25, 26, 27, 28, 29, or 30° C.

In some embodiments, the methods disclosed herein comprise blending steps which blend and mix combinations of pharmaceutical grade amino acid entities to create PGDBPs, wherein the blending steps comprise use of a blender or mixer rotation speed (e.g., a blender or mixer rotor rotational speed) of less than 10,000, 9,000, 8,000, 7,000, 6,000, 5,000, 4,000, 3,000, 2,000, 1,000, 500, 250, 100, 90, 80, 70, 60, 50, 40, 30, 20, or 10 rotations per minute (rpm) (and optionally, at least 5, 10, 15, 20, 25, 30, 35, 40, 45, 50, 60, 70, 80, 90, or 100 rpm). In some embodiments, the blending steps comprise use of a blender or mixer rotation speed (e.g., a blender or mixer rotor rotational speed) of about 20, 30, 40, 50, 60, 70, 80, 90, or 100 rpm. In some embodiments, the blending steps comprise use of a blender or mixer rotation speed (e.g., a blender or mixer rotor rotational speed) of between 5-50, 5-45, 5-40, 5-35, 5-30, 5-25, 5-20, 5-15, 5-10, 10-50, 10-45, 10-40, 10-35, 10-30, 10-25, 10-20, 10-15, 15-50, 15-45, 15-40, 15-35, 15-30, 15-25, 15-20, 20-50, 20-45, 20-40, 20-35, 20-30, 20-25, 25-50, 25-45, 25-40, 25-35, 25-30, 30-50, 30-45, 30-40, 30-35, 35-50, 35-45, 35-40, 40-50, 40-45, or 45-50 rpm.

In some embodiments, the method further comprises roller compaction and/or wet granulation. In some embodiments, the method further comprises automated filling, e.g., which incorporates direct blending, roller compaction, or wet granulation.

Segregation of different species of particles in a combination (e.g., dry blended preparation, e.g., PGDBP) during blending or mixing, division of portions, or downstream processing is a barrier to meeting and maintaining reference standards, e.g., a standard of composition uniformity. Any mixture of two or more types of particles can be vulnerable to segregation. Segregation can occur by one or more of several mechanisms, including sifting, fluidization, and dusting (e.g., see Purutyan, H, and Carson, J. W. *Predicting, diagnosing, and solving mixture segregation problems.* Jenike & Johnson, CSC Publishing, Powder and Bulk Engineering, 2013).

Sampling and Measurement

The methods described herein for manufacturing a dry blended preparation, e.g., a PGDBP, that meets a reference standard may further comprise evaluating whether the reference standard has been met. In some embodiments, the methods described herein comprise acquiring a value, e.g., for the amount of a pharmaceutical grade amino acid entity, from one or more sampling points in a dry blended preparation, e.g., PGDBP. A sampling point is a location, e.g., defined spatially and temporally, within a dry blended preparation, e.g., PGDBP. In some embodiments, to acquire a value, a sampling point may be accessed. Accessing a sampling point may comprise using a diagnostic technique on the dry blended preparation of the sampling point. In some embodiments, accessing, e.g., using a diagnostic technique, comprises stopping or pausing the blending or mixing or blending condition to access the sampling point. In some embodiments, accessing, e.g., using a diagnostic technique, does not comprise stopping or pausing the blending or mixing or blending condition to access the sampling point. Sampling points may be designated and/or accessed by methods known in the art.

In some embodiments, samples acquired from a sampling point of a combination or dry blended preparation (e.g., PGDBP) or portions of a dry blended preparation (e.g., PGDBP) may be analyzed using near-infrared (NIR) spectroscopy to acquire a value (e.g., for composition uniformity, e.g., blend uniformity). NIR spectroscopy analyzes the absorption spectra of compounds in the NIR wavelength region (780-2500 nm). Absorption peaks of compounds, e.g., pharmaceutical grade amino acid entities, are produced by molecular vibrations classified into two types: overtones and combinations. Compounds comprising CH, OH, or NH bonds can be analyzed using NIR. Methods of interpreting NIR spectra are known in the art. In some embodiments, NIR spectroscopy is used to determine whether the amounts of amino acid entities at a plurality of sampling points are similar, e.g., whether a standard for homogeneity (e.g., composition uniformity, e.g., blend uniformity) has been met. In some embodiments, the methods further comprise, responsive to the determination, selecting and/or executing a step, e.g., selecting and using a blending or mixing technique or blending condition or ending blending, mixing, or a blending condition.

In some embodiments, samples acquired from a sampling point of a combination or dry blended preparation (e.g., PGDBP) or portions of a dry blended preparation (e.g., PGDBP) may be analyzed using high performance liquid chromatography (HPLC, also referred to as high-pressure liquid chromatography) to acquire a value (e.g., for the amount of a pharmaceutical grade amino acid entity).

In some embodiments, samples acquired from a sampling point of a combination or dry blended preparation (e.g., PGDBP) or portions of a dry blended preparation (e.g., PGDBP) may be analyzed using liquid chromatography mass spectrometry (LC-MS). In some embodiments, LC-MS is used to determine the identity and/or amounts of pharmaceutical grade amino acid entities present at a sampling point or in a portion. In some embodiments, LC-MS is used to determine whether a dry blended preparation meets a standard for composition uniformity, e.g., portion or blend uniformity. In some embodiments, the methods further comprise, responsive to the amount(s) of pharmaceutical grade amino acid entities present, selecting and/or executing a step, e.g., selecting and using a blending or mixing technique or blending condition or ending blending, mixing, or a blending condition.

Reference Standards

The methods described herein produce dry blended preparations, e.g., PGDBPs, which meet one or more reference standards. A reference standard, as used herein, means: a standard used or set by:

(1) a manufacturer of a combination (e.g., dry blended preparation, e.g., PGDBP), e.g., a manufacturer having approval from a governmental agency to market the PGDBP, or (2) the pharmaceutical industry or agencies or entities (e.g., government or trade agencies or entities) regulating the pharmaceutical industry, to ensure one or more product quality parameters are within acceptable ranges for a medicine, pharmaceutical composition, treatment, or other therapeutic. A product quality parameter can be any parameter regulated by the manufacturer, pharmaceutical industry or by agencies or entities, e.g., government or trade agencies or entities, including but not limited to composition; composition uniformity; dosage; dosage uniformity; presence, absence, and/or level of contaminants or impurities; and level of sterility (e.g., the presence, absence and/or level of microbes). Exemplary government regulatory agencies include: Federal Drug Administration (FDA), European Medicines Agency (EMA), SwissMedic, China Food and Drug Administration (CFDA), or Japanese Pharmaceuticals and Medical Devices Agency (PMDA), Health Canada, and Medicines and Healthcare Products Regulatory Agency (MHRA). A product quality parameter can also be a parameter specified by a national or regional pharmacopeia or formulary, including the U.S. Pharmacopeia (USP), British Pharmacopeia (BP), National Formulary (NF), European Pharmacopeia (EP), Japanese Pharmacopeia (JP), or the International Council for Harmonisation of Technical Requirements for Pharmaceuticals for Human Use (ICH).

The one or more reference standards may be a standard used or promulgated by the pharmaceutical industry or by agencies or entities, e.g., government or trade agencies or entities, regulating the pharmaceutical industry to ensure one or more product quality parameters are within acceptable ranges for a medicine, pharmaceutical composition, treatment, or other therapeutic. The one or more reference standards may be a standard used or set by a manufacturer of a combination (e.g., dry blended preparation, e.g., PGDBP), e.g., a manufacturer having approval from a governmental agency to market the PGDBP, to ensure one or more product quality parameters are within acceptable ranges for a supplement, nutriceutical, medicine, pharmaceutical composition, treatment, or other therapeutic. A product quality parameter can be any parameter regulated by the manufacturer, or by the pharmaceutical industry or by agencies or entities, e.g., government or trade agencies or entities, including but not limited to composition; composition uniformity; dosage; dosage uniformity; presence, absence, and/or level of contaminants or impurities; level of sterility (e.g., the presence, absence and/or level of microbes), color, or particle morphology (e.g., size or shape).

Composition Uniformity

In some embodiments, the reference standard is composition uniformity. Composition uniformity, in general, is a standard of homogeneity. Composition uniformity can be classified into two different but related types of uniformity: blend uniformity and portion uniformity (portion uniformity is used interchangeably with content uniformity and dosage uniformity herein). Composition uniformity may comprise one or both types depending on the usage and context. Composition uniformity may comprise a standard of the homogeneity of a combination (e.g., dry blended preparation, e.g., PGDBP) with regards to one or a plurality of components. In some embodiments, a combination that meets a standard for composition uniformity does so with regards to one, two, three, four, or more (e.g., all) components (e.g., pharmaceutical grade amino acid entities).

Blend Uniformity

Blend uniformity refers to the level of homogeneity of the distribution of components in a combination, e.g., dry blended preparation, e.g., PGDBP. In some embodiments, a standard for composition uniformity, e.g., blend uniformity, is met when the amount of a component (e.g., a pharmaceutical grade amino acid entity) at a first sampling point in the combination (e.g., dry blended preparation, e.g., PGDBP) differs by no more than a predetermined amount from a reference value. Amounts may be absolute, e.g., grams, or relative, e.g., weight/weight (e.g., X g of the component in Y g of sampling point). Amounts may be arbitrary values, as in the case of comparing absorbance values to absorbance values or in statistical comparisons of curves, e.g., of spectra. In some embodiments, acquiring a value for blend uniformity comprises assessing a standard for composition uniformity, e.g., blend uniformity, by acquiring a value for the amount of a component at a first sampling point in the combination and comparing it to reference value.

In some embodiments, NIR is used to determine whether the amount of a component (e.g., a pharmaceutical grade amino acid entity) at a first sampling point in the combination (e.g., dry blended preparation, e.g., PGDBP) differs by no more than a predetermined amount from a second or further sampling. Using NIR, the near infrared spectrum for a sampling point can be acquired and compared to the near infrared spectrum for a second or further sampling point (e.g., a third, fourth, fifth, sixth, seventh, eighth, ninth, and/or tenth sampling point) or to the near infrared spectrum for a sample known to meet a reference standard, e.g., a standard for composition uniformity, e.g., blend uniformity. If the comparison shows that the spectra are similar enough to one another, a standard for blend uniformity is met. Similarity of NIR spectra can be evaluated by comparing the conformity index of sampling points. The conformity index is a value generated by the NIR spectra obtained, and the examples of conformity indices described are not an exhaustive list of all possible conformity indices. The conformity index may be the absorbance at a particular wavelength or wavelengths in the near infrared range. The conformity index may be the standard deviation of the average absorbance at a particular wavelength or wavelengths in the near infrared range at a plurality of sampling points. The key characteristic of the conformity index, whichever value is selected, is that the conformity indices of the sampling points accessed converge (in the case of absorbance at particular wavelength) or reduce (in the case of standard deviation) as blending/mixing time increases. For example, the conformity index may be selected to be a wavelength of X nm in the near infrared range. The absorbance at X nm will be measured at a plurality of sampling points at time points during blending. As blending continues, the absorbance at X nm at each sampling point will grow more similar to one another.

In some embodiments, the reference value is the amount of the component at a second or further sampling point (e.g., a third, fourth, fifth, sixth, seventh, eighth, ninth, and/or tenth sampling point) sampling point in the combination (e.g., dry blended preparation, e.g., PGDBP). The second sampling or further sampling point (e.g., a third, fourth, fifth, sixth, seventh, eighth, ninth, and/or tenth sampling point) point may be a different spatial location in the combination, for example, samples can be collected from a set of predetermined, spread out spatial locations, e.g., a stratified sampling plan with predetermined sites to be sampled, e.g., to obtain samples that represent a variety of locations in the blender or mixer.

In some embodiments, the second sampling point is 1, 2, 3, 4, 5, 6, 7, 8, 9, 10, or more minutes after the first sampling point. In some embodiments, multiple sampling points separated in time are taken throughout the process of manufacturing the dry blended preparation (e.g., PGDBP). In some embodiments, the sampling points separated in time are at intervals throughout the process of manufacturing the dry blended preparation (e.g., PGDBP), e.g., every 1, 2, 3, 4, 5, 6, 7, 8, 9, or 10 minutes. In some embodiments, the multiple sampling points are compared to one another (e.g., the most recent sampling points are compared to each other).

In some embodiments, a standard for composition uniformity, e.g., blend uniformity, is met when the amount of the component at a first sampling point differs from the reference value, e.g., the amount of the component at a second or further sampling point (e.g., a third, fourth, fifth, sixth, seventh, eighth, ninth, and/or tenth sampling point) by less than or equal to 1, 2, 3, 4, 5, 6, 7, 8, 9, or 10%, e.g., 10%.

In some embodiments, a standard for composition uniformity is met when the amount of a component at a first sampling differs by no more than 10% from the amount of the component at a second or further sampling point (e.g., a third, fourth, fifth, sixth, seventh, eighth, ninth, and/or tenth sampling point). In some embodiments, a standard for composition uniformity is met when the amount of a component at a first sampling differs by no more than 10% from the amount of the component present in the combination (e.g., dry blended preparation, e.g., PGDBP). In some embodiments, a standard for composition uniformity is met when the amount of a component at the most recent sampling point differs by no more than 10% from the amount of the component present at the next most recent sampling point. Values for the amount of a component present at a sampling point can comprise NIR spectra. Comparisons of values for the amount of a component present at a first, second, or further sampling point can comprise comparison of NIR spectra, e.g., overlaying NIR spectra or comparing conformity indices of the first, second, or further sampling points. Blend uniformity can be met when NIR spectra, e.g., conformity indices, reach a threshold of similarity or overlap.

Portion Uniformity

Portion uniformity refers to the homogeneity of portions of the dry blended preparation, e.g., PGDBP, with respect to amounts of components (e.g., pharmaceutical grade amino acid entities). In some embodiments, the methods described herein comprise division of a dry blended preparation (e.g., PGDBP) into a plurality of portions. In some embodiments, a standard for composition uniformity, e.g., portion uniformity, is met when the amount of a component (e.g., a pharmaceutical grade amino acid entity) in a first portion differs by no more than a predetermined amount from a reference value. Amounts may be absolute, e.g., grams, or relative, e.g., weight/weight (e.g., X g of the component in Y g of sampling point). In some embodiments, the amount of a a component (e.g., a pharmaceutical grade amino acid entity) in a first, second, or further portion (e.g., a third, fourth, fifth, sixth, seventh, eighth, ninth, or tenth portion) is determined using HPLC.

In some embodiments, the reference value is the amount of the component in a second portion. In some embodiments, the reference value is the amount(s) of the component in a plurality of portions, e.g., a plurality of test portions (e.g., the first portion is compared to a plurality of test portions). In an embodiment, the reference value is the average or median amount of the component in the plurality of test portions.

In some embodiments, a standard for composition uniformity, e.g., portion uniformity, is met when the amounts of a component (e.g., a pharmaceutical grade amino acid entity) in a plurality of test portions differ by no more than a predetermined amount from a reference value. Amounts may be absolute, e.g., grams, or relative, e.g., weight/weight (e.g., X g of the component in Y g of sampling point). In some embodiments, the reference value is the average or median amount of the component in the plurality of test portions.

In some embodiments, the reference value is the amount of the component in the combination (e.g., dry blended preparation, e.g., PGDBP). For example, the reference value can be overall weight/weight of the component present in the total combination. In some embodiments, evaluating whether a standard for composition uniformity is met comprises comparing a relative amount of a component at a first sampling point (e.g., X g of the component in Y g of sampling point) to the relative amount of the component in the combination (e.g., W g of the component in Z g of combination total); in other words, evaluating the standard for composition uniformity may comprise comparing X/Y to W/Z.

In an embodiment, at least X % of the portions of the plurality of portions of the dry blended preparation (e.g., PGDBP) are test portions, wherein X is 1, 2, 3, 4, 5, 6, 7, 8, 9, 10, 15, 20, 25, 30, 35, 40, 45, or 50. In some embodiments, no more than X % of the portions of the plurality of portions of the dry blended preparation (e.g., PGDBP) are test portions, wherein X is 50, 45, 40, 35, 30, 25, 20, 15, 10, 9, 8, 7, 6, 5, 4, 3, 2, or 1. In an embodiment, test portions are portions compared to a reference value, e.g., one another or the amount of a component present in the dry blended preparation (e.g., PGDBP), to determine whether a reference standard (e.g., for composition uniformity, e.g., portion uniformity) has been met. In some embodiments, a standard for composition uniformity, e.g., portion uniformity, is met when the amount of a component present in at least X % of test portions differs from a reference value by no more than 1, 2, 3, 4, 5, 6, 7, 8, 9, or 10%, wherein X is 50, 60, 70, 80, 85, 90, 95, 99, or 100%, and wherein the reference value is selected from the average amount of the component present in the test portions, the median amount of the component present in the test portions, or the amount of the component present in the dry blended preparation (e.g., PGDBP).

In some embodiments, portions of the dry blended preparation (e.g., PGDBP) may be stick packs or other unit dosage forms.

Level of Contamination

In some embodiments, the reference standard is level of contamination. When combining raw materials, e.g., pharmaceutical grade amino acid entities and/or excipients, into a combination, e.g., dry blended preparation, e.g., PGDBP, contaminants may be present in the combination. A combination, e.g., dry blended preparation, e.g., PGDBP, meets a standard for level of contamination when the combination does not substantially comprise (e.g., comprises less than 10, 9, 8, 7, 6, 5, 4, 3, 2, 1, 0.15, 0.1, 0.05, 0.01, or 0.001% (w/w) of) a contaminant. In some embodiments, a combination, e.g., dry blended preparation, e.g., PGDBP, comprises less than 0.15% (w/w) of a contaminant. In some embodiments, a combination, e.g., dry blended preparation, e.g., PGDBP, comprises a lower level of a contaminant than the level permissible in food (e.g., as defined by appropriate regulatory organizations known in the art). In some embodiments, a combination, e.g., dry blended preparation, e.g., PGDBP, described in a method herein does not comprise a contaminant. Contaminants include any substance that is not deliberately present in the combination, e.g., dry blended preparation, e.g., PGDBP, (for example, pharmaceutical grade amino acid entities and excipients, e.g., oral administration components, are deliberately present) or any substance that has an unintended negative effect on a product quality parameter of the PGDBP or plurality of portions of PGDBP (e.g., side effects in a subject, decreased potency, decreased stability/shelf life, discoloration, odor, bad taste, bad texture/mouthfeel, or increased segregation of components of the PGDBP). In some embodiments, contaminants include microbes, endotoxins, metals (e.g., heavy metals), residual solvents, raw material impurities, extractables, and/or leachables. In some embodiments, a combination, e.g., dry blended preparation, e.g., PGDBP, comprises a level of contaminant (e.g., does not substantially comprise a contaminant) that is compliant with a reference standard, e.g., a standard promulgated by an agency known to those of skill in the art or described herein. In some embodiments, a combination, e.g., dry blended preparation, e.g., PGDBP, comprises a level of contaminant (e.g., does not substantially comprise a contaminant) that is compliant with a standard of the ICH, e.g., the ICH Q3A Impurities in New Drug Substances standard.

In some embodiments, the methods described herein further comprise acquiring a value for the level of a contaminant at a sampling point in one or both of the combination or PGDBP. In some embodiments, the methods described herein further comprise acquiring a value for the level of a contaminant at each of a plurality of points in one or both of the combination or PGDBP, or in a test portion (e.g., of the combination or PGDBP). In some embodiments, the methods described herein further comprise acquiring a value for the level of a contaminant in a portion, e.g., a test portion, of the plurality of portions. In some embodiments, responsive to the value for the level of the contaminant, e.g., and determining that a standard for the level of contamination is met, the methods described herein further comprise selecting and executing a downstream processing step, e.g., dividing the PGDBP into portions (e.g., portioning) and fill-finish (e.g., formulation (e.g., with excipients), packaging, and labeling) and distribution. In some embodiments, responsive to the value for the level of the contaminant, e.g., and determining that a standard for the level of contamination is not met, the methods described herein further comprise selecting and executing a different downstream processing step, e.g., purification and/or removal of the contaminant or disposal of the portion, plurality of portions, or PGDBP.

Dietary Compositions

The composition (e.g., Active Moiety) including amino acid entities can be formulated and used as a dietary composition, e.g., chosen from a medical food, a functional food, or a supplement. In such an embodiment, the raw materials and final product should meet the standards of a food product.

The composition of any of the aspects and embodiments disclosed herein can be for use as a dietary composition, e.g., chosen from a medical food, a functional food, or a supplement. In some embodiments, the dietary composition is for use in a method, comprising administering the composition to a subject. The composition can be for use in a dietary composition for the purpose of improving one, two, three, four, five, six, seven, eight or more (e.g., all) of erythrocyte function, turnover, or synthesis; hemoglobin function, turnover, or synthesis; vascular function; oxidative stress (e.g., one or both of blood and systemic oxidative stress); or inflammation.

In some embodiments, the dietary composition is chosen from a medical food, a functional food, or a supplement. In some embodiments, the composition is in the form of a nutritional supplement, a dietary formulation, a functional food, a medical food, a food, or a beverage comprising a composition described herein. In some embodiments, the nutritional supplement, the dietary formulation, the functional food, the medical food, the food, or the beverage comprising a composition described herein for use in the management of a hemoglobinopathy (e.g., a subject with sickle cell disease) or a thalassemia.

The present disclosure features a method of improving one, two, three, four, five, six, seven, eight or more (e.g., all) of erythrocyte function, turnover, or synthesis; hemoglobin function, turnover, or synthesis; vascular function; oxidative stress (e.g., one or both of blood and systemic oxidative stress); or inflammation comprising administering to a subject an effective amount of a dietary composition described herein.

The present disclosure features a method of providing nutritional support or supplementation to a subject with a hemoglobinopathy (e.g., a subject with a sickle cell disease) or a thalassemia, comprising administering to the subject an effective amount of a composition described herein.

The present disclosure features a method of providing nutritional support or supplementation that aids in the management of a hemoglobinopathy (e.g., a sickle cell disease) or a thalassemia, comprising administering to a subject in need thereof an effective amount of a composition described herein.

In some embodiments, the method is a non-therapeutic method. In some embodiments, the compositions comprising the active moieties described herein are used in non-therapeutic ways, such as to provide nutrition, maintain health, or improve cosmetic appearance in healthy subjects. Examples include, but are not limited to, use of the compositions described herein as dietary supplements or as food. Compositions of the instant application can be used to nourish or maintain health of various elements in the circulatory system, such as in blood vessels, blood, erythrocytes, hemoglobin, and/or the vascular system.

The compositions can be used in methods of dietary management of a subject (e.g., a subject without a hemoglobinopathy or a thalassemia). In some embodiments, the subject does not have a hemoglobinopathy or a thalassemia.

In some embodiments, the subject is at risk of, or has been diagnosed with a hemoglobinopathy (e.g., a β-hemoglobinopathy) or a thalassemia. In certain embodiments, the hemoglobinopathy is a sickle cell disease. In certain embodiments, the thalassemia is β-thalassemia.

In some embodiments, the sickle cell disease is chosen from: sickle cell anemia (HbSS), Hemoglobin SC disease (HbSC), sickle β$^+$-thalassemia (HbS/β+), sickle β$^0$-thalassemia (HbS/β$^0$), hemoglobin SE disease, hemoglobin SD disease, or hemoglobin SO disease.

EXAMPLES

The Examples below are set forth to aid in the understanding of the inventions, but are not intended to, and should not be construed to, limit its scope in any way.

Introduction

The compositions comprising amino acid entities were tested in normal and disease-specific human primary cell models. The model systems were conducted in environments that aim to simulate physiological levels of biofluids and nutrients. These models include disease conditions (e.g., inflammation) to isolate and better understand the effects of the compositions on subsets of metabolic pathways. The high throughput nature of these models enabled the discovery of specific combinations of amino acid entities that may have beneficial, multi-pathway effects in subjects with a hemoglobinopathy (e.g., sickle cell disease) or a thalassemia (e.g. α-thalassemia or β-thalassemia).

Example 1. Cytokine Secretion in Primary Human Macrophages

Isolation of Peripheral Blood Mononuclear Cell (PBMC)

Unpurified buffy coats (Research Blood Components) were carefully poured into 50 mL centrifuge tubes and diluted with room temperature Dulbecco's Phosphate Buffered Saline (dPBS) with Calcium and Magnesium (Gibco). Diluted buffy coats were further divided into four total 50 mL centrifuge tubes at 20 mL per tube. Lymphocyte Separation Medium (Corning) was carefully pipetted to the bottom of each centrifuge tube. Mixtures were centrifuged at 850× g for 32 minutes at 20° C. with 0 deceleration and acceleration.

The PBMC layer was separated from other components after centrifugation and added to new 50 mL centrifuge tube containing 25 mL dPBS. Total volume was brought up to 50 mL with dPBS and centrifuged at 600× g for 10 minutes at 20° C. with acceleration of 9, deceleration of 5. Supernatant was carefully removed from cell pellets. The cell pellets were resuspended using 10 mL dPBS. Total volume was then brought up to 50 mL using dPBS and centrifuged at 450× g for 5 min at 20° C. with acceleration of 9, deceleration of 9. The supernatant removal and cell pellet resuspension was repeated again.

The supernatant was then carefully removed from cell pellets. Cell pellets were resuspended in 10 mL dPBS without calcium or magnesium and filtered through a 70 uM cell strainer. The total PBMC number was determined using a Cellometer K2 automated cell counter. A total of 5E6 cells were saved for flow cytometric analysis. Remaining cells were centrifuged at 490× g for 5 minutes at 20° C. with acceleration of 9, deceleration of 9.

CD14+ Cell Selection

CD14+ cells were selected using EasySep™ Human CD14 Positive Selection Kit II (STEMCELL Technologies). Cells were resuspended in cold EasySep™ Buffer (STEMCELL Technologies) at 1×10$^8$ cells/mL. A total of 100 uL/mL EasySep™ Human CD14 Positive Selection Cocktail II was added to the cell suspension, mixed, and incubated at room temperature for 10 minutes. A total of 100 uL/mL RapidSpheres were added to the mixture and incubated at room temperature for 3 minutes after mixing, then RoboSep buffer was added to bring up the total volume to 10 mL. The mixture in a 15 mL tube was placed in magnet and incubated at room temperature for 3 minutes. Supernatant was discarded and 10 mL fresh EasySep™ buffer was added to 15 mL tube. The addition of RoboSep buffer, mixing, and discarding of supernatant was was repeated two more times.

Negative and positive fractions were centrifuged at 490× g for 5 minutes at 20° C. with acceleration of 9, deceleration of 9, and resuspended in DMEM (Gibco) and 10% Heat Inactivated Fetal Bovine Serum (Atlanta Bio) and Penicillin/Streptomycin. Cells were counted and centrifuged again at 4901× g for 5 minutes at 20° C. with acceleration of 9, deceleration of 9. After centrifugation, cell were resuspended in DMEM (Gibco) and 10% Heat Inactivated Fetal Bovine Serum (Atlanta Bio) and Penicillin/Streptomycin containing 500 U/mL GM- and plated at 1-2×10$^6$ cells/mL on 10 cm tissue culture plates. Cells were kept in 37° C., 5% CO2 in between feedings/harvest.

CD14+ Cell Feeding

Cells were fed every 3-4 days by removing media and unattached cells, centrifuging at 490× g for 5 minutes at 20 C with acceleration of 9, deceleration of 9, and resuspending in fresh DMEM (Gibco) and 10% Heat Inactivated Fetal Bovine Serum (Atlanta Bio) and Penicillin/Streptomycin containing GM-CSF. Resuspended cells were seeded back onto 10 cm tissue culture plates and incubated at 37° C., 5% CO2. Differentiated macrophages were used for subsequent experiments.

Screen

Primary human PMBC derived macrophages were seeded on day 0 at 3.0E4 cells per well in 96-well microplates (ThermoFisher) in Dulbecco's Modified Eagle Medium (DMEM) (Gibco) supplemented with penicillin-streptomycin (Hyclone) and 10% heat inactivated fetal bovine serum (HI-FBS) (Atlanta Bio) and incubated overnight at 37° C., 5% CO2. On day 1, cells were washed once with 150 uL per well DPBS (Gibco) and treated with 75 uL of:

a. Amino acid free DMEM (US Biologicals) containing a defined custom amino acid concentration based on the mean physiological concentrations in blood based on values published in the Human Metabolome Database (HMDB), with 6 mM glucose, 1 mM sodium pyruvate, 10 mM HEPES, 0.2% primocin (InVivoGen); or
b. The same medium described above with one amino acid at various concentrations including complete dropout.

On day 2, cells were treated with 75 uL of the same mediums described above supplemented with 0.30 ng/mL lipopolysaccharide (LPS) (Sigma) for a final concentration of 0.15 ng/mL LPS. Control wells were treated with 1 uM BX-795 (Tocis), 1 uM TAK242 (Sigma), 0.15 ng/mL LPS, or phosphate buffered saline (PBS).

On day 3, the supernatant was collected and immediately frozen in −80° C. freezer. Cells were washed once with 150 uL DPBS and viability was assessed using the WST-8 Cell Proliferation Cytotoxicity Assay (Dojindo). Following the assay, cells were washed twice with 150 uL PBS and fixed with 4% paraformaldehyde for 5 min followed by two additional washes with 150 uL PBS. Protein levels in supernatant samples were analyzed by ELISA for IL-6 and TNFa using commercially available kits (R&D Systems) according to manufacturer-supplied protocols. Results are shown in Tables-7-12 below.

TABLE 7

IL-6 Measurements: Donor 1

| Amino Acid Supplement | | Mean | Std. Deviation | Number of values | P-value* | Significance |
|---|---|---|---|---|---|---|
| | Conc. (X) | | | | | |
| LIVRQNAC | 40 | −619.787 | 114.1592 | 3 | 0.0001 | **** |
| LIVRQNAC | 30 | −525.849 | 63.87122 | 3 | 0.0001 | **** |
| LIVRQNAC | 20 | −290.199 | 33.5584 | 3 | 0.0092 | ** |
| LIVRQNAC | 10 | 51.81434 | 183.3933 | 3 | 0.9479 | ns |
| LIVRQNAC | 1 | 0 | 148.7761 | 3 | na | na |
| LIVRQNAC + G | 40 | −1099.11 | 44.1139 | 3 | 0.0001 | **** |
| LIVRQNAC + G | 30 | −903.836 | 107.7113 | 3 | 0.0001 | **** |
| LIVRQNAC + G | 20 | −616.626 | 114.7826 | 3 | 0.0001 | **** |
| LIVRQNAC + G | 10 | −367.918 | 98.44611 | 3 | 0.0007 | *** |
| LIVRQNAC + G | 1 | 0 | 172.9553 | 3 | na | na |
| LIVRQNAC + S | 40 | −968.997 | 90.53282 | 3 | 0.0001 | **** |
| LIVRQNAC + S | 30 | −798.326 | 52.89122 | 3 | 0.0001 | **** |
| LIVRQNAC + S | 20 | −506.804 | 63.85224 | 3 | 0.0001 | **** |
| LIVRQNAC + S | 10 | −243.259 | 114.742 | 3 | 0.0365 | * |
| LIVRQNAC + S | 1 | 0 | 259.8506 | 3 | na | na |
| LIV | 40 | 4.918642 | 62.7077 | 3 | 0.9999 | ns |
| LIV | 30 | 86.01907 | 128.1151 | 3 | 0.7604 | ns |
| LIV | 20 | 112.1501 | 83.62436 | 3 | 0.564 | ns |
| LIV | 10 | 54.22668 | 63.10515 | 3 | 0.9392 | ns |
| LIV | 1 | 0 | 75.98804 | 3 | na | na |
| LIVRQ | 40 | 322.0706 | 73.87715 | 3 | 0.0033 | ** |
| LIVRQ | 30 | 297.8004 | 34.60168 | 3 | 0.0072 | ** |
| LIVRQ | 20 | 604.021 | 203.8836 | 3 | 0.0001 | **** |
| LIVRQ | 10 | 289.1798 | 57.78952 | 3 | 0.0095 | ** |
| LIVRQ | 1 | 0 | 93.58494 | 3 | na | na |
| RQNAC | 40 | −911.011 | 12.65475 | 3 | 0.0001 | **** |
| RQNAC | 30 | −766.912 | 26.23659 | 3 | 0.0001 | **** |
| RQNAC | 20 | −511.403 | 32.15983 | 3 | 0.0001 | **** |
| RQNAC | 10 | −201.63 | 6.477522 | 3 | 0.1054 | ns |
| RQNAC | 1 | 0 | 174.9658 | 3 | na | na |
| N-Acetyl Cysteine | 40 | −914.194 | 56.77271 | 3 | 0.0001 | **** |
| N-Acetyl Cysteine | 20 | −553.802 | 85.27013 | 3 | 0.0001 | **** |
| N-Acetyl Cysteine | 10 | −121.142 | 53.05191 | 3 | 0.4973 | ns |
| N-Acetyl Cysteine | 5 | 308.1772 | 263.4651 | 3 | 0.0052 | ** |
| N-Acetyl Cysteine | 0 | 0 | 45.08485 | 3 | na | na |
| | Conc. (μM) | | | | | |
| Valine | 23420 | −106.268 | 155.3559 | 3 | 0.7885 | ns |
| Valine | 11710 | −97.25 | 77.26313 | 3 | 0.8339 | ns |
| Valine | 4684 | −85.9843 | 74.99317 | 3 | 0.8841 | ns |
| Valine | 234 | 0 | 124.8497 | 3 | na | na |
| Arginine | 5440 | 357.4394 | 154.8508 | 3 | 0.0159 | * |
| Arginine | 2720 | −186.57 | 85.86105 | 3 | 0.3477 | ns |
| Arginine | 1088 | −181.36 | 131.6475 | 3 | 0.3722 | ns |
| Arginine | 109 | 0 | 282.0306 | 3 | na | na |
| Glutamine | 22484 | 440.1437 | 114.443 | 3 | 0.0022 | ** |
| Glutamine | 11242 | 397.1745 | 23.36272 | 3 | 0.0064 | ** |
| Glutamine | 3747 | 291.5443 | 81.30853 | 3 | 0.0623 | ns |

TABLE 7-continued

IL-6 Measurements: Donor 1

| Amino Acid Supplement | | Mean | Std. Deviation | Number of values | P-value* | Significance |
|---|---|---|---|---|---|---|
| Glutamine | 749 | 0 | 73.06692 | 3 | na | na |
| Isoleucine | 6639 | −218.332 | 146.5098 | 3 | 0.221 | ns |
| Isoleucine | 3320 | −15.8843 | 89.88616 | 3 | 0.9998 | ns |
| Isoleucine | 1328 | 25.98372 | 323.6109 | 3 | 0.9984 | ns |
| Isoleucine | 66 | 0 | 48.21125 | 3 | na | na |
| Leucine | 15270 | 84.46122 | 68.15253 | 3 | 0.8902 | ns |
| Leucine | 7635 | −69.9873 | 99.00843 | 3 | 0.9398 | ns |
| Leucine | 3054 | 244.9743 | 355.6551 | 3 | 0.1442 | ns |
| Leucine | 153 | 0 | 61.85589 | 3 | na | na |

Treatment with LIVRQNAC, LIVRQNAC+G, LIVRQNAC+S, RQNAC, and NAC significantly reduced LPS-induced IL-6 secretion in primary human monocyte-derived macrophages. Treatment with LIVRQ significantly increased IL-6 secretion, while LIV had no effect. Arginine and glutamine administered alone increased IL-6 secretion while other amino acids alone did not effect IL-6 secretion. Two Way ANOVA Dunnett Multiple Comparisons was performed for statistical analysis. Mean values represented as baseline subtracted values.

TABLE 8

IL-6 Measurements: Donor 2

| Amino Acid Supplement | Conc. (X) | Mean | Std. Deviation | Number of values | P-value* | Significance |
|---|---|---|---|---|---|---|
| LIVRQNAC | 40 | −27.1916 | 1.853569 | 3 | 0.0003 | *** |
| LIVRQNAC | 30 | −21.5766 | 1.709414 | 3 | 0.0045 | ** |
| LIVRQNAC | 20 | −8.20655 | 8.458638 | 3 | 0.5143 | ns |
| LIVRQNAC | 10 | −1.71581 | 6.104437 | 3 | 0.9965 | ns |
| LIVRQNAC | 1 | −2.4E−15 | 11.85079 | 3 | | |
| LIVRQNAC + G | 40 | −33.2001 | 3.55425 | 3 | 0.0001 | **** |
| LIVRQNAC + G | 30 | −30.8468 | 0.854995 | 3 | 0.0001 | **** |
| LIVRQNAC + G | 20 | −18.4318 | 4.870421 | 3 | 0.0187 | * |
| LIVRQNAC + G | 10 | 14.63551 | 21.82024 | 3 | 0.0824 | ns |
| LIVRQNAC + G | 1 | 2.37E−15 | 8.607557 | 3 | | |
| LIVRQNAC + S | 40 | −26.5993 | 2.963677 | 3 | 0.0004 | *** |
| LIVRQNAC + S | 30 | −14.2166 | 1.460268 | 3 | 0.0954 | ns |
| LIVRQNAC + S | 20 | −8.2522 | 2.917345 | 3 | 0.5095 | ns |
| LIVRQNAC + S | 10 | 8.127841 | 1.783214 | 3 | 0.5227 | ns |
| LIVRQNAC + S | 1 | 0 | 6.232673 | 3 | | |
| LIV | 40 | 34.10306 | 1.950493 | 3 | 0.0001 | **** |
| LIV | 30 | 31.10835 | 9.757211 | 3 | 0.0001 | **** |
| LIV | 20 | 20.32684 | 3.17293 | 3 | 0.0081 | ** |
| LIV | 10 | 15.10204 | 9.179111 | 3 | 0.0697 | ns |
| LIV | 1 | −7.1E−15 | 4.738966 | 3 | | |
| LIVRQ | 40 | 49.62156 | 17.37012 | 3 | 0.0001 | **** |
| LIVRQ | 30 | 42.9625 | 7.798872 | 3 | 0.0001 | **** |
| LIVRQ | 20 | 48.38603 | 13.08566 | 3 | 0.0001 | **** |
| LIVRQ | 10 | 45.99191 | 15.19687 | 3 | 0.0001 | **** |
| LIVRQ | 1 | 1.18E−15 | 6.324379 | 3 | | |
| RQNAC | 40 | −36.5521 | 1.877658 | 3 | 0.0001 | **** |
| RQNAC | 30 | −26.3768 | 0.744676 | 3 | 0.0004 | *** |
| RQNAC | 20 | −18.7428 | 1.353649 | 3 | 0.0164 | * |
| RQNAC | 10 | −3.74427 | 4.74578 | 3 | 0.9393 | ns |
| RQNAC | 1 | 2.37E−15 | 12.26314 | 3 | | |
| N-Acetyl Cysteine | 40 | −33.7585 | 0.895842 | 3 | 0.0001 | **** |
| N-Acetyl Cysteine | 20 | −24.9999 | 1.083467 | 3 | 0.0008 | *** |
| N-Acetyl Cysteine | 10 | −9.75111 | 2.381012 | 3 | 0.3617 | ns |
| N-Acetyl Cysteine | 5 | −0.79458 | 5.988677 | 3 | 0.9998 | ns |
| N-Acetyl Cysteine | 0 | −2.4E−15 | 1.900091 | 3 | | |
| | Conc. (μM) | | | | | |
| Valine | 23420 | 4.395899 | 10.35903 | 3 | 0.973 | ns |
| Valine | 11710 | −1.19605 | 7.303571 | 3 | 0.9998 | ns |
| Valine | 4684 | −4.52846 | 4.069907 | 3 | 0.97 | ns |
| Valine | 234 | −4.7E−15 | 9.361734 | 3 | | |

TABLE 8-continued

IL-6 Measurements: Donor 2

Donor 2 IL-6 Measurements

| Amino Acid Supplement | | Mean | Std. Deviation | Number of values | P-value* | Significance |
|---|---|---|---|---|---|---|
| Arginine | 5440 | −12.4164 | 0.292618 | 3 | 0.5017 | ns |
| Arginine | 2720 | −13.6102 | 2.1177 | 3 | 0.4207 | ns |
| Arginine | 1088 | −9.70116 | 9.286942 | 3 | 0.6995 | ns |
| Arginine | 109 | 2.37E−15 | 14.30728 | 3 | | |
| Glutamine | 22484 | 34.38845 | 7.467725 | 3 | 0.0026 | ** |
| Glutamine | 11242 | 63.31441 | 35.02748 | 3 | 0.0001 | **** |
| Glutamine | 3747 | 22.51543 | 9.686139 | 3 | 0.0721 | ns |
| Glutamine | 749 | 2.37E−15 | 2.203881 | 3 | | |
| Isoleucine | 6639 | −1.77438 | 10.22772 | 3 | 0.999 | ns |
| Isoleucine | 3320 | 2.305485 | 1.328015 | 3 | 0.9975 | ns |
| Isoleucine | 1328 | −2.31776 | 9.121049 | 3 | 0.9974 | ns |
| Isoleucine | 66 | 0 | 12.3413 | 3 | | |
| Leucine | 15270 | 47.59735 | 16.64049 | 3 | 0.0001 | **** |
| Leucine | 7635 | 30.46065 | 7.144005 | 3 | 0.0087 | ** |
| Leucine | 3054 | 29.60609 | 13.39676 | 3 | 0.0111 | * |
| Leucine | 153 | 7.11E−15 | 6.308577 | 3 | | |

Treatment with LIVRQNAC, LIVRQNAC+G, LIVRQNAC+S, RQNAC, and NAC significantly reduced LPS-induced IL-6 secretion in primary human monocyte-derived macrophages. Treatment with LIVRQ and LIV significantly increased IL-6 secretion. Glutamine and leucine administered alone increased IL-6 secretion, while the other amino acids alone had no effect. Two Way ANOVA Dunnett Multiple Comparisons was performed for statistical analysis. Mean values represented as baseline subtracted values.

TABLE 9

IL-6 Measurements: Donor 3

Donor 3 IL-6 Measurements

| Amino Acid Supplement | Conc. (X) | Mean | Std. Deviation | Number of values | P-value* | Significance |
|---|---|---|---|---|---|---|
| LIVRQNAC | 40 | −18.2445 | 4.129349 | 3 | 0.7529 | ns |
| LIVRQNAC | 30 | −16.8219 | 1.366045 | 3 | 0.8001 | ns |
| LIVRQNAC | 20 | −13.4826 | 12.48206 | 3 | 0.8948 | ns |
| LIVRQNAC | 10 | −34.4539 | 37.38053 | 3 | 0.2356 | ns |
| LIVRQNAC | 1 | −1.4E−14 | 14.03982 | 3 | | |
| LIVRQNAC + G | 40 | −54.4799 | 5.467815 | 3 | 0.0228 | * |
| LIVRQNAC + G | 30 | −48.3118 | 1.960574 | 3 | 0.0513 | ns |
| LIVRQNAC + G | 20 | −55.792 | 7.763897 | 3 | 0.019 | * |
| LIVRQNAC + G | 10 | −44.8309 | 14.34972 | 3 | 0.0783 | ns |
| LIVRQNAC + G | 1 | 0 | 26.01471 | 3 | | |
| LIVRQNAC + S | 40 | −14.5337 | 15.82418 | 3 | 0.868 | ns |
| LIVRQNAC + S | 30 | −25.9127 | 10.00119 | 3 | 0.479 | ns |
| LIVRQNAC + S | 20 | −25.8862 | 21.61536 | 3 | 0.48 | ns |
| LIVRQNAC + S | 10 | −11.9742 | 10.3333 | 3 | 0.9277 | ns |
| LIVRQNAC + S | 1 | −4.3E−14 | 15.34164 | 3 | | |
| LIV | 40 | 10.21257 | 37.58938 | 3 | 0.9576 | ns |
| LIV | 30 | −32.6891 | 24.862 | 3 | 0.2771 | ns |
| LIV | 20 | 27.66715 | 39.40901 | 3 | 0.4207 | ns |
| LIV | 10 | 9.44789 | 71.20002 | 3 | 0.9677 | ns |
| LIV | 1 | −4.7E−14 | 27.50075 | 3 | | |
| LIVRQ | 40 | 74.9145 | 12.55033 | 3 | 0.001 | *** |
| LIVRQ | 30 | 120.1764 | 20.21514 | 3 | 0.0001 | **** |
| LIVRQ | 20 | 77.12007 | 11.45452 | 3 | 0.0007 | *** |
| LIVRQ | 10 | 67.95483 | 43.58345 | 3 | 0.003 | ** |
| LIVRQ | 1 | −2.4E−14 | 27.62048 | 3 | | |
| RQNAC | 40 | −45.9765 | 5.740028 | 3 | 0.0683 | ns |
| RQNAC | 30 | −53.3845 | 16.45009 | 3 | 0.0265 | * |
| RQNAC | 20 | −65.6761 | 3.400465 | 3 | 0.0044 | ** |
| RQNAC | 10 | −32.8776 | 33.99103 | 3 | 0.2724 | ns |
| RQNAC | 1 | −2.8E−14 | 23.14404 | 3 | | |
| N-Acetyl Cysteine | 40 | −140.851 | 4.662272 | 3 | 0.0001 | **** |
| N-Acetyl Cysteine | 20 | −122.656 | 8.219985 | 3 | 0.0001 | **** |
| N-Acetyl Cysteine | 10 | −103.586 | 28.4385 | 3 | 0.0001 | **** |
| N-Acetyl Cysteine | 5 | −70.3269 | 8.563896 | 3 | 0.0021 | ** |
| N-Acetyl Cysteine | 0 | −9.5E−15 | 11.75797 | 3 | | |

TABLE 9-continued

IL-6 Measurements: Donor 3

| Amino Acid Supplement | Conc. (μM) | Mean | Std. Deviation | Number of values | P-value* | Significance |
|---|---|---|---|---|---|---|
| Valine | 23420 | −29.2004 | 25.98066 | 3 | 0.4329 | ns |
| Valine | 11710 | −43.8022 | 8.331697 | 3 | 0.1239 | ns |
| Valine | 4684 | −30.0609 | 8.478329 | 3 | 0.4072 | ns |
| Valine | 234 | 4.26E−14 | 17.2027 | 3 | | |
| Arginine | 5440 | −6.80983 | 0.643932 | 3 | 0.9922 | ns |
| Arginine | 2720 | −7.50318 | 22.06663 | 3 | 0.9888 | ns |
| Arginine | 1088 | 31.5786 | 70.48311 | 3 | 0.3642 | ns |
| Arginine | 109 | 0 | 17.26952 | 3 | | |
| Glutamine | 22484 | 108.5158 | 55.59202 | 3 | 0.0001 | **** |
| Glutamine | 11242 | 98.4903 | 58.37 | 3 | 0.0001 | **** |
| Glutamine | 3747 | 25.35457 | 16.40416 | 3 | 0.556 | ns |
| Glutamine | 749 | 3.79E−14 | 16.54987 | 3 | | |
| Isoleucine | 6639 | −16.3663 | 8.09174 | 3 | 0.9718 | ns |
| Isoleucine | 3320 | 0 | 19.80362 | 3 | 0.9928 | ns |
| Isoleucine | 1328 | −28.9897 | 13.10903 | 3 | 0.6593 | ns |
| Isoleucine | 66 | −6.69039 | 13.72995 | 3 | | |
| Leucine | 15270 | # | # | 3 | # | # |
| Leucine | 7635 | # | # | 3 | # | # |
| Leucine | 3054 | # | # | 3 | # | # |
| Leucine | 153 | # | # | 3 | # | # |

Leucine was not measured in Exp3 due to technical error

Treatment with LIVRQNAC+G, LIVRQNAC+S, RQNAC, and NAC significantly reduced LPS-induced IL-6 secretion in primary human monocyte-derived macrophages. Treatment with LIVRQ increased IL-6 secretion, while LIV and LIVRQNAC had no statistically significant effects on IL-6 secretion. Glutamine administered alone significantly increased IL-6 secretion, while other amino acids alone had no effect. Two Way ANOVA Dunnett Multiple Comparisons was performed for statistical analysis. Mean values represented as baseline subtracted values.

TABLE 10

TNFalpha Measurements: Donor 1

| Amino Acid Supplement | Conc. (X) | Mean | Std. Deviation | Number of values | P-value* | Significance |
|---|---|---|---|---|---|---|
| LIVRQNAC | 40 | −422.74 | 4.347575 | 3 | 0.0001 | **** |
| LIVRQNAC | 30 | −389.74 | 1.004633 | 3 | 0.0001 | **** |
| LIVRQNAC | 20 | −336.69 | 3.007435 | 3 | 0.0001 | **** |
| LIVRQNAC | 10 | −246.04 | 27.61929 | 3 | 0.0001 | **** |
| LIVRQNAC | 1 | 0 | 36.31082 | 3 | | |
| LIVRQNAC + G | 40 | −490.92 | 4.427614 | 3 | 0.0001 | **** |
| LIVRQNAC + G | 30 | −447.73 | 9.819865 | 3 | 0.0001 | **** |
| LIVRQNAC + G | 20 | −377.32 | 5.837159 | 3 | 0.0001 | **** |
| LIVRQNAC + G | 10 | −268.29 | 9.642365 | 3 | 0.0001 | **** |
| LIVRQNAC + G | 1 | 0 | 37.44353 | 3 | | |
| LIVRQNAC + S | 40 | −415.03 | 4.800449 | 3 | 0.0001 | **** |
| LIVRQNAC + S | 30 | −379.44 | 4.694868 | 3 | 0.0001 | **** |
| LIVRQNAC + S | 20 | −323.77 | 7.971135 | 3 | 0.0001 | **** |
| LIVRQNAC + S | 10 | −209.59 | 21.15676 | 3 | 0.0001 | **** |
| LIVRQNAC + S | 1 | 0 | 30.0492 | 3 | | |
| LIV | 40 | 60.37 | 20.26331 | 3 | 0.0065 | ** |
| LIV | 30 | 42.09 | 22.95664 | 3 | 0.0865 | ns |
| LIV | 20 | 63.37 | 37.24144 | 3 | 0.004 | ** |
| LIV | 10 | 45.61 | 44.71078 | 3 | 0.0556 | ns |
| LIV | 1 | 0 | 10.49958 | 3 | | |
| LIVRQ | 40 | 6.38 | 17.1283 | 3 | 0.9909 | ns |
| LIVRQ | 30 | −6.72 | 18.9622 | 3 | 0.989 | ns |
| LIVRQ | 20 | 38.38 | 39.85515 | 3 | 0.1333 | ns |
| LIVRQ | 10 | −18.95 | 10.84371 | 3 | 0.6982 | ns |
| LIVRQ | 1 | 0 | 36.96184 | 3 | | |
| RQNAC | 40 | −408.44 | 1.179877 | 3 | 0.0001 | **** |
| RQNAC | 30 | −390.41 | 1.341282 | 3 | 0.0001 | **** |

TABLE 10-continued

TNFalpha Measurements: Donor 1

Donor 1 TNFa Measurements

| Amino Acid Supplement | | Mean | Std. Deviation | Number of values | P-value* | Significance |
|---|---|---|---|---|---|---|
| RQNAC | 20 | −338.2 | 3.284307 | 3 | 0.0001 | **** |
| RQNAC | 10 | −251.35 | 4.121085 | 3 | 0.0001 | **** |
| RQNAC | 1 | 0 | 51.06933 | 3 | | |
| N-Acetyl Cysteine | 40 | −644.49 | 2.42197 | 3 | 0.0001 | **** |
| N-Acetyl Cysteine | 20 | −561.33 | 8.435064 | 3 | 0.0001 | **** |
| N-Acetyl Cysteine | 10 | −446.88 | 12.22132 | 3 | 0.0001 | **** |
| N-Acetyl Cysteine | 5 | −326.24 | 11.10173 | 3 | 0.0001 | **** |
| N-Acetyl Cysteine | 0 | 0 | 42.00516 | 3 | | |
| | Conc. (μM) | | | | | |
| Valine | 23420 | −14.98 | 20.86784 | 3 | 0.9928 | ns |
| Valine | 11710 | −41.77 | 36.61662 | 3 | 0.7784 | ns |
| Valine | 4684 | −40.37 | 32.31016 | 3 | 0.7974 | ns |
| Valine | 234 | 0 | 24.8661 | 3 | | |
| Arginine | 5440 | 62.06 | 48.80326 | 3 | 0.4786 | ns |
| Arginine | 2720 | 5.12 | 15.47951 | 3 | 0.9998 | ns |
| Arginine | 1088 | −24.33 | 17.74317 | 3 | 0.9577 | ns |
| Arginine | 109 | 0 | 18.5366 | 3 | | |
| Glutamine | 22484 | −103.07 | 27.02483 | 3 | 0.0985 | ns |
| Glutamine | 11242 | −65.24 | 23.02631 | 3 | 0.4346 | ns |
| Glutamine | 3747 | −45.7 | 28.56445 | 3 | 0.7222 | ns |
| Glutamine | 749 | 0 | 30.75138 | 3 | | |
| Isoleucine | 6639 | −40.95 | 78.56369 | 3 | 0.7896 | ns |
| Isoleucine | 3320 | −96.3 | 45.66981 | 3 | 0.1339 | ns |
| Isoleucine | 1328 | −42.68 | 21.07739 | 3 | 0.7657 | ns |
| Isoleucine | 66 | 0 | 115.9559 | 3 | | |
| Leucine | 15270 | −46.21 | 29.00402 | 3 | 0.7148 | ns |
| Leucine | 7635 | −23.04 | 40.08864 | 3 | 0.965 | ns |
| Leucine | 3054 | 42.04 | 77.19161 | 3 | 0.7746 | ns |
| Leucine | 153 | 0 | 157.6578 | 3 | | |

Treatment with LIVRQNAC, LIVRQNAC+G, LIVRQNAC+S, RQNAC, and NAC significantly reduced LPS-induced TNFa secretion in primary human monocyte-derived macrophages. Treatment with LIV increased TNFa secretion, while LIVRQ had no significant effects on TNFa secretion. None of the individually administered amino acids had an effect on TNFa secretion. Two Way ANOVA Dunnett Multiple Comparisons was performed for statistical analysis. Mean values represented as baseline subtracted values.

TABLE 11

TNFalpha Measurements: Donor 2

Donor 2 TNFa Measurements

| Amino Acid Supplement | | Mean | Std. Deviation | Number of values | P-value* | Significance |
|---|---|---|---|---|---|---|
| | Conc. (X) | | | | | |
| LIVRQNAC | 40 | −98.1341 | 2.118962 | 3 | 0.0001 | **** |
| LIVRQNAC | 30 | −85.1019 | 1.385677 | 3 | 0.0001 | **** |
| LIVRQNAC | 20 | −64.3364 | 10.07525 | 3 | 0.0001 | **** |
| LIVRQNAC | 10 | −38.3512 | 5.120689 | 3 | 0.0001 | **** |
| LIVRQNAC | 1 | 0 | 5.45587 | 3 | | |
| LIVRQNAC + G | 40 | −91.3454 | 5.994009 | 3 | 0.0001 | **** |
| LIVRQNAC + G | 30 | −82.4397 | 4.200763 | 3 | 0.0001 | **** |
| LIVRQNAC + G | 20 | −61.247 | 8.702492 | 3 | 0.0001 | **** |
| LIVRQNAC + G | 10 | −23.9913 | 7.471422 | 3 | 0.008 | ** |
| LIVRQNAC + G | 1 | −4.7E−15 | 4.578295 | 3 | | |
| LIVRQNAC + S | 40 | −74.1572 | 4.163823 | 3 | 0.0001 | **** |
| LIVRQNAC + S | 30 | −64.0016 | 5.549308 | 3 | 0.0001 | **** |
| LIVRQNAC + S | 20 | −47.5673 | 3.970363 | 3 | 0.0001 | **** |
| LIVRQNAC + S | 10 | −28.635 | 7.390447 | 3 | 0.0012 | ** |
| LIVRQNAC + S | 1 | −4.7E−15 | 7.564883 | 3 | | |
| LIV | 40 | 49.84155 | 4.092799 | 3 | **** | 0.0001 |
| LIV | 30 | 29.1118 | 14.72509 | 3 | *** | 0.001 |
| LIV | 20 | 30.17595 | 5.797518 | 3 | *** | 0.0006 |
| LIV | 10 | 16.68974 | 10.85983 | 3 | ns | 0.0974 |
| LIV | 1 | 0 | 10.41523 | 3 | | |

TABLE 11-continued

TNFalpha Measurements: Donor 2

Donor 2 TNFa Measurements

| Amino Acid Supplement | | Mean | Std. Deviation | Number of values | P-value* | Significance |
|---|---|---|---|---|---|---|
| LIVRQ | 40 | 64.1705 | 27.82953 | 3 | **** | 0.0001 |
| LIVRQ | 30 | 50.92104 | 6.955429 | 3 | **** | 0.0001 |
| LIVRQ | 20 | 45.65882 | 19.0128 | 3 | **** | 0.0001 |
| LIVRQ | 10 | 32.37038 | 19.44425 | 3 | *** | 0.0002 |
| LIVRQ | 1 | −4.7E−15 | 5.942707 | 3 | | |
| RQNAC | 40 | −84.147 | 5.821583 | 3 | **** | 0.0001 |
| RQNAC | 30 | −77.9626 | 1.626776 | 3 | **** | 0.0001 |
| RQNAC | 20 | −63.3754 | 3.494595 | 3 | **** | 0.0001 |
| RQNAC | 10 | −37.6072 | 1.88043 | 3 | **** | 0.0001 |
| RQNAC | 1 | −9.5E−15 | 4.727924 | 3 | | |
| N-Acetyl Cysteine | 40 | −103.984 | 0.720962 | 3 | 0.0001 | **** |
| N-Acetyl Cysteine | 20 | −88.6528 | 0.668195 | 3 | 0.0001 | **** |
| N-Acetyl Cysteine | 10 | −70.8382 | 12.08717 | 3 | 0.0001 | **** |
| N-Acetyl Cysteine | 5 | −54.1596 | 11.06287 | 3 | 0.0001 | **** |
| N-Acetyl Cysteine | 0 | 9.47E−15 | 2.926881 | 3 | | |
| | Conc. (µM) | | | | | |
| Valine | 23420 | −1.25079 | 12.85688 | 3 | 0.9991 | ns |
| Valine | 11710 | −0.83505 | 8.524018 | 3 | 0.9998 | ns |
| Valine | 4684 | −0.00221 | 5.127759 | 3 | 0.9999 | ns |
| Valine | 234 | −4.7E−15 | 8.717375 | 3 | | |
| Arginine | 5440 | −0.57378 | 8.672536 | 3 | 0.9999 | ns |
| Arginine | 2720 | −3.76334 | 2.467885 | 3 | 0.9594 | ns |
| Arginine | 1088 | −12.7222 | 4.764842 | 3 | 0.2488 | ns |
| Arginine | 109 | 1.42E−14 | 3.511446 | 3 | | |
| Glutamine | 22484 | 11.50181 | 6.216029 | 3 | 0.3311 | ns |
| Glutamine | 11242 | 20.03996 | 11.90208 | 3 | 0.0279 | * |
| Glutamine | 3747 | 9.338214 | 9.748253 | 3 | 0.5134 | ns |
| Glutamine | 749 | −9.5E−15 | 7.275868 | 3 | | |
| Isoleucine | 6639 | 19.25756 | 5.097831 | 3 | 0.0365 | * |
| Isoleucine | 3320 | 10.26061 | 7.861148 | 3 | 0.4307 | ns |
| Isoleucine | 1328 | 2.918887 | 1.921961 | 3 | 0.9836 | ns |
| Isoleucine | 66 | 4.74E−15 | 6.264135 | 3 | | |
| Leucine | 15270 | 46.68507 | 11.63209 | 3 | 0.0001 | **** |
| Leucine | 7635 | 41.97528 | 6.512087 | 3 | 0.0001 | **** |
| Leucine | 3054 | 31.74019 | 11.56537 | 3 | 0.0002 | *** |
| Leucine | 153 | 0 | 0.482598 | 3 | | |

Treatment with LIVRQNAC, LIVRQNAC+G, LIVRQNAC+S, RQNAC, and NAC significantly reduced LPS-induced TNFa secretion in primary human monocyte-derived macrophages. Treatment with LIV and LIVRQ increased TNFa secretion. Leucine, isoleucine, and glutamine administered individually increased TNFa secretion, while the other amino acids had no effect. Two Way ANOVA Dunnett Multiple Comparisons was performed for statistical analysis. Mean values represented as baseline subtracted values.

TABLE 12

TNFalpha Measurements: Donor 3

Donor 3 TNFa Measurements

| Amino Acid Supplement | | Mean | Std. Deviation | Number of values | P-value* | Significance |
|---|---|---|---|---|---|---|
| | Conc. (X) | | | | | |
| LIVRQNAC | 40 | −18.7507 | 2.487301 | 3 | 0.0001 | **** |
| LIVRQNAC | 30 | −15.5979 | 0.932399 | 3 | 0.0006 | *** |
| LIVRQNAC | 20 | −10.7042 | 3.013527 | 3 | 0.026 | * |
| LIVRQNAC | 10 | −8.49034 | 2.434812 | 3 | 0.1029 | ns |
| LIVRQNAC | 1 | 0 | 4.067982 | 3 | | |
| LIVRQNAC + G | 40 | −14.6552 | 3.149813 | 3 | 0.0013 | ** |
| LIVRQNAC + G | 30 | −11.6973 | 2.026588 | 3 | 0.0129 | * |
| LIVRQNAC + G | 20 | −8.0218 | 0.671662 | 3 | 0.1331 | ns |
| LIVRQNAC + G | 10 | −4.8035 | 1.658348 | 3 | 0.5453 | ns |
| LIVRQNAC + G | 1 | −2.4E−15 | 5.625453 | 3 | | |
| LIVRQNAC + S | 40 | −14.247 | 1.800575 | 3 | 0.0018 | ** |
| LIVRQNAC + S | 30 | −15.1388 | 1.568817 | 3 | 0.0009 | *** |
| LIVRQNAC + S | 20 | −12.4722 | 3.334857 | 3 | 0.0073 | ** |

TABLE 12-continued

TNFalpha Measurements: Donor 3

Donor 3 TNFa Measurements

| Amino Acid Supplement | | Mean | Std. Deviation | Number of values | P-value* | Significance |
|---|---|---|---|---|---|---|
| LIVRQNAC + S | 10 | −6.72057 | 1.833554 | 3 | 0.2549 | ns |
| LIVRQNAC + S | 1 | 0 | 4.171555 | 3 | | |
| LIV | 40 | 14.07984 | 11.14252 | 3 | 0.002 | ** |
| LIV | 30 | 1.759786 | 1.102706 | 3 | 0.9748 | ns |
| LIV | 20 | 14.51396 | 10.41503 | 3 | 0.0014 | ** |
| LIV | 10 | 8.560957 | 12.86074 | 3 | 0.0989 | ns |
| LIV | 1 | 2.37E−15 | 3.660423 | 3 | | |
| LIVRQ | 40 | 25.84453 | 0.659584 | 3 | 0.0001 | **** |
| LIVRQ | 30 | 33.74883 | 5.974096 | 3 | 0.0001 | **** |
| LIVRQ | 20 | 20.94481 | 2.163828 | 3 | 0.0001 | **** |
| LIVRQ | 10 | 15.45187 | 3.942596 | 3 | 0.0007 | *** |
| LIVRQ | 1 | 0 | 4.575346 | 3 | | |
| RQNAC | 40 | −21.5102 | 1.191926 | 3 | 0.0001 | **** |
| RQNAC | 30 | −20.8898 | 2.622446 | 3 | 0.0001 | **** |
| RQNAC | 20 | −19.9558 | 3.302225 | 3 | 0.0001 | **** |
| RQNAC | 10 | −9.09425 | 5.483242 | 3 | 0.0725 | ns |
| RQNAC | 1 | 0 | 6.189505 | 3 | | |
| N-Acetyl Cysteine | 40 | −55.3093 | 0.809363 | 3 | 0.0001 | **** |
| N-Acetyl Cysteine | 20 | −48.4373 | 1.563179 | 3 | 0.0001 | **** |
| N-Acetyl Cysteine | 10 | −41.7266 | 3.533914 | 3 | 0.0001 | **** |
| N-Acetyl Cysteine | 5 | −33.6246 | 0.253484 | 3 | 0.0001 | **** |
| N-Acetyl Cysteine | 0 | 4.74E−15 | 8.55997 | 3 | | |
| | Conc. (μM) | | | | | |
| Valine | 23420 | 3.688279 | 7.532913 | 3 | 0.8962 | ns |
| Valine | 11710 | −2.59866 | 2.586099 | 3 | 0.9674 | ns |
| Valine | 4684 | 0.126 | 0.903014 | 3 | 0.9999 | ns |
| Valine | 234 | −2.4E−15 | 2.731283 | 3 | | |
| Arginine | 5440 | −1.76662 | 4.067694 | 3 | 0.992 | ns |
| Arginine | 2720 | −0.96691 | 4.86075 | 3 | 0.9991 | ns |
| Arginine | 1088 | 3.131153 | 10.346 | 3 | 0.9384 | ns |
| Arginine | 109 | 3.55E−15 | 4.325877 | 3 | | |
| Glutamine | 22484 | 29.14034 | 17.71417 | 3 | 0.0001 | **** |
| Glutamine | 11242 | 18.00238 | 14.58602 | 3 | 0.0061 | ** |
| Glutamine | 3747 | 1.935546 | 2.127977 | 3 | 0.9887 | ns |
| Glutamine | 749 | 0 | 5.196592 | 3 | | |
| Isoleucine | 6639 | −1.66019 | 4.262718 | 3 | 0.9938 | ns |
| Isoleucine | 3320 | 3.308901 | 3.745411 | 3 | 0.9262 | ns |
| Isoleucine | 1328 | −6.22991 | 0.48195 | 3 | 0.5976 | ns |
| Isoleucine | 66 | −2.4E−15 | 3.844593 | 3 | | |
| Leucine | 15270 | # | # | 3 | # | # |
| Leucine | 7635 | # | # | 3 | # | # |
| Leucine | 3054 | # | # | 3 | # | # |
| Leucine | 153 | # | # | 3 | # | # |

Leucine was not measured in Exp3 due to technical error

Treatment with LIVRQNAC, LIVRQNAC+G, LIVRQNAC+S, RQNAC, and NAC significantly reduced LPS-induced TNFa secretion in primary human monocyte-derived macrophages. Treatment with LIV and LIVRQ increased TNFa secretion. Individually administered amino acids had no significant effect on TNFa secretion, except for glutamine which increased TNFa secretion. Two Way ANOVA Dunnett Multiple Comparisons was performed for statistical analysis. Mean values represented as baseline subtracted values.

An imbalance of pro-inflammatory and anti-inflammatory cytokine production has been proposed to correlate with the development of vasoocclusive crises (VOC) and their severity in sickle cell disease (Sarray et al. 2015; hereby incorporated by reference in its entirety). VOC are a hallmark complication of sickle cell disease resulting in ischemic injuries and severe pain. Sarray et al. (2015) demonstrated that elevations of the pro-inflammatory cytokine IL-6 correlated with duration of VOC, together with enrichment of enrichment of high IL-6 and TNFαt quartiles in the VOC group, and that reduced pro-inflammatory IL-10 correlated with VOC frequency, type, severity, and duration. Together their results highlight the importance of pro- and anti-inflammatory balance in sickle cell disease pathology.

Example 2. Reactive Oxygen Species in Sickle Cell Disease Patients

Deoxygenation of hemoglobin results in superoxide production, which is amplified when oxygen withdrawal increases such as occurs during hypoxia, reduced blood flow or anemia (Rogers et al. 2009). As such, erythrocytes require robust antioxidant defense systems and serve as a sink for systemic reactive oxygen species (ROS, Rogers et al. 2009). ROS are reported to be generated at a higher rate in whole blood and erythrocytes in sickle cell disease patients than in healthy controls and both the abundance of reduced glutathione (GSH) as well as the ability to recycle GSH are impaired, resulting in membrane protein oxidation, membrane fragility, and vascular dysfunction (Amer et al. 2003, 2004, 2005, Rogers et al. 2013).

Hydrogen Peroxide ($H_2O_2$) was used to induce ROS in samples of whole blood from healthy controls (Research Blood Components) and from sickle cell disease patients (IRB approval, Boston Children's Hospital) following a protocol adapted from Amer et al. 2004. Whole blood samples were appropriately diluted in $Ca^{2+}$- and $Mg^{2+}$-free Dulbecco's phosphate buffered saline (DPBS, Life Technologies) and the concentration of erythrocytes (RBC/ml) was measured on a Cellometer K2 Fluorescent Viability Cell Counter according to the manufacturer's RBC/AOPI protocol (Nexcelom Biosciences).

Cells were then diluted to $1*10^6$ RBC/ml into either prewarmed 37° C. DPBS or HEPES-buffered physiological solution (HPS) as adapted from Wesseling et al. (2016) containing (mM): 145 NaCl, 7.5 KCl, 10 Glucose, 10 HEPES, 2 CaCl2, pH 7.4, 0.2 filtered, and supplemented with the 20 proteogenic amino acids at 1× the basal concentrations present in the HMDB (Wishart D S, Tzur D, Knox C, et al., HMDB: the Human Metabolome Database. Nucleic Acids Res. 2007 January; 35(Database issue):D521-6. 17202168)) (Millipore Sigma). 2'-7'-dichlorofluorescin diacetate (DCF, Millipore Sigma), 20 mM in dimethyl sulfoxide (DMSO, Fisher) were added to a working concentration of 100 μM. Cells were incubated with dye for 15 minutes at 37° C., 5% CO2 in a tissue culture incubator, washed once, and resuspended in the 0.9 volumes of the same prewarmed 37° C. buffer with 5 minute spins at 500× g, accel/decal=5 in a swing arm centrifuge (Beckman Coulter). Cells were distributed into 96 well clear bottom black microplates, 90 μl/well (Corning) and then 10 al of the same buffer was added per well optionally containing individual or combinations of amino acids designed to increase their concentration by 1×, 5×, 10×, or 20× basal concentrations present in the HMDB (Human Metabolome Database (Wishart D S, Tzur D, Knox C, et al., HMDB: the Human Metabolome Database. Nucleic Acids Res. 2007 January; 35(Database issue):D521-6. 17202168)) or non-proteogenic amino acids to a final concentration of 0.1, 1, 2, or 5 mM. Where possible due to solubility constrains, pH-7.4-adjusted stock solutions of amino acids were used. Wells were mixed by pipetting and plates incubated at 37° C., 5% $CO_2$ in a tissue culture incubator for 30 minutes. Optionally, 40 mM $H_2O_2$(Millipore Sigma) freshly prepared in the same buffer was added to bring the concentration to 2 mM, wells mixed by pipetting, and plates were incubated an additional 30, 60, 120, or 240 minutes before fluorescence measurement of ROS signal on a Synergy H4 (BioTek) microplate reader with excitation=488 nm and emission=530 nm, and gain either set to autogain, 75, or 100.

N-acetylcysteine (Spectrum) and cysteine reduced ROS measured in whole blood of healthy control donors treated with $H_2O_2$ in a dose-responsive fashion and in samples of sickle cell disease patient blood both treated with $H_2O_2$ and untreated in DPBS. Additionally, 10× tryptophan increased ROS signal in both healthy donor blood and sickle cell disease patient blood, providing evidence for its exclusion from the composition. All other amino acids tested did not affect ROS measurement either alone or in combination with NAC or cysteine, showing that their inclusion in the composition were not detrimental for combating pathological oxidative stress in sickle cell disease.

Example 3. Amino Acid Profiling of Erythrocytes

Concentration differences in plasma and erythrocyte amino acids in sickle cell disease have been described and are thought to contribute to endothelial dysfunction. For example, release of erythrocyte arginase through hemolysis has been described to contribute to lower plasma arginine, contribute to limited bioavailability of this amino acid and a pathological state of nitric oxide (NO) resistance (Morris et al. 2005). Metabolomics studies have also identified amino acid level and pathway dysregulation, hypothesized to contribute to disease pathology (Darghouth et al. 2011).

Plasma and erythrocyte amino acids, as well as oxidized and reduced glutathione, will be analyzed in sickle cell disease patient whole blood samples (IRB approval, Boston Children's Hospital) as well as in whole blood from race-matched healthy controls. While it is not possible to control for fed or fasted state at the time when samples are taken, statistical differences between erythrocyte and plasma amino acid concentrations in patients and healthy controls are thought to represent robust differences in metabolism in the disease state and may contribute to disease pathology. Amino acid for which differences are observed between healthy controls and sickle cell disease patients at either trend level or statistical significance will be prioritized for screening in other assays such as resistance to sickling under hypoxia and exposure of adhesion markers such as phosphatidylserine.

Example 4. Adhesion Biomarkers

The hallmark of sickle cell disease is the "sickle cell crisis," caused by vaso-occlusion of small blood vessels that lead to ischemic injuries and severe pain. A number of factors conspire toward vaso-occlusion: increased rigidity and adhesion of sickle RBCs make them more likely to stick to circulating WBCs and the vascular endothelium; increased arginase from hemolysis depletes free plasma arginine necessary to generate nitric oxide (NO), impairing vasodilation. Sickle cell crises are the primary reason that patients seek medical care, and can be life threatening as they can occur in any organ and last for several days. Crises in the pulmonary vasculature manifest as "acute chest syndrome;" those in the brain can cause stroke or "silent" cerebral infarcts; those in bone can lead to osteonecrosis; and crises elsewhere can lead to damage and failure in nearly any organ. Sickling leads to physical disruption and increased turnover of the erythrocyte membrane, increased cell rigidity, cell dehydration through loss of potassium, and increased RBC adhesion via externalization of phosphatidylserine. Red blood cell adhesion to leukocytes and to vascular endothelial cells, mediated by increased phosphatidylserine exposure, is among the mechanisms of vaso-occlusion in sickle cell disease, and measurement of phosphatidylserine exposure correlates well with other assays of adhesion such as erythrocyte adhesion to human umbilical vein epithelial cells.

Phosphatidyl serine exposure will be measured by binding of Annexin V conjugated to the fluorescent probe Alexa 488 (Life Technologies), either in untreated sickle cell disease patient blood (IRB approval, Boston Children's Hospital), healthy control donor blood (Research Blood Components) under untreated conditions or when treated with a disease-pathology-relevant stimulus known to provoke phosphatidylserine exposure such as hypoxia or the calcium ionophore 4-br A23187 (Millipore Sigma). The ability of amino acid treatments at multiples of the basal levels found in the HMDB (Human Metabolome Database (Wishart D S, Tzur D, Knox C, et al., HMDB: the Human Metabolome Database. Nucleic Acids Res. 2007 January; 35(Database issue): D521-6. 17202168)) to modify phosphatidylserine exposure will be observed under these conditions. Individual or combinations of amino acids able to reduce exposure of the adhesion marker phosphatidylserine will be potential therapeutics for reduction of vaso-occlusion.

Example 5. Resistance of Erythrocytes to Sickling

Under hypoxic conditions, such as in peripheral tissues, or during anemia, sickle cell disease erythrocytes change their morphology to the characteristic "sickle" shape due to polymerization of sickle hemoglobin (HbS). This increases cell rigidity and contributes to vaso-occlusion (Du et al. 2015). Potential treatments that provide resistance to sickling either by decreasing the proportion of cells that sickle under hypoxia, as has been shown for hydroxyurea, or by increasing the time cells take to sickle, could reduce vaso-occlusion pathology.

Single amino acids and combinations at multiples of the basal levels found in the HMDB (Human Metabolome Database (Wishart D S, Tzur D, Knox C, et al., HMDB: the Human Metabolome Database. Nucleic Acids Res. 2007 January; 35(Database issue):D521-6. 17202168)) will be tested for their ability to provide sickle cell disease patient whole blood samples diluted in appropriate buffer with resistance to sickling under incubation in a hypoxic gas mixture (2% $O_2$, 5% $CO_2$, balance $N_2$, Middlesex Gasses & Technologies). Samples will be imaged in a 96-well black fluorescence microplate with optical bottom (Thermo Fisher) over a time course on an ImageExpress Micro Confocal microscope (Molecular Devices), and the percentage of sickled cells will be identified at each time point. Amino acids or combinations imparting resistance to sickling will be considered for inclusion in the composition against a body of evidence for these amino acids.

Example 6. Calcium Influx of Erythrocytes

Sickle cell erythrocytes are described as having a persistent calcium leak, exacerbated under hypoxia and sickling, resulting in exposure of adhesion markers such as phosphatidylserine and contributing to disease pathology.

Calcium influx into sickle cells will be measured by pre-loading sickle cell disease patient whole blood with the intracellular calcium probe Fluo-4 AM (Life Technologies) according to the manufacturer's instructions. Single amino acids and combinations at multiples of the basal levels found in the HMDB (Human Metabolome Database (Wishart D S, Tzur D, Knox C, et al., HMDB: the Human Metabolome Database. Nucleic Acids Res. 2007 January; 35(Database issue):D521-6. 17202168)) will be tested for their ability to provide sickle cell disease patient whole blood samples diluted in appropriate buffer with resistance to calcium influx under incubation in a hypoxic gas mixture (2% $O_2$, 5% $CO_2$, balance $N_2$, Middlesex Gasses & Technologies). Samples will be imaged in a 96-well black fluorescence microplate with optical bottom (Thermo Fisher) over a time course on an ImageExpress Micro Confocal microscope (Molecular Devices), and calcium influx will be measured by observing fluorescence intensity with excitation=488 nm emission=530 nm of either those erythrocytes with sickle phenotype or all cells.

Example 7. Berkeley Mouse Model of Sickle Cell Anemia

Several transgenic mouse models have been developed to examine the systems-nature pathology and treatment of sickle cell disease. One such model called the Berkeley mouse (BERK) was developed to exclusively express human hemoglobin chains, including the sickle hemoglobin variant (HbS), which leads to sickle cell anemia in these mice (Paszty C et al, 1997. Science). The BERK model well approximates many different facets of the disease, including: anemia, reticulocytosis, irreversibly sickled cells, increased red blood cell turnover, and multi-organ pathology (de Jong K et al, 2001. Blood).

Combinations of amino acids at multiples of the basal levels found in the HMDB (Human Metabolome Database (Wishart D S, Tzur D, Knox C, et al., HMDB: the Human Metabolome Database. Nucleic Acids Res. 2007 January; 35(Database issue):D521-6. 17202168)) will be tested against placebo and multiple levels of L-glutamine for their systems-therapeutic effect in the BERK mouse model. Animals will be gavaged BID for 4 weeks in one of six treatment arms: (1) vehicle, (2) low dose L-glutamine, (3) high dose L-glutamine, (4) low dose composition consisting of L R Q NAC G Car H K V, (5) high dose composition consisting of L R Q NAC G Car H K V, or (6) high dose composition consisting of L R Q NAC. Weekly blood draws from tail vein puncture will be analyzed for hematological parameters (complete blood count), including but not limited to hematocrit, hemoglobin, erythrocyte volume, reticulocyte count, WBC count, and platelet count. Blood draws will be also analyzed for plasma and RBC amino acid profiles, cytokine panels, ROS, PS exposure, and other relevant cell or molecular markers. Biotinylation of red blood cells prior to blood draws and analysis by flow cytometry will allow for quantification of red blood cell turnover. Histopathology will allow for comparison of organ damage in control and treatment groups. Combinations of amino acids that improve hematological parameters, erythrocyte health and turnover, and limit organ damage will provide support for therapy in sickle cell anemia.

Example 8. RBC Deformability Studies in an Ex Vivo Induced Model of Hemolysis with Amino Acids Pre-Treatment Whole blood from healthy African American and/or Hispanic donors was obtained from Research Blood Components, LLC based on the following donor selection criteria: Adult age (between 18 and 50 years), normal BMI (<30), and absence of other confounding clinical conditions. Whole blood from SCD donors were obtained from BioIVT based on the following donor selection criteria: Patients with genotypes HbSS, HbSC, HbS/$\beta^0$ and at least 1-2 months gap since last blood transfusion. Whole blood was shipped on ice on the same day as blood draw. Upon receipt, the blood sample was aliquoted and stored in the refrigerator until used for studies.

RBC deformability measurements were conducted with the Laser Optical Rotational Red Cell Analyzer (LORRCA) from RR Mechatronics in a temperature-controlled environment (37° C.). Briefly, an even layer of RBCs suspended in polyvinylpyrrolidone (PVP) is subjected to shear stress gradient (0.3 to 30 Pa) through two concentric cylinders and the resulting changes in RBC shape or deformability are measured by a laser beam diffraction pattern. The captured images of RBC shape in response to increasing shear stress are then analyzed by the LORRCA program to calculate Elongation Index (EI).

Healthy RBCs have higher deformability≥0.5 EI and SCD RBCs have lower deformability or EI values as studied by LORRCA ektacytometry in the field. It has been suggested in prior literature that changes at ½ $EI_{max}$ shear stress≤1.69

Pa indicate change in RBC membrane flexibility and at shear stress≥3.0 Pa indicate impact on RBC cell surface/volume ratio, intracellular viscosity along with membrane flexibility (Renoux C, et al, Sci Rep. 2019 May 1; 9(1):6771). The induced hemolysis model in this disclosure involves use of tert-butyl hydroperoxide (TBHP) to lower EI of RBCs. TBHP has been shown to permeabilize membrane, oxidize cells, induce proteolysis, inhibit enzyme activities and induce hemolysis, thus simulating the pathology of SCD (Roy A, et al, Pathophysiology. 2012 April; 19(2):137-48 and Runge-Morris M, et al, Chem Res Toxicol. 1989 March-April; 2(2):76-83).

The ex vivo hemolysis study disclosed here involves overnight treatment of whole blood with vehicle as a control and specific amino acids followed by rapid oxidation (5 min) with TBHP. Method for oxidation of whole blood with tert-butyl hydroperoxide has been used in prior literature (Diederich L, et al, Front Physiol. 2018 May 11; 9:332). RBC deformability or shape changes are then measured with LORRCA ektacytometry.

Whole blood aliquots stored in the fridge were brought up to room temperature while gently shaking on a rocker at low speed for an hour to ensure gradual and uniform suspension of red blood cells prior to deformability measurements. Vehicle control used in the study was 1× Dulbecco's Phosphate vehicle) and amino acids disclosed herein were added (at either final 10× or 2.5 mM concentration as indicated) to corresponding vehicle and amino acid treatment conditions. The samples were then incubated overnight at 37° C. Next day, 25 µL of whole blood was taken from each treatment condition and added to 5 mL Elon ISO viscous solution from RR Mechatronics. The sample was inverted 15-20 times to ensure proper mixing of the treated RBCs with the Elon ISO solution followed by loading the sample on LORRCA and capturing RBC deformability or shape measurements over the applied shear gradient. The remaining whole blood treatments were returned to incubator (37° C.) until deformability measurements were completed for all treatments. To the remaining whole blood treatment samples, TBHP solution (5.0-6.0 M in Decane, Sigma) was added at 2.5 mM final concentration from a 100 mM freshly prepared stock and incubated for further 5 min at 37° C. 25 µL of this TBHP-treated sample was immediately removed at the end of the 5 min incubation and added to the Elon ISO solution for RBC deformability measurement after oxidation. Included in the Tables 13-15 are EI measurements at ½ $EI_{max}$ shear stress 1.69 Pa and $EI_{max}$ shear stress 30 Pa from these studies and FIG. 1 captures EI measurements for all shear stress points for the indicated treatment conditions.

Results
RBC Deformability or Elongation Index (EI) Measurement in the Ex Vivo Hemolysis Model FIG. 1 shows changes in healthy RBC deformability from healthy donor 1 with and without TBHP oxidation of whole blood for the indicated pre-treatments with specific amino acids disclosed herein or DPBS vehicle. The RBC deformability measurements are shown on Y-axis in terms of EI and the applied shear stress (Pa) is shown on X-axis. The EI measurement for each shear stress is a mean of 50 measurements. Solid lines represent overnight pre-treatments of whole blood without TBHP oxidation and dot-dashed lines represent after TBHP oxidation.

Table 13 captures RBC deformability measurements (EI) at half max shear stress (1.69 Pa) and max shear stress (30 Pa) from FIG. 1. Two different fold changes are shown in Table 13. EI Fold Change with Tert-butyl Hydroperoxide shows difference in EI with and without TBHP oxidation for each pre-treatment group. RBC deformability of vehicle control at ½ $EI_{max}$ shear stress (1.69 Pa) is reduced by 4.7-fold when treated with TBHP and at $EI_{max}$ (30 Pa) is reduced by 2.0-fold. Fold change in RNacCitQCar pre-treatment group had respectively 2.9-fold and 1.5-fold decreases in RBC EI with TBHP oxidation for both shear stress points. RNacCitQCarLHKVS pre-treatment group had lowest fold change with TBHP oxidation of 1.8-fold and 1.2-fold for the two shear stress points. EI Fold Change Relative to Vehicle shows difference in EI relative to vehicle control group. RNacCitQCarLHKVS pre-treatment group has the highest improvement in ½ $EI_{max}$ and $EI_{max}$ over vehicle group for TBHP oxidation by 2.6- and 1.9-folds respectively followed by RNacCitQCar group. Results from FIG. 1 and Table 13 suggest lower EI with TBHP oxidation for all pre-treatment conditions with lowest EI for vehicle, higher EI for RNacCitQCar and highest EI for RNacCitQCarLHKVS suggesting benefit of these amino acid compositions in minimizing loss of deformability or EI upon oxidative and hemolytic damage to RBCs.

Results from Table 14 show deformability for single amino acid treatments upon TBHP oxidation in healthy whole blood from healthy donor 2. The EI for R, Cit, Nac, Q, Car single amino acid treatments over vehicle control is higher than the vehicle for both ½ $EI_{max}$ and $EI_{max}$ measurements. Q treatment group was least effective and RNacCitQCarLHKVS was most effective among all treatment groups as shown by both, individual EI measurements for ½ $EI_{max}$, $EI_{max}$ and the fold change or EI improvement relative to vehicle control. Additionally, both healthy donors 1 and 2 show highest EI with TBHP oxidation for RNacCitQCarLHKVS pre-treatment groups based on Tables 13 and 14. Results from Table 16 additionally show effect of RNacCit in whole blood from healthy donor 2. EI of RBCs pre-treated with RNacCit shows 1.8-fold better deformability than vehicle at ½ $EI_{max}$ shear stress and about 1.5-fold better at $EI_{max}$ in response to TBHP oxidation.

Results from Table 15 show linear increase in deformability or EI in RBCs from an SCD donor when pre-treated ex vivo with increasing doses of amino acids RNacCitQCarLHKVS followed by rapid TBHP oxidation. Fold change in RBC deformability or EI shows dose response for 5×, 10× and 20× RNacCitQCarLHKVS pre-treatments relative to vehicle control with highest 5.3-fold change observed for 20× pre-treatment.

Combined results from Tables 13-15 and FIG. 1 demonstrate benefit of specific amino acid compositions disclosed herein in reducing loss of RBC deformability or shape as measured by EI in response to damage from oxidation, proteolysis and hemolysis. Reduction in hemolysis could potentially minimize vaso-occlusive pain crises and organ damage in sickle patients.

TABLE 13

RBC elongation index (EI) and fold change with TBHP oxidation of healthy whole blood (healthy donor 1) pretreated with amino acids relative to vehicle

| Pre-treatment (10X Amino Acids/2.5 mM Nac, Cit, Car) | TBHP Addition (2.5 mM) | Elongation Index (EI) | | EI Fold Change with TBHP | | EI Fold Change Relative to Vehicle | |
|---|---|---|---|---|---|---|---|
| | | ½ $EI_{max}$ (1.69 Pa) | $EI_{max}$ (30 Pa) | ½ $EI_{max}$ (1.69 Pa) | $EI_{max}$ (30 Pa) | ½ $EI_{max}$ (1.69 Pa) | $EI_{max}$ (30 Pa) |
| Vehicle | − | 0.336 | 0.520 | 4.67 | 2.03 | 1.00 | 1.00 |
| | + | 0.072 | 0.255 | | | 1.00 | 1.00 |
| RNacCitQCar | − | 0.306 | 0.545 | 2.85 | 1.47 | 0.91 | 1.04 |
| | + | 0.107 | 0.370 | | | 1.48 | 1.45 |
| RNacCitQCarLHKVS | − | 0.336 | 0.561 | 1.76 | 1.16 | 1.00 | 1.07 |
| | + | 0.190 | 0.482 | | | 2.63 | 1.89 |

TABLE 14

RBC elongation index (EI) and fold change with TBHP oxidation of healthy whole blood (healthy donor 2) pretreated with amino acids relative to vehicle

| Pre-treatment (10X Amino Acids/2.5 mM Nac, Cit, Car) + 2.5 mM TBHP | Elongation Index (EI) | | EI Fold Change Relative to Vehicle | |
|---|---|---|---|---|
| | ½ $EI_{max}$ (1.69 Pa) | $EI_{max}$ (30 Pa) | ½ $EI_{max}$ (1.69 Pa) | $EI_{max}$ (30 Pa) |
| R | 0.057 | 0.251 | 1.35 | 2.14 |
| Nac (2.5 mM) | 0.056 | 0.245 | 1.33 | 2.09 |
| Cit (2.5 mM) | 0.053 | 0.255 | 1.26 | 2.17 |
| Q | 0.033 | 0.181 | 0.78 | 1.54 |
| Car (2.5 mM) | 0.048 | 0.210 | 1.14 | 1.79 |
| RNacCitQCar | 0.047 | 0.222 | 1.12 | 1.89 |
| RNacCitQCarLHKVS | 0.066 | 0.302 | 1.57 | 2.58 |
| Vehicle | 0.042 | 0.117 | 1.00 | 1.00 |

TABLE 15

RBC elongation index (EI) with TBHP oxidation of sickle whole blood pretreated with different doses of amino acids RNacCitQCarLHKVS

| RNacCitQCarLHKVS Pre-treatment (10X Amino Acids/Nac, Cit and Car corresponding to 2.5 mM) + 2.5 mM TBHP | Elongation Index $EI_{max}$ (30 Pa) | EI Fold Change Relative to Vehicle |
|---|---|---|
| Vehicle or 0X | 0.014 | 1.00 |
| 5X | 0.024 | 1.71 |
| 10X | 0.061 | 4.35 |
| 20X | 0.074 | 5.28 |

TABLE 16

RBC elongation index (EI) and fold change with TBHP oxidation of healthy whole blood (healthy donor 2) pretreated with amino acids relative to vehicle

| Pre-treatment (10X Amino Acids/2.5 mM Nac, Cit, Car) + 2.5 mM TBHP | Elongation Index (EI) | | EI Fold Change Relative to Vehicle | |
|---|---|---|---|---|
| | ½ $EI_{max}$ (1.69 Pa) | $EI_{max}$ (30 Pa) | ½ $EI_{max}$ (1.69 Pa) | $EI_{max}$ (30 Pa) |
| R | 0.087 | 0.308 | 1.02 | 1.00 |
| Nac (2.5 mM) | 0.096 | 0.337 | 1.13 | 1.10 |
| Cit (2.5 mM) | 0.095 | 0.327 | 1.11 | 1.06 |
| RNacCit | 0.154 | 0.452 | 1.81 | 1.47 |
| Vehicle | 0.085 | 0.306 | 1.00 | 1.00 |

Example 9. Endothelial Cell Screening

Vascular dysfunction in SCD can manifest in the expression of vascular endothelial cell (VEC) adhesion markers, inflammatory cytokines, and reduced synthesis of nitric oxide (NO) and NO-dependent endothelial function. This multi-faceted pathology can contribute to decreased blood perfusion and an increased likelihood of acute vaso-occlusive events or progressive organ damage.

A VEC model was employed to assess the ability of amino acids to influence aspects of vascular dysfunction in SCD. TNFa treatment of healthy donor HLMVEC mimics the SCD disease state and induces expression of adhesion markers ICAM-1 and VCAM-1, and secretion of proinflammatory cytokine IL-6. It is established that levels of ICAM-1, VCAM-1, and IL-6 can contribute to SCD pathology and correlate with the incidence and severity of complications in SCD patients. The VEC model sought to test the ability of amino acids to reduce the TNFa-induced disease phenotype by lowering expression of adhesion markers (ICAM-1 and VCAM-1) and inflammatory cytokines (IL-6) while promoting VEC health and viability.

Primary Human Lung Microvascular Endothelial Cells (HLMVEC; Lonza) were seeded at 6,000 cells per well in Endothelial Cell Growth Basal Medium-2 (Lonza) supplemented with Fetal Bovine Serum (FBS; Lonza), human EGF (Lonza), human VEGF (Lonza), R3-Insulin-like Growth Factor-1 (Lonza), ascorbic acid (Lonza), hydrocortisone (Lonza), human FGF-beta (Lonza), and gentamicin/amphotericin-b (Lonza) in a 96-well plate (Thermo Fisher). The cells were incubated for 45 minutes at room temperature, then incubated overnight at 37° C./5% $CO_2$.

Following overnight incubation, cell were washed once with 150 μL of Dulbecco's phosphate buffered saline (DPBS; Gibco), and then treated with Endothelial Basal Medium MCB-131 (amino acid, glucose, sodium pyruvate, and phenol red free; US Biologicals) containing a defined custom amino acid concentration based on physiological concentrations in blood of patients with SCD (thus recapitulating observed metabolic imbalances such as the depletion of certain essential amino acids including arginine and aspartate and enrichment of certain non-essential amino acids including glutamate and asparagine), dialyzed FBS (Hyclone), human EGF (Lonza), human VEGF (Lonza), R3-Insulin-like Growth Factor-1 (Lonza), ascorbic acid (Lonza), hydrocortisone (Lonza), human FGF-beta (Lonza), and gentamicin/amphotericin-b (Lonza), glucose, 10 mM HEPES, sodium pyruvate, and sodium bicarbonate supplemented with one of the following:

a. PBS (vehicle control),
b. 0.5 ng/mL Tumor Necrosis Factor alpha (TNFα) and PBS, or;
c. 0.5 ng/mL TNFα and amino acid treatments at 20× mean physiological concentrations in plasma based on values published in the Human Metabolome Database (HMDB) in PBS.

After 24 hours of treatment, cells were washed once with 150 μL of DPBS (Gibco), then fixed with 4% paraformaldehyde. Following fixation, cells were stained with anti-ICAM-1 [MEM-111] (mouse IgG2a anti-human; abcam) and anti-VCAM1 [1.4C3] (mouse IgG1, κ anti-human; abcam) primary antibodies at 1000×, and 100× dilutions respectively. Cells were then stained with Goat anti-Mouse IgG2a Cross-Adsorbed Secondary Antibody, Alexa Fluor 594 (Invitrogen) and Goat anti-Mouse IgG1 Cross-Adsorbed Secondary Antibody, Alexa Fluor 647(Invitrogen) secondary antibodies. Nuclei were stained with Hoechst 3342 (Life Technologies).

Antibody binding was detected by fluorescence microscopy using a high content imager (Molecular Devices). Images were analyzed using MetaXpress 6 software to determine the integrated intensity per cell for each wavelength corresponding to ICAM-1 or VCAM-1.

Supernatants were analyzed for IL-6 concentrations using a Human Cytokines FirePlex-HT Panel 1 kit (abcam) according to the manufacturer-supplied instructions. Particles were imaged on a high content imager (Molecular Devices), and results were interpolated from a standard curve with FirePlex Analysis Workbench Software (abcam) according manufacturer's recommendations.

TABLE 17

Specific amino acid compositions reduced levels of secreted IL6 in HLMVEC treated with TNFa

| Amino Acid Supplement [Conc.]* | Secreted IL6 | | |
|---|---|---|---|
| | Median | p-Value | Metarank |
| Arg [20x] | −0.224 | 0.0569 | 19 |
| Car [5 mM] | −0.022 | 0.3751 | 24 |
| Cit [5 mM] | −0.270 | 0.0754 | 16 |
| CitNac [5 mM] | −0.321 | 0.1961 | 15 |
| Gln [20x] | 0.043 | 0.7304 | 28 |
| Gly [20x] | −0.010 | 0.9533 | 26 |
| His [20x] | −0.198 | 0.6232 | 22 |
| LIV [20x] | −0.227 | 0.2337 | 17 |
| LRQNac [20x/5 mM] | −0.346 | 0.0301 | 13 |
| LRQNacCit [20x/5 mM] | −0.332 | 0.0758 | 14 |
| Leu [20x] | −0.491 | 0.0072 | 7 |
| Lys [20x] | 0.132 | 0.6119 | 29 |
| Nac [5 mM] | −0.497 | 0.0090 | 6 |
| Orn [20x] | −0.378 | 0.4054 | 11 |
| RCit [20x] | 0.029 | 0.6405 | 27 |
| RCitNac [20x/5 mM] | −0.870 | 0.0313 | 1 |
| RCitNacQCar [20x/5 mM] | −0.831 | 0.0531 | 3 |
| RCitNacQCarLHKVS [20x/5 mM] | −0.465 | 0.0461 | 9 |
| RNac [20x/5 mM] | −0.445 | 0.0911 | 10 |
| RQNac [20x/5mM] | −0.770 | 0.0339 | 4 |
| Ser [20x] | −0.153 | 0.4493 | 23 |
| Trp [20x] | −0.357 | 0.0723 | 12 |
| Val [20x] | −0.224 | 0.0553 | 18 |

HLMVEC treated with amino acid compositions comprising RCitNac or RCitNacQCar greatly reduced IL-6 secretion from TNF-α treated cells. RQNac also reduced IL-6 secretion. RCitNacQLHKVS moderately reduced secreted levels of IL-6.

TABLE 18

Specific amino acid compositions reduced levels of ICAM-1 and VCAM-1 Cell Integrated Intensity in HLMVEC treated with TNFa

| Amino Acid Supplement [Conc.]* | ICAM-1 Cell Integrated Intensity | | VCAM-1 Cell Integrated Intensity | | Meta-Rank |
|---|---|---|---|---|---|
| | Median | p-Value | Median | p-Value | |
| Arg [20x] | −0.046 | 0.9977 | −0.001 | 0.7376 | 12.5 |
| Car [5 mM] | −0.013 | 0.5476 | −0.017 | 0.5354 | 12.5 |
| Cit [5 mM] | −0.118 | 0.0150 | −0.157 | 0.0018 | 8 |
| CitNac [5 mM] | −0.249 | 0.1532 | −0.275 | 0.3477 | 4 |
| Gln [20x] | 0.237 | 0.0454 | 0.372 | 0.0159 | 29 |
| Gly [20x] | −0.261 | 0.0375 | −0.298 | 0.0434 | 3 |
| His [20x] | 0.084 | 0.0366 | 0.109 | 0.0461 | 18.5 |
| LIV [20x] | 0.172 | 0.1098 | 0.172 | 0.0904 | 25 |
| LRQNac [20x/5 mM] | 0.142 | 0.2944 | 0.084 | 0.4009 | 20 |
| LRQNacCit [20x/5 mM] | 0.089 | 0.3654 | 0.114 | 0.2541 | 20 |
| Leu [20x] | 0.086 | 0.0682 | 0.125 | 0.0627 | 20 |
| Lys [20x] | 0.064 | 0.7900 | 0.025 | 0.8225 | 15.5 |
| Nac [5 mM] | −0.222 | 0.1615 | −0.315 | 0.1000 | 4 |
| Orn [20x] | −0.197 | 0.0419 | −0.196 | 0.0809 | 6.5 |
| RCit [20x] | 0.089 | 0.2309 | 0.158 | 0.0854 | 22 |
| RCitNac [20x/5 mM] | −0.337 | 0.0019 | −0.422 | <0.0001 | 1 |
| RCitNacQCar [20x/5 mM] | 0.056 | 0.3256 | 0.045 | 0.3334 | 15.5 |
| RCitNacQCarLHKVS [20x/5 mM] | 0.002 | 0.5616 | −0.036 | 0.9955 | 12 |
| RNac [20x/5 mM] | −0.192 | 0.0461 | −0.244 | 0.0664 | 6.5 |
| RQNac [20x/5 mM] | 0.235 | 0.2581 | 0.228 | 0.2878 | 27 |
| Ser [20x] | 0.076 | 0.2756 | 0.139 | 0.0378 | 19 |
| Trp [20x] | 0.171 | 0.1249 | 0.162 | 0.2243 | 24 |
| Val [20x] | 0.167 | 0.2593 | 0.315 | 0.0118 | 25.5 |

*[20x] Correspond to HMDB values

RCitNac greatly reduced TNF-α induced ICAM-1 expression levels in HLMVEC cells. Gly, CitNac and Nac also reduced levels of ICAM-1 expression to a lesser extent. HLMVEC cells treated with RCitNacQCarLHKVS and RCitNacQCar moderately reduced TNF-α induced ICAM-1 expression levels. RCitNac, Nac, Gly, and CitNac greatly reduced VCAM-1 expression in HLMVEC cells. RCitNacQCarLHKVS, had a moderate effect on VCAM-1 expression in these cells, as did Cit, and Car.

Summary of results: As described, an ideal treatment is one that addresses the multifactorial pathology of SCD as represented by HLMVEC by reducing disease phenotypes (VCAM1, ICAM1, IL6). The ability of single amino acids and combinations to simultaneously impact these phenotypes was measured by a META-rank score (Tables 17 and 18). META-rank score is a composite measure that considers the optimal impact on all 3 phenotypes (e.g. decrease VCAM1, ICAM1, and IL6) in the HLMVEC model. An optimal amino acid or combination treatment (i.e. treatment that has the desired effect on all measures) has a lower score than a sub-optimal treatment (i.e. treatment has an undesirable effect on all measures). Based on META-rank the RCitNac was the optimal treatment, and the combinations RCitNacQCar and RCitNacQCarLHKVS were among the optimal treatment conditions.

Example 10. Assessment of the Pharmacokinetics of Multiple Compounds Following Oral Dose Administration to Male Sprague-Dawley Rats Summary A pharmacokinetic (PK) analysis was performed on plasma concentrations of various combinations of amino acid compounds administered by oral gavage to male Sprague-Dawley rats. Four animals were dosed with RCit- NacQCarLHKVS, a test article comprising ten amino acid components: arginine, citrulline, N-acetylcysteine, glutamine, carnitine, leucine, histidine, lysine, valine, and serine (Table 19). Animals were fasted for 2 hours prior to dose administration. Plasma samples were taken immediately pre-dose and 0.5, 1, 2, 3, 4, and 5 hours post-dose.

Bioanalysis of collected plasma samples for amino acid content was performed at Axcella Health using an LC-MS method (Section 2.1). Bioanalytical data were analyzed using noncompartmental analysis with Phoenix® WinNonLin® (v8.1).

Most compounds dosed as part of RCitNacQCarLHKVS rose in concentration after dosing, reaching maximum concentration between 0.5 and 3 hours post-dose, with carnitine and N-acetylcysteine the only exceptions. Carnitine continuously increased over the course of the five-hour time course, while N-acetylcysteine was not detected in plasma. PK parameters, such as $T_{max}$, $C_{max}$, and $AUC_{0-5h}$ were tabulated.

Methodology
Summary of Sample Analysis Procedures

An LC/MS method utilizing HILIC chromatography and high-resolution mass spectrometry was used to quantify amino acids in rat plasma. The samples were prepared by protein precipitation and spiked with stable-labeled amino acid internal standard for each analyte. Calibration standards were used for absolute quantification and the linear range for each analyte was generally from 10 to 2000 µM. QCs, spiked into rat plasma, were utilized to assess the accuracy of the method.

Pharmacokinetic (PK) Analysis

PK parameters of test article components were determined from individual rat plasma concentration-time data by employing a noncompartmental approach using Phoenix WinNonlin® (Version 8.1) software. Nominal times were used to calculate the toxicokinetic parameters. Plasma pharmacokinetic parameters such as $T_{max}$, $C_{max}$, and $AUC_{0-5h}$ were tabulated, as appropriate. This program analyzed data using the standard methods described by Gibaldi and Perrier (see M. Gibaldi and D. Perrier, Pharmacokinetics, 2nd edition, New York: Marcel-Dekker, Inc.; 1982.).

TABLE 19

Test Article Composition

| Amino Acid Component | Dose (mg/kg) |
|---|---|
| Arginine | 617.3 |
| Citrulline | 411.6 |
| N-Acetylcysteine | 133.8 |
| Glutamine | 514.4 |
| Carnitine | 102.9 |
| Leucine | 308.7 |
| Histidine | 102.9 |
| Lysine | 154.3 |
| Valine | 102.9 |
| Serine | 257.2 |

Results
Arginine

Baseline concentrations of arginine ranged from 74.9 to 112 µM across all animals. After dosing, mean maximum arginine concentration ($C_{max}$) in animals dosed RCitNacQCarLHKVS was 565 µM, occurring 0.5-2.0 hours post-dose. Arginine $AUC_{0-5h}$ for animals was 2210 µM*h on average.

Citrulline

Baseline concentrations of citrulline ranged from 31.6 to 62.7 µM across all animals. After dosing, mean maximum citrulline concentration ($C_{max}$) in animals dosed RCitNacQCarLHKVS was 583 µM, occurring 2.0-3.0 hours post-dose. Citrulline $AUC_{0-5h}$ for animals was 2090 µM*h on average.

Glutamine

Baseline concentrations of glutamine ranged from 401 to 615 µM across all animals. After dosing, mean maximum glutamine concentration ($C_{max}$) in animals dosed RCitNacQCarLHKVS was 605 µM, occurring 0.5 hours post-dose. Glutamine $AUC_{0-5h}$ for animals was 2370 µM*h on average.

CONCLUSIONS

Following dosing of test article RCitNacQCarLHKVS, plasma concentrations of component amino acids tended to reach maximum value at 0.5 to 3.0 hours after dose and decline with time.

TABLE 20

| Compound | | $T_{max}$ (h) | $C_{max}$ (µM) | $AUC_{0-5\ h}$ (µM * h) |
|---|---|---|---|---|
| Arginine | Mean | 1.38 | 565 | 2210 |
| | SD | 0.750 | 42.7 | 191 |
| Carnitine | Mean | 5.00 | 83.8 | 237 |
| | SD | 0.00 | 6.87 | 12.0 |
| Citrulline | Mean | 2.50 | 583 | 2090 |
| | SD | 0.577 | 95.3 | 227 |
| Glutamine | Mean | 0.500 | 605 | 2370 |
| | SD | 0.00 | 22.1 | 129 |
| Histidine | Mean | 1.25 | 41.9 | 157 |
| | SD | 1.19 | 5.43 | 25.9 |
| Leucine | Mean | 0.500 | 170 | 586 |
| | SD | 0.00 | 23.0 | 54.6 |
| Lysine | Mean | 1.00 | 337 | 1350 |
| | SD | 0.707 | 26.9 | 72.5 |
| Serine | Mean | 2.25 | 285 | 1030 |
| | SD | 1.50 | 58.3 | 141 |
| Valine | Mean | 1.00 | 126 | 463 |
| | SD | 0.707 | 14.6 | 40.3 |

Figure 2A:
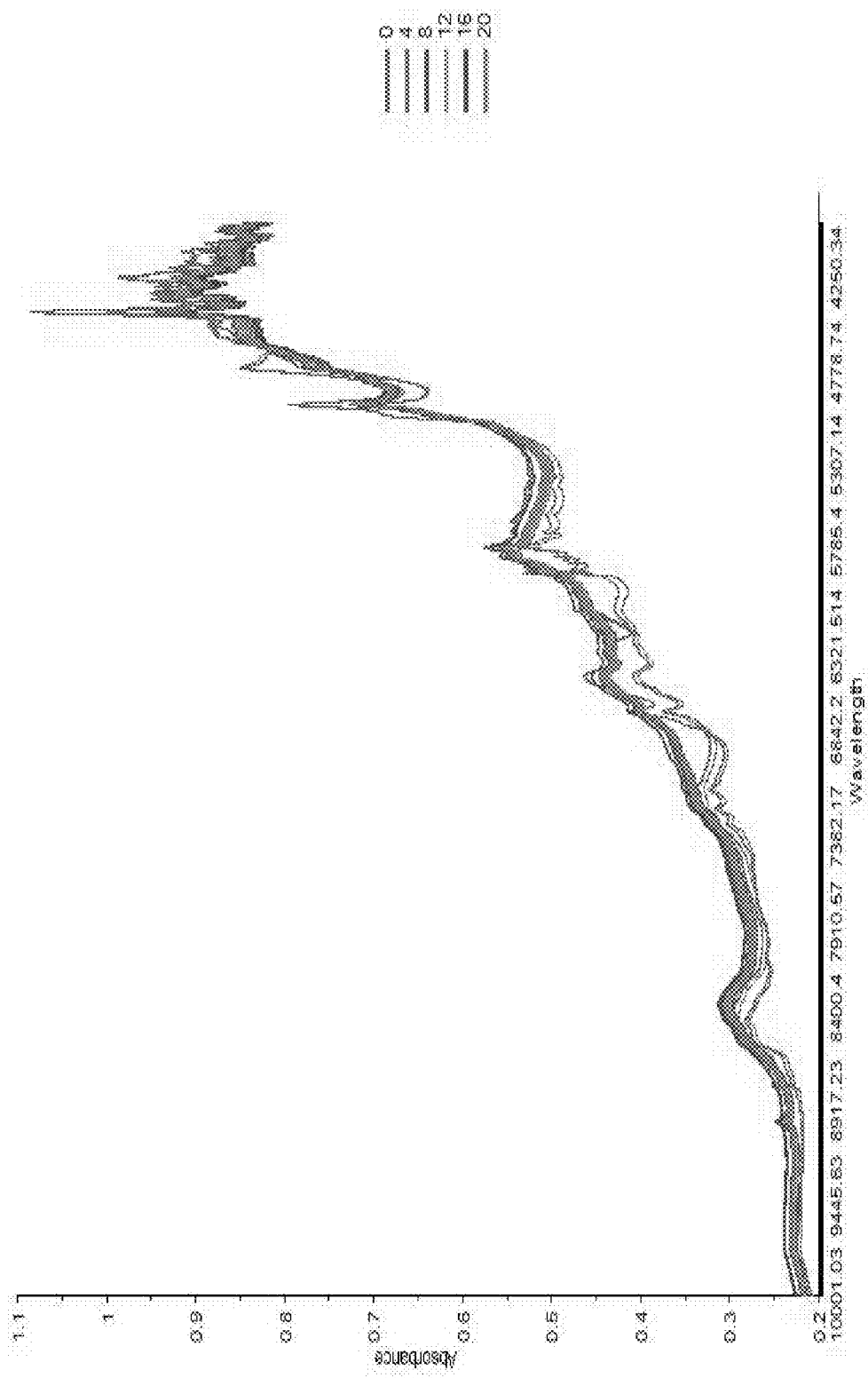
FIG. 2A shows alignments of NIR spectrographs taken at increasing blending times (0, 4, 8, 12, 16, and 20 minutes) of a PGDBP.
Figure 2B:
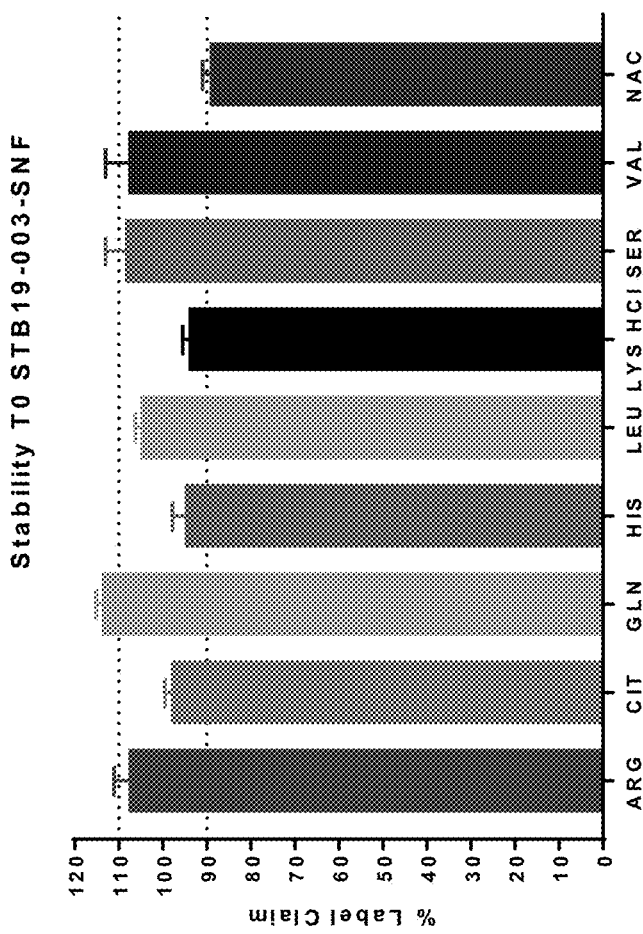
FIG. 2B is a graph showing the average amount and standard error of amino acid in 4 random samples from the 20 minute blending time of a PGDBP (the PGDBP of FIG. 1A).

Example 11. Monitoring Homogeneity in Real Time Using NIR—Additional Combinations and V-blender Blending FIG. 2A shows the time-dependent approach to blend uniformity during the processing of a third additional exemplary combination of amino acid entities (the exemplary combination of Table 3) using a V-blender. Samples for generating NIR spectra were taken every four minutes. The collapse of the NIR spectra at late time points indicates that the combination has achieved blend uniformity. FIG. 2B represents the average of four randomly-selected independent stick packs and amino acid recovery data is expressed as a 90-110 percent of label claim. The data when taken together, indicate blend and content uniformity had been achieved.

These experiments demonstrate that the methods described herein may be used to achieve blend and content uniformity for additional combinations of amino acid entities and that a variety of blending techniques, including V-blender blending, are suitable for achieving uniformity.

Example 12. Treatment of Sickle Cell Disease Patients with an Amino Acid Composition The study described herein features the administration of a composition including amino acids to treat patients with Sickle Cell Disease (SCD). This study's aim is to assess the food safety and tolerability of the composition over 12 weeks in subjects with sickle cell disease (SCD).

Safety and tolerability will be assessed by: reported clinical adverse events; physical examinations, vital sign and ECG; and clinical laboratory tests including changes in hematology, chemistry, plasma amino acids and other inflammation and vascular adhesion/functional markers. Structural and functional changes will be assessed by: multiparametric magnetic resonance imaging for brain and kidney perfusion; the 6-Minute walk metric; and pulse oximetry. Approximately 48 male and female subjects≥12 years old with a prior confirmed diagnosis of SCD will be assessed.

Figure 3:
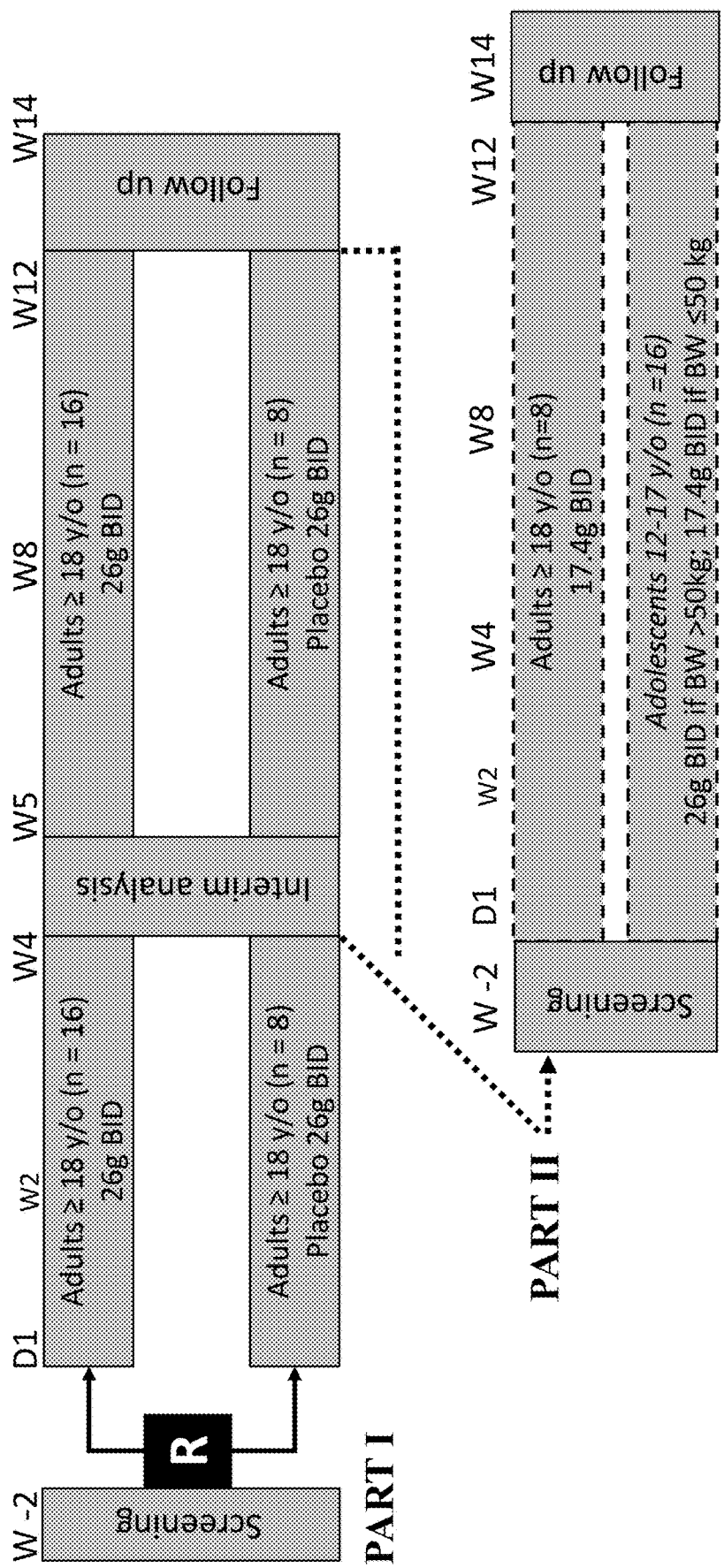
FIG. 3 is a schematic showing the design of a clinical study featuring the administration of an amino acid composition to subjects having sickle cell disease.

The study is envisioned to be conducted in two parts (FIG. 3). Part I: The study will initiate in approximately 24 adult (≥18 y/o) subjects with SCD as a double-bind placebo-controlled randomized (2:1 active:placebo) study for up to 12 weeks of composition administration at 26.3 g BID (52.6 g/day). Based on ongoing tolerability and safety monitoring, the amounts and/or regimen of the composition may be adjusted downward. Part II: Pending the results from either the interim analysis after Week 4 and/or the end-of-study results from Week 12 of Part I, Part II may subsequently initiate in a separate cohort of approximately eight additional adult (≥18 y/o) and sixteen (16) adolescent (12-17 y/o) subjects. Anticipated amount of the composition for adult subjects in Part II is 17.4 g BID (34.8 g/day); for adolescent subjects, amounts will be adjusted based on their body weight (BW): 26.3 g BID if BW>50 kg and 17.4 g BID if BW≤50 kg. The amounts and/or regimen of composition may be further adjusted pending the results from Part I. There will be no separate placebo arm in Part II.

Part I & Part II: Baseline (Day 1) to Week 12: In Part I, randomization should occur approximately 3-5 days prior to the Day 1 visit and will be based on a 2:1 ratio of active:placebo. Assigned study composition [composition 26.3 g BID (52.6 g/day) or Placebo] will be shipped to the clinical site upon randomization of each subject. Once randomization has occurred, subjects will present to the study site on Day 1 for their baseline assessments. In Part II, as there is no separate placebo arm, all subjects will receive composition as either a fixed amount in adults (eg 17.4 g BID), or body weight adjusted amounts in adolescent subjects (eg 26 g BID if BW>50 kg and 17.4 g BID if BW≤50 kg).

The composition is composed of amino acids. Placebo product is excipient matched to the composition. The study compositions are provided as dry powder in individual stick packs. Each stick pack contains ~8.76 g of amino acids per stick pack. The prescribed number of stick packs for each administration [e.g. either 2, 3, or 4 stick packs BID] which are then mixed in ~6 oz (~180 mL) of water, and then immediately consumed twice daily approximately 30 min (i.e., 30±5 minutes) before meals (e.g., before breakfast and dinner or before lunch and dinner, if breakfast is not a usual part of their daily routine) for the entire duration of the study.

Summary of Examples

Sickle cell disease is complex and driven by a multitude of unique mechanisms. Maintaining blood health and function requires coordination of many biological, cellular and molecular processes. As shown in the Examples herein, the amino acid compositions disclosed in this application (including LRQNacHKVSCitCar, RCitNacQCar, and RCitNac) were able to [1] mitigate inflammatory cytokines in human vascular endothelial cells, [2] reduce cellular adhesion molecule expression in human vascular endothelial cells, and [3] protect against insults to human RBC deformability, whereas compositions such as Q, RCit, and NAC were only able to influence some, but not all of those important processes required for maintaining blood health. In fact, glutamine (Q)—which is FDA approved for the treatment of sickle cell disease—displayed negative or undesirable effects in particular assays herein that are mitigated in combinations.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

What is claimed is:

1. A method of treating a hemoglobinopathy or a thalassemia, comprising administering to a subject in need thereof an effective amount of a composition comprising:
 a) an arginine amino acid entity chosen from:
  i) L-arginine or a salt thereof,
  ii) a dipeptide or salt thereof, or tripeptide or salt thereof, comprising L-arginine,
  iii) creatine or a salt thereof, or
  iv) a dipeptide or salt thereof, or tripeptide or salt thereof, comprising creatine;
 b) a citrulline amino acid entity chosen from L-citrulline or a salt thereof or a dipeptide or salt thereof, or tripeptide or salt thereof, comprising L-citrulline;
 c) a N-acetylcysteine (NAC)-entity chosen from NAC or a salt thereof or a dipeptide or salt thereof comprising NAC;
 (d) a glutamine amino acid entity chosen from L-glutamine or a salt thereof or a dipeptide or salt thereof, or tripeptide or salt thereof, comprising L-glutamine;
 (e) one or both of i) a serine amino acid entity chosen from L-serine or a salt thereof or a dipeptide or salt thereof, or tripeptide or salt thereof, comprising L-serine or ii) a carnitine entity chosen from L-carnitine or a salt thereof, or a dipeptide or salt thereof, comprising L-carnitine;
 one, two, or more of: (f) a valine amino acid entity chosen from L-valine or a salt thereof or a dipeptide or salt thereof, or tripeptide or salt thereof, comprising L-valine, (g) a histidine amino acid entity chosen from L-histidine or a salt thereof or a dipeptide or salt thereof, or tripeptide or salt thereof, comprising L-histidine, or (h) a lysine amino acid entity chosen from L-lysine or a salt thereof or a dipeptide or salt thereof, or tripeptide or salt thereof, comprising L-lysine, and/or
 (i) a leucine amino acid entity chosen from:
  i) L-leucine or a salt thereof,
  ii) a dipeptide or salt thereof, or tripeptide or salt thereof, comprising L-leucine, or
  iii) β-hydroxy-β-methylbutyrate (HMB) or a salt thereof,
 (i) wherein the composition does not comprise a peptide of more than 20 amino acid residues in length, or if a peptide of more than 20 amino acid residues in length is present, the peptide is present at less than: 10 wt. % of the total wt. of the composition (in dry form);

(ii) at least 50 wt. % of the total wt. of the composition (in dry form) is one or more amino acid entities in free form; and (iii) the wt. % of the citrulline amino acid entity is greater than the wt. % of the NAC-entity, thereby treating the hemoglobinopathy or the thalassemia in the subject.

2. The method of claim 1, wherein at least: 42 wt. % of the total wt. of the composition (in dry form) is one, two, three, four, five, six, seven, eight, or more of (a)-(i) in free amino acid form in the composition.

3. The method of claim 1, wherein the total wt. % of (a)-(i) is greater than the total wt. % of one, two, or three of other amino acid entity components, non-amino acid entity protein components, or non-protein components in the composition (in dry form).

4. The method of claim 1, wherein the composition comprises a combination of 18 or fewer amino acid entities.

5. The method of claim 1, wherein the composition comprises:
   a) L-leucine or a salt thereof,
   b) L-arginine or a salt thereof,
   c) L-glutamine or a salt thereof,
   d) NAC or a salt thereof,
   e) L-citrulline or a salt thereof,
   f) L-carnitine or a salt thereof,
   g) L-serine or a salt thereof,
   h) L-valine or a salt thereof,
   i) L-histidine or a salt thereof, and
   j) L-lysine or a salt thereof.

6. The method of claim 1, wherein the hemoglobinopathy or thalassemia is chosen from: a sickle cell disease, α-thalassemia, or β-thalassemia.

7. The method of claim 1, wherein the composition is formulated with a pharmaceutically acceptable carrier.

8. The method of claim 1 wherein the composition is formulated as a dietary composition.

9. The method of claim 1, wherein the composition is a pharmaceutical grade dry blended preparation (PGDBP).

10. The method of claim 1, wherein one, two, or three of the following:
   (i) the wt. % of the citrulline amino acid entity in the composition (in dry form) is at least 50% greater than the wt. % of the NAC-entity;
   (ii) the wt. % of the leucine amino acid entity, the citrulline amino acid entity, and the NAC entity is at least: 20 wt. % of the amino acid entity components or total components in the composition (in dry form), but not more than 80 wt. % of the amino acid entity components or total components in the composition (in dry form); or
   (iii) the wt. % of the citrulline amino acid entity is at least: 5 wt. % of the amino acid entity components in the composition (in dry form), but not more than 60 wt. % of the amino acid entity components in the composition (in dry form).

11. The method of claim 1, wherein one, two, three, or four of the following:
   (i) the wt. % of the leucine amino acid entity, the citrulline amino acid entity, the NAC entity, the carnitine amino acid entity, and the glutamine amino acid entity is at least: 40 wt. % of the amino acid entity components or total components in the composition (in dry form), but not more than 90 wt. % of the amino acid entity components or total components in the composition (in dry form);
   (ii) the wt. % of the citrulline amino acid entity in the composition (in dry form) is at least 50% greater than the wt. % of the carnitine amino acid entity;
   (iii) the wt. % of the glutamine amino acid entity in the composition (in dry form) is at least 40% greater than the wt. % of the citrulline amino acid entity; or
   (iv) the wt. % of the citrulline amino acid entity in the composition (in dry form) is at least 20% greater than the wt. % of the carnitine amino acid entity.

12. The method of claim 1, wherein the composition comprises two, three, or all of: (g) a serine amino acid entity, (h) a valine amino acid entity, (i) a histidine amino acid entity, or (j) a lysine amino acid entity.

13. The method of claim 6, wherein the sickle cell disease is chosen from: sickle cell anemia (HbSS), hemoglobin SC disease (HbSC), sickle β$^+$-thalassemia (HbS/(β+), sickle β$^0$-thalassemia)(HbS/β$^0$), hemoglobin SE disease, hemoglobin SD disease, or hemoglobin SO disease.

14. The method of claim 1, wherein the composition comprises:
   a) L-arginine or a salt thereof,
   b) L-citrulline or a salt thereof,
   c) NAC or a salt thereof,
   d) L-carnitine or a salt thereof, and
   e) L-glutamine or a salt thereof.

\* \* \* \* \*